(12) United States Patent
Hess et al.

(10) Patent No.: US 10,159,730 B2
(45) Date of Patent: Dec. 25, 2018

(54) FOWL ADENOVIRUS VACCINE

(71) Applicant: VETERINARMEDIZINISCHE UNIVERSITAT WIEN, Vienna (AT)

(72) Inventors: Michael Hess, Klosterneuburg (AT); Anna Schachner, Vienna (AT); Ana Marek, Vienna (AT); Barbara Jaskulska, Vienna (AT)

(73) Assignee: VETERINÄRMEDIZINISCHE UNIVERSITÄT WIEN, Vienna (AT)

( * ) Notice: Subject to any disclaimer, the term of this patent is extended or adjusted under 35 U.S.C. 154(b) by 0 days.

(21) Appl. No.: 14/913,152

(22) PCT Filed: Aug. 19, 2014

(86) PCT No.: PCT/EP2014/067654
§ 371 (c)(1),
(2) Date: Feb. 19, 2016

(87) PCT Pub. No.: WO2015/024932
PCT Pub. Date: Feb. 26, 2015

(65) Prior Publication Data
US 2016/0193323 A1 Jul. 7, 2016

(30) Foreign Application Priority Data
Aug. 19, 2013 (EP) .................................. 13180849

(51) Int. Cl.
| A61K 38/00 | (2006.01) |
| C07K 14/435 | (2006.01) |
| C07K 14/475 | (2006.01) |
| A01K 67/00 | (2006.01) |
| A01K 67/033 | (2006.01) |
| A61K 39/235 | (2006.01) |
| A61K 39/12 | (2006.01) |
| C12N 7/00 | (2006.01) |
| G01N 33/68 | (2006.01) |
| A61K 39/00 | (2006.01) |

(52) U.S. Cl.
CPC ............ *A61K 39/235* (2013.01); *A61K 39/12* (2013.01); *C12N 7/00* (2013.01); *G01N 33/6854* (2013.01); *A61K 2039/505* (2013.01); *A61K 2039/545* (2013.01); *A61K 2039/552* (2013.01); *A61K 2039/55505* (2013.01); *A61K 2039/55555* (2013.01); *A61K 2039/55566* (2013.01); *A61K 2039/55588* (2013.01); *C12N 2710/10222* (2013.01); *C12N 2710/10234* (2013.01); *G01N 2333/075* (2013.01); *G01N 2800/26* (2013.01); *G01N 2800/52* (2013.01)

(58) Field of Classification Search
CPC .... A61K 2039/552; A61K 2039/55505; A61K 2039/55555; A61K 2039/55566; A61K 39/12

See application file for complete search history.

(56) References Cited

U.S. PATENT DOCUMENTS

| 2007/0105193 A1 | 5/2007 | Vilalta et al. ............... 435/69.1 |
| 2011/0165224 A1* | 7/2011 | Gomis ................. A61K 39/235 424/450 |
| 2016/0199484 A1 | 7/2016 | Hess et al. ................. 424/186.1 |

FOREIGN PATENT DOCUMENTS

| EP | 1001030 | 5/2000 |
| EP | 2839838 | 2/2015 |
| JP | 2016-528270 | 9/2016 |
| WO | WO 2003/039593 | 5/2003 |
| WO | WO 2015/024929 | 2/2015 |

OTHER PUBLICATIONS

Shah et al., A subunit vaccine against hydropericardium syndrome using adenovirus penton capsid protein, Vaccine, 2012, 30(50):7153-7156.*
Shah et al., Vaccine, 2012, 30(50):7153-7156.*
Marek et al., Veterinary Microbiology, 2012, 156(3-4):411-417.*
Sequence alignment of SEQ ID No. 31 with UniProt database access No. H8WQW9_ADEN by Marek et al. *Vet Microbiol* 2012; 156: 411-417.
Sequence alignment of SEQ ID No. 37 with UniProt database access No. SPIK2_ADEG1 by Chiocca et al in *J. of Virology*, 1996; 79: 2939-2949.
Sequence alignment of SEQ ID No. 39 with UniProt database access No. Q77VH5 by Ojkic et al. in *J. of General Virology*, 2000; 81: 1833-1837.
Sequence alignment of SEQ ID No. 40 with UniProt database access No. E9KLB3_9ADEN by Grgic et al in *Virus Research* 2011; 156: 91-97.
Sequence alignment of SEQ ID No. 41 with UniProt database access No. H8WR01_9ADEN by Marek et al in *Bet Microbiol* 2012; 156: 411-418.
Alvarado, I.R. et al.: "Genetic Characterization, Pathogenicity, and Protection Studies with an Avian Adenovirus Isolate Associated with Inclusion Body Hepatitis", Avian Diseases, 51, (2007), pp. 27-32.
Anjum, A.D: "Experimental transmission of hydropericardium syndrome and protection against it in commercial broiler chickens", Avian Pathology, 19, (19990), pp. 655-660.
Fingerut, E. et al.: "A Subunit Vaccine Against the Adenovirus Egg-drop Syndrome Using Part of its Fiber Protein", Vaccine, 21, (2003), pp. 2761-2766.
Griffin, B. D. et al.: "Coding potential and transcript analysis of fowl adenovirus 4: insight in upstream ORFs and common sequence features in adenoviral transcripts", Journal of General Virology, 92, (2011), pp. 1260-1272.
Hess, M. et al.: "The Avian Adenovirus Penton: Two Fibres and One Base", J. Mol. Biol., 252, (1995), pp. 379-385.

(Continued)

*Primary Examiner* — Barry A Chestnut
(74) *Attorney, Agent, or Firm* — Norton Rose Fulbright US LLP

(57) ABSTRACT

Disclosed is a vaccine comprising fiber (2) protein of Fowl Adeno-virus C (FAdV-C) or an immunogenic fragment thereof for use in preventing hepatitis-hydropericardium Syndrome (HHS) in birds, preferably in poultry, especially in broilers.

19 Claims, 8 Drawing Sheets

Figure 1:
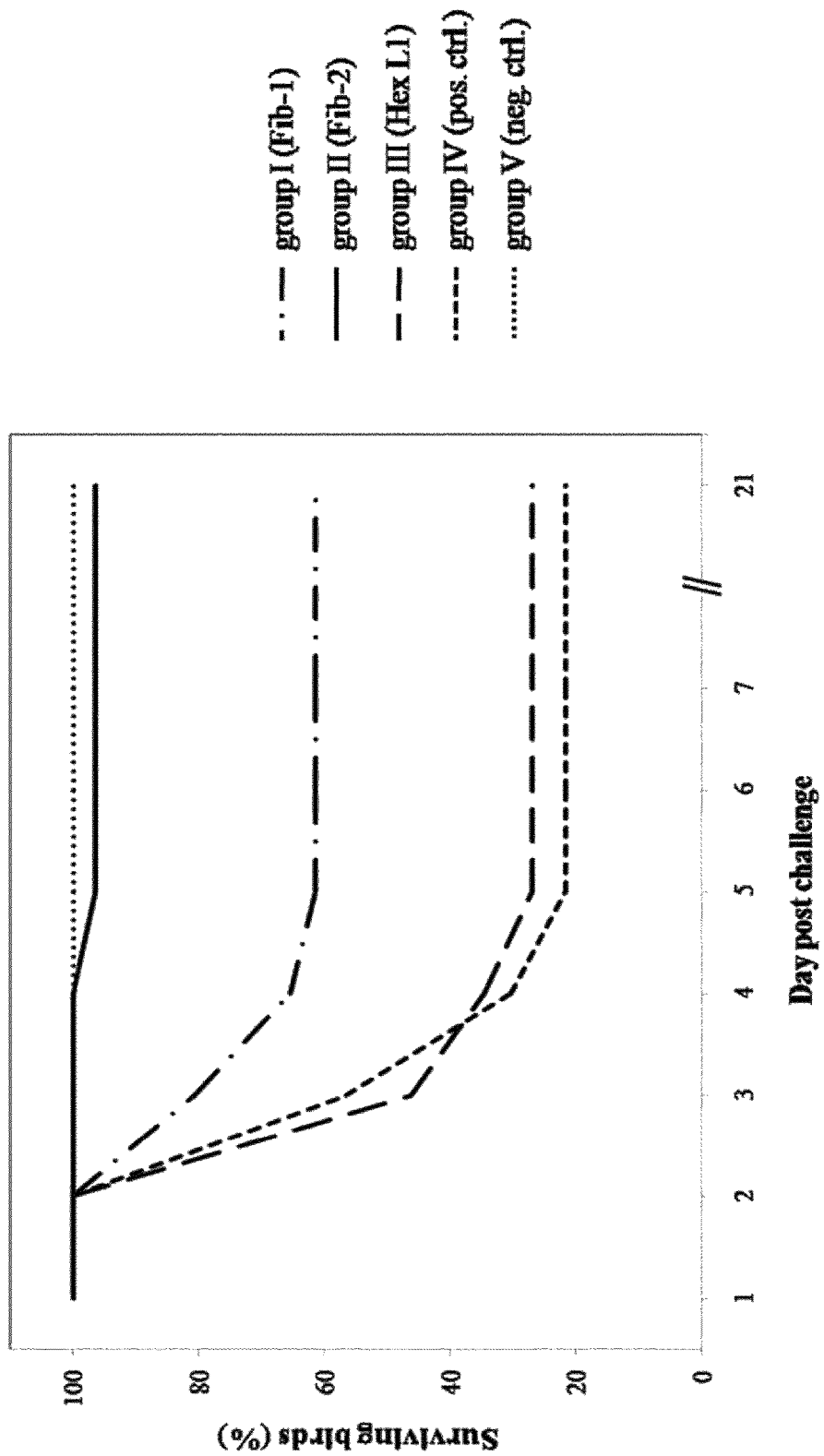

Specification includes a Sequence Listing.

(56) References Cited

OTHER PUBLICATIONS

Hou, Y. et al.: "Prediction and Identification of T Cell Epitopes in the H5N1 Influenza Virus Nucleoprotein in Chicken", PLoS ONE, 7(6), (2012), pp. 1-13.
Marek, A. et al.: "Two fiber genes of nearly equal lengths are a common distinctive feature of Fowl adenovirus C members", Veterinary Microbiology, 156, (2012), pp. 411-417.
Schachner, A. et al.: "Recombinant FAdV-4 fiber-2 protein protects chickens against hepatitis-hydropericardium syndrome (HHS)", Vaccine, 32, (2014), pp. 1086-1092.
Shah, M.S. et al.: "A subunit vaccine against hydropericardium syndrome using adenovirus penton capsid protein", Vaccine, 30, (2012), pp. 7153-7156.
Song, J. et al.: "Human adenovirus type 41 possesses different amount of short and long fibers in the virion", Virology, (2012), pp. 336-342.
Tan, P.K. et al.: "Defining CAR as a cellular receptor for the avian adenovirus CELO using a genetic analysis of the two viral fibre proteins", Journal of General Virology, 82, (2001), pp. 1465-1472.
Wallny, H. et al.: "Peptide motifs of the single dominantly expressed class I molecule explain the striking MHC-determined response to Rous sarcoma virus in chickens", PNAS, 103(5), pp. 1434-1439.
European Office Communication issued in Corresponding European Application No. 13180860.2, dated May 8, 2014.
Grgic et al., "Pathogenicity and Cytokine Gene Expression Pattern of a Serotype 4 Fowl Adenovirus Isolate", PLoS ONE, 8(10): e77601, 2013.
Gunes et al., "Realtime PCR assay for universal detection and quantitation of all five species of fowl adenoviruses (FAdVA to FAdVE)", Journal of Virological Methods, 183: 147-153, 2012.
International Search Report and Written Opinion issued in PCT/EP2014/067647, dated Mar. 25, 2015.
Mazaheri et al., "Some strains of serotype 4 fowl adenoviruses cause inclusion body hepatitis and hydropericardium syndrome in chickens", Avian Pathology, 27: 269-276, 1998.
Meulemans et al., "Polymerase chain reaction combined with restriction enzyme analysis for detection and differentiation of fowl adenoviruses", Avian Pathology, 30: 655-660, 2001.
Schat et al., Cell-Culture Methods, chapter 43, 2008.
Schonewille et al., "Specific-Pathogen-Free Chickens Vaccinated with a Live FAdV-4 Vaccine Are Fully Protected Against a Severe Challenge Even in the Absence of Neutralizing Antibodies", Avian Diseases, 54: 905-910, 2010.
Chiocca et al., "The Complete DNA Sequence and Genomic Organization of the Avian Adenovirus CELO", Journal of Virology, vol. 70, No. 5, (1996), pp. 2939-2949.
Choi et al., "Epidemiological investigation of outbreaks of fowl adenovirus infection in commercial chickens in Korea," Poultry Science, 91(1):2502-2506, (2012).
Chroboczek et al., "Adenovirus Fiber", Current Topics in Microbiology and Immunology, 199, (1995), pp. 163-200.
Farkas et al., "Completion of genome analysis of snake adenovirus type 1, a representative of the reptilian lineage within the novel genus Atadenovirus," Virus Research, 132(1):132-139, (2008).

Gahery-Segard et al., "Immune Response to Recombinant Capsid Proteins of Adenovirus in Humans: Antifiber and Anti-Penton Base Antibodies Have a Synergistic Effect on Neutralizing Activity", Journal of Virology, vol. 72, No. 3 (1998), pp. 2388-2397.
Gelderblom et al., "The Fibers of Fowl Adenoviruses", Archives of Virology, Vo. 72, No. 4, (1982), pp. 289-298.
Harrach et al., "Family Adenoviridae", Virus Taxonomy: Ninth Report of the International Committee on Taxonomy of Viruses, (2012), pp. 125-141.
Hong et al., "The 100K-Chaperone Protein from Adenovirus Serotype 2 (Subgroup C) Assists in Trimerization and Nuclear Localization of Hexons from Subgroups C and B Adenoviruses", Journal of Molecular Biology, vol. 352, (2005), pp. 125-138.
Lauring et al., "Rationalizing the development of live attenuated virus vaccines," Nature Biotechnology, 28(6): 573-579, (2010).
Mareck et al., "Classification of fowl adenoviruses by use of phylogenetic analysis and high-resolution melting-curve analysis of the hexon L1 gene region," Journal of Virological Methods, 170(1):147-154, (2010).
Marek et al., "The first whole genome sequence of a Fowl adenovirus B strain enables interspecies comparisons within the genus Aviadenovirus" Veterinary Microbiology, 166:250-256, (2013).
McFerran et al., "Avian adenoviruses," Revue Scientifique et Technique—Office International Despizooties/Scientific and Technoical Review, 19(1):589-601, (2000).
Nakamura et al., "Pathologic Study of Specific-Pathogen-Free Chicks and Hens Inoculated with Adenovirus Isolated from Hydropericardium Syndrome," Avian Diseases, 43(3):414, (1999).
Norrby, "The Structural and Functional Diversity of Adenovirus Capsid Components", Journal of General Virology, vol. 5, No. 2, (1969), pp. 221-236.
Office Action issued in European Application No. 14793022.3, dated Oct. 19, 2017.
Ojkic et al., "The Complete Nucleotide Sequence of Fowl Adenovirus Type 8", Journal of General Virology, vol. 81, (2000), pp. 1833-1837.
Schachner et al., "Fowl adenovirus-induced diseases and strategies for their control—a review on the current global situation," Avian Pathology, 1-16, (2017).
Schade et al., "Adenoviral Gizzard Erosion in Broiler Chickens in Germany," Avian Diseases, 57(1): 159-163, (2013).
Steer et al., "Application of high-resolution melting curve analysis for typing of fowl adenoviruses in field cases of inclusion body hepatitis," Australian Veterinary Journal, 89(5): 184-192, (2011).
U.S. National Institutes of Health NIH website, downloaded from: http://www.niaid.nih.gov/topics/vaccines/Pages/typesVaccines.aspx , last updated on Apr. 3, 2012.
Uniprot: "Alignment FAdV Fiber 2," 2017, Retrieved from the Internet URL: http://www.uniprot.org/align/A20140920A7434721E10EE6586998A056CCD0537E009819V.
Guardado-Calvo et al., "Structure of the C-terminal head domain of the fowl adenovirus type 1 long fiber," Journal of General Virology, (2007), 88:2407-2416.
Office Action issued in Corresponding Japanese Patent Application No. 2016-535460, dated Apr. 10, 2018.

\* cited by examiner

```
                                         610       620
                                ....|....|....|....|..
FIBER-2_PERU53                  PANSGTMIVGPVLYSCPAASV-
FIBER-2_PERU54                  PANSGTMIVGPVLYSCPAASVP
FIBER-2_C344                    PANSGTMIVGPVLYSCPAASVP
FIBER-2_K1013QT                 PANSGTMIVGPVLYSCPAASV-
FIBER-2_K1013                   PANSGTMIVGPVLYSCPAAS--
FIBER-2_K31                     PNNSGTMIVGPVLYSCPAGSLP
FIBER-2_K88-95                  PNNSGTMIVGPVLYSCPAASLP
FIBER-2_IV37                    PNNSGT----------------
FIBER-2_K99-97                  PNNSGT----------------
FIBER-2_C2B                     PNNSGTMIVGPVLYSCPAGSLP
FIBER-2_09-584                  PANSGTMIVGPVLYSCPAGSLP
FIBER-2_09-8846                 PANSGTMIVGPVLYSCPAGSLP
FIBER-2_09-2602                 PANSGT----------------
FIBER-2_DA60                    PANSGTMIVGPVLYSCPAASV-
FIBER-2_KR5                     PANSGTMIVGPVLYSCPAASVP
FIBER-2_ON1_GU188428            PANSGTMIVGPVLYSCPAASVP
FIBER-2_922-1                   PANSGTMTVGPVLYTCPAASVP
FIBER-2_INT4                    PANSGTMIVGPVLYSCPAASV-
FIBER-2_AG234                   PANSGTMIVGPVLYSCPAASVP
FIBER-2_K388-95                 PANSGTMIVGPVLYSCPAASVP
FIBER-2_CELO_AC000014           PTVNGTVAIGPVVHTCPAARAPVTV-
FIBER-2?_TADV-1_GU936707        PSVQGTATIGPVNYICEASQSPNVVP
FIBER_A2-A_AC000013             AASNGTTIGPIFYSCPTNELTRPT-
FIBER_HG_GU734104               NATAGTMTLGPIFFSCPALSTANAP-
FIBER_340                       AATTGTFVGPIVYSCPGNPLI-----
```

Fig. 5d

SEQUENCE LISTING

```
<160> NUMBER OF SEQ ID NOS: 33

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      fiber primer

<400> SEQUENCE: 1
ggatccatgt cggccctaat cg                                              22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      fiber primer

<400> SEQUENCE: 2
aggcctttag gggctcggag c                                               21

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      fiber primer

<400> SEQUENCE: 3
aggcctatgc tccgagcccc ta                                              22

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      fiber primer

<400> SEQUENCE: 4
tctagattac gggacggagg ctg                                             23
```

```
<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      fiber primer

<400> SEQUENCE: 5
aattccatgg acaagttcag gcagacggtc gt                                    32

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      fiber primer

<400> SEQUENCE: 6
taactcgagc tagtgatgcc gggacatcat                                       30

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      fiber primer

<400> SEQUENCE: 7
atggckcaga tggcyaagg                                                   19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      fiber primer

<400> SEQUENCE: 8
agcgcctggg tcaaaccga                                                   19

<210> SEQ ID NO 9
<211> LENGTH: 471
<212> TYPE: PRT
<213> ORGANISM: Fowl adenovirus C

<400> SEQUENCE: 9
```

Arg His Ser Glu Asn Gly Lys Pro Glu Thr Glu Ala Gly Pro Ser Pro
1               5                   10                  15

Ala Pro Ile Lys Arg Ala Lys Arg Met Val Arg Ala Ser Gln Leu Asp
            20                  25                  30

Leu Val Tyr Pro Phe Asp Tyr Val Ala Asp Pro Val Gly Gly Leu Asn
        35                  40                  45

Pro Pro Phe Leu Gly Gly Ser Gly Pro Leu Val Asp Gln Gly Gly Gln
    50                  55                  60

Leu Thr Leu Asn Val Thr Asp Pro Ile Ile Lys Asn Arg Ser Val
65                  70                  75                  80

Asp Leu Ala His Asp Arg Ser Leu Asp Val Asn Ala Gln Gly Gln Leu
                85                  90                  95

Ala Val Ala Val Asp Pro Glu Gly Ala Leu Asp Ile Thr Pro Asp Gly
            100                 105                 110

```
Leu Asp Val Lys Val Asp Gly Val Thr Val Met Val Asn Asp Asp Trp
        115                 120                 125
Glu Leu Ala Val Lys Val Asp Pro Ser Gly Gly Leu Asp Ser Thr Ala
130                 135                 140
Gly Gly Leu Gly Val Ser Val Asp Asp Thr Leu Leu Val Asp Gln Gly
145                 150                 155                 160
Glu Leu Gly Val His Leu Asn Gln Gln Gly Pro Ile Thr Ala Asp Ser
                165                 170                 175
Ser Gly Ile Asp Leu Glu Ile Asn Pro Asn Met Phe Thr Val Asn Thr
            180                 185                 190
Ser Thr Gly Ser Gly Val Leu Glu Leu Asn Leu Lys Ala Gln Gly Gly
        195                 200                 205
Ile Gln Ala Asp Ser Ser Gly Val Gly Val Ser Val Asp Glu Ser Leu
    210                 215                 220
Glu Ile Val Asn Asn Thr Leu Glu Val Lys Pro Asp Pro Ser Gly Pro
225                 230                 235                 240
Leu Thr Val Ser Ala Asn Gly Leu Gly Leu Lys Tyr Asp Thr Asn Thr
                245                 250                 255
Leu Ala Val Thr Ala Gly Ala Leu Thr Val Gly Gly Gly Ser Val
            260                 265                 270
Ser Thr Pro Ile Ala Thr Phe Val Ser Gly Ser Pro Ser Leu Asn Thr
        275                 280                 285
Tyr Asn Ala Thr Thr Val Asn Ser Ser Ala Asn Ala Phe Ser Cys Ala
    290                 295                 300
Tyr Tyr Leu Gln Gln Trp Asn Ile Gln Gly Leu Leu Val Thr Ser Leu
305                 310                 315                 320
Tyr Leu Lys Leu Asp Ser Ala Thr Met Gly Asn Arg Pro Gly Asp Leu
                325                 330                 335
Asn Ser Ala Asn Ala Lys Trp Phe Thr Phe Trp Val Ser Ala Tyr Leu
            340                 345                 350
Gln Gln Cys Asn Pro Ser Gly Ile Gln Ala Gly Thr Val Ser Pro Ser
        355                 360                 365
Thr Ala Thr Leu Thr Asp Phe Glu Pro Met Ala Asn Arg Ser Val Thr
    370                 375                 380
Ser Pro Trp Thr Tyr Ser Ala Asn Gly Tyr Tyr Glu Pro Ser Ile Gly
385                 390                 395                 400
Glu Phe Gln Val Phe Ser Pro Val Val Thr Gly Ala Trp Asn Pro Gly
                405                 410                 415
Asn Ile Gly Ile Arg Val Leu Pro Val Pro Val Thr Ala Ser Gly Asp
            420                 425                 430
Arg Tyr Thr Leu Leu Cys Tyr Ser Leu Gln Cys Thr Asn Ser Ser Ile
        435                 440                 445
Phe Asn Pro Ala Asn Ser Gly Thr Met Ile Val Gly Pro Val Leu Tyr
    450                 455                 460
Ser Cys Pro Ala Ala Ser Val
465                 470

<210> SEQ ID NO 10
<211> LENGTH: 472
<212> TYPE: PRT
<213> ORGANISM: Fowl adenovirus C

<400> SEQUENCE: 10

Arg His Ser Glu Asn Gly Lys Pro Glu Thr Glu Ala Gly Pro Ser Pro
1               5                   10                  15
```

```
Ala Pro Ile Lys Arg Ala Lys Arg Met Val Arg Ala Ser Gln Leu Asp
             20                  25                  30

Leu Val Tyr Pro Phe Asp Tyr Val Ala Asp Pro Val Gly Gly Leu Asn
         35                  40                  45

Pro Pro Phe Leu Gly Gly Ser Gly Pro Leu Val Asp Gln Gly Gly Gln
 50                  55                  60

Leu Thr Leu Asn Val Thr Asp Pro Ile Ile Lys Asn Arg Ser Val
 65                  70                  75                  80

Asp Leu Ala His Asp Arg Ser Leu Asp Val Asn Ala Gln Gly Gln Leu
                 85                  90                  95

Ala Val Ala Val Asp Pro Glu Gly Ala Leu Asp Ile Thr Pro Asp Gly
                100                 105                 110

Leu Asp Val Lys Val Asp Gly Val Thr Val Met Val Asn Asp Asp Trp
             115                 120                 125

Glu Leu Ala Val Lys Val Asp Pro Ser Gly Gly Leu Asp Ser Thr Ala
 130                 135                 140

Gly Gly Leu Gly Val Ser Val Asp Asp Thr Leu Leu Val Asp Gln Gly
145                 150                 155                 160

Glu Leu Gly Val His Leu Asn Gln Gln Gly Pro Ile Thr Ala Asp Ser
                 165                 170                 175

Ser Gly Ile Asp Leu Glu Ile Asn Pro Asn Met Phe Thr Val Asn Thr
             180                 185                 190

Ser Thr Gly Ser Gly Val Leu Glu Leu Asn Leu Lys Ala Gln Gly Gly
             195                 200                 205

Ile Gln Ala Asp Ser Ser Gly Val Gly Val Ser Val Asp Glu Ser Leu
     210                 215                 220

Glu Ile Val Asn Asn Thr Leu Glu Val Lys Pro Asp Pro Ser Gly Pro
225                 230                 235                 240

Leu Thr Val Ser Ala Asn Gly Leu Gly Leu Lys Tyr Asp Thr Asn Thr
                 245                 250                 255

Leu Ala Val Thr Ala Gly Ala Leu Thr Val Val Gly Gly Gly Ser Val
                 260                 265                 270

Ser Thr Pro Ile Ala Thr Phe Val Ser Gly Ser Pro Ser Leu Asn Thr
             275                 280                 285

Tyr Asn Ala Thr Thr Val Asn Ser Ser Ala Asn Ala Phe Ser Cys Ala
     290                 295                 300

Tyr Tyr Leu Gln Gln Trp Asn Ile Gln Gly Leu Leu Val Thr Ser Leu
305                 310                 315                 320

Tyr Leu Lys Leu Asp Ser Ala Thr Met Gly Asn Arg Pro Gly Asp Leu
                 325                 330                 335

Asn Ser Ala Asn Ala Lys Trp Phe Thr Phe Trp Val Ser Ala Tyr Leu
                 340                 345                 350

Gln Gln Cys Asn Pro Ser Gly Ile Gln Ala Gly Thr Val Ser Pro Ser
             355                 360                 365

Thr Ala Thr Leu Thr Asp Phe Glu Pro Met Ala Asn Arg Ser Val Thr
             370                 375                 380

Ser Pro Trp Thr Tyr Ser Ala Asn Gly Tyr Tyr Glu Pro Ser Ile Gly
385                 390                 395                 400

Glu Phe Gln Val Phe Ser Pro Val Val Thr Gly Ala Trp Asn Pro Gly
                 405                 410                 415

Asn Ile Gly Ile Arg Val Leu Pro Val Pro Val Thr Ala Ser Gly Asp
             420                 425                 430
```

```
Arg Tyr Thr Leu Leu Cys Tyr Ser Leu Gln Cys Thr Asn Ser Ser Ile
            435                 440                 445

Phe Asn Pro Ala Asn Ser Gly Thr Met Ile Val Gly Pro Val Leu Tyr
    450                 455                 460

Ser Cys Pro Ala Ala Ser Val Pro
465                 470

<210> SEQ ID NO 11
<211> LENGTH: 470
<212> TYPE: PRT
<213> ORGANISM: Fowl adenovirus C

<400> SEQUENCE: 11

Ser Glu Asn Gly Lys Pro Glu Thr Glu Ala Gly Pro Ser Pro Ala Pro
1               5                   10                  15

Ile Lys Arg Ala Lys Arg Met Val Arg Ala Ser Gln Leu Asp Leu Val
            20                  25                  30

Tyr Pro Phe Asp Tyr Val Ala Asp Pro Val Gly Gly Leu Asn Pro Pro
        35                  40                  45

Phe Leu Gly Gly Ser Gly Pro Leu Val Asp Gln Gly Gly Gln Leu Thr
    50                  55                  60

Leu Asn Val Thr Asp Pro Ile Ile Lys Asn Arg Ser Val Asp Leu
65                  70                  75                  80

Ala His Asp Pro Ser Leu Asp Val Asn Ala Gln Gly Gln Leu Ala Val
                85                  90                  95

Ala Val Asp Pro Glu Gly Ala Leu Asp Ile Thr Pro Asp Gly Leu Asp
            100                 105                 110

Val Lys Val Asp Gly Val Thr Val Met Val Asn Asp Asp Trp Glu Leu
        115                 120                 125

Ala Val Lys Val Asp Pro Ser Gly Gly Leu Asp Ser Thr Ala Gly Gly
    130                 135                 140

Leu Gly Val Ser Val Asp Asp Thr Leu Leu Val Asp Gln Gly Glu Leu
145                 150                 155                 160

Gly Val His Leu Asn Gln Gln Gly Pro Ile Thr Ala Asp Ser Ser Gly
                165                 170                 175

Ile Asp Leu Glu Ile Asn Pro Asn Met Phe Thr Val Asn Thr Ser Thr
            180                 185                 190

Gly Ser Gly Val Leu Glu Leu Asn Leu Lys Ala Gln Gly Gly Ile Gln
        195                 200                 205

Ala Asp Ser Ser Gly Val Gly Val Ser Val Asp Glu Ser Leu Glu Ile
    210                 215                 220

Val Asn Asn Thr Leu Glu Val Lys Pro Asp Pro Ser Gly Pro Leu Thr
225                 230                 235                 240

Val Ser Ala Asn Gly Leu Gly Leu Lys Tyr Asp Thr Asn Thr Leu Ala
                245                 250                 255

Val Thr Ala Gly Ala Leu Thr Val Val Gly Gly Gly Ser Val Ser Thr
            260                 265                 270

Pro Ile Ala Thr Phe Val Ser Gly Ser Pro Ser Leu Asn Thr Tyr Asn
        275                 280                 285

Ala Thr Thr Val Asn Ser Ser Ala Asn Ala Phe Ser Cys Ala Tyr Tyr
    290                 295                 300

Leu Gln Gln Trp Asn Ile Gln Gly Leu Leu Val Thr Ser Leu Tyr Leu
305                 310                 315                 320

Lys Leu Asp Ser Ala Thr Met Gly Asn Arg Pro Gly Asp Leu Asn Ser
                325                 330                 335
```

```
Ala Asn Ala Lys Trp Phe Thr Phe Trp Val Ser Ala Tyr Leu Gln Gln
                340             345                 350

Cys Asn Pro Ser Gly Ile Gln Ala Gly Thr Val Ser Pro Ser Thr Ala
            355                 360             365

Thr Leu Thr Asp Phe Glu Pro Met Ala Asn Arg Ser Val Thr Ser Pro
        370             375             380

Trp Thr Tyr Ser Ala Asn Gly Tyr Tyr Glu Pro Ser Ile Gly Glu Phe
385             390             395                 400

Gln Val Phe Ser Pro Val Val Thr Gly Ala Trp Asn Pro Gly Asn Ile
                405             410             415

Gly Ile Arg Val Leu Pro Val Pro Val Thr Ala Ser Gly Asp Arg Tyr
                420             425             430

Thr Leu Leu Cys Tyr Ser Leu Gln Cys Thr Asn Ser Ser Ile Phe Asn
            435             440             445

Pro Ala Asn Ser Gly Thr Met Ile Val Gly Pro Val Leu Tyr Ser Cys
            450             455             460

Pro Ala Ala Ser Val Pro
465             470

<210> SEQ ID NO 12
<211> LENGTH: 472
<212> TYPE: PRT
<213> ORGANISM: Fowl adenovirus C

<400> SEQUENCE: 12

Arg Arg His Ser Glu Asn Gly Lys Pro Glu Thr Glu Ala Gly Pro Ser
1               5                   10                  15

Pro Ala Pro Ile Lys Arg Ala Lys Arg Met Val Arg Ala Ser Gln Leu
                20                  25                  30

Asp Leu Val Tyr Pro Phe Asp Tyr Val Ala Asp Pro Val Gly Gly Leu
            35                  40                  45

Asn Pro Pro Phe Leu Gly Gly Ser Gly Pro Leu Val Asp Gln Gly Gly
        50                  55                  60

Gln Leu Thr Leu Asn Val Thr Asp Pro Ile Ile Ile Lys Asn Arg Ser
65                  70                  75                  80

Val Asp Leu Ala His Asp Pro Ser Leu Asp Val Asn Ala Gln Gly Gln
                85                  90                  95

Leu Ala Val Ala Val Asp Pro Glu Gly Ala Leu Asp Ile Thr Pro Asp
                100                 105                 110

Gly Leu Asp Val Lys Val Asp Gly Val Thr Val Met Val Asn Asp Asp
            115                 120                 125

Trp Glu Leu Ala Val Lys Val Asp Pro Ser Gly Gly Leu Asp Ser Thr
        130                 135                 140

Ala Gly Gly Leu Gly Val Ser Val Asp Asp Thr Leu Leu Val Asp Gln
145                 150                 155                 160

Gly Glu Leu Gly Val His Leu Asn Gln Gln Gly Pro Ile Thr Ala Asp
                165                 170                 175

Ser Ser Gly Ile Asp Leu Glu Ile Asn Pro Asn Met Phe Thr Val Asn
            180                 185                 190

Thr Ser Thr Gly Ser Gly Val Leu Glu Leu Asn Leu Lys Ala Arg Gly
            195                 200                 205

Gly Ile Gln Ala Gly Ser Ser Gly Val Gly Val Ser Val Asp Glu Ser
        210                 215                 220

Leu Glu Ile Val Asn Asn Thr Leu Glu Val Lys Pro Asp Pro Ser Gly
```

```
                225                 230                 235                 240
        Pro Leu Thr Val Ser Ala Asn Gly Leu Gly Leu Lys Tyr Asp Thr Asn
                            245                 250                 255

Thr Leu Ala Val Thr Ala Gly Ala Leu Thr Val Val Gly Gly Gly Ser
                        260                 265                 270

Val Ser Thr Pro Ile Ala Thr Phe Val Ser Gly Ser Pro Ser Leu Asn
                    275                 280                 285

Thr Tyr Asn Ala Thr Thr Val Asn Ser Ser Ala Asn Ala Phe Ser Cys
                290                 295                 300

Ala Tyr Tyr Leu Gln Gln Trp Asn Ile Gln Gly Leu Leu Val Thr Ser
        305                 310                 315                 320

Leu Tyr Leu Lys Leu Asp Ser Ala Thr Met Gly Asn Arg Pro Gly Asp
                        325                 330                 335

Leu Asn Ser Ala Asn Ala Lys Trp Phe Thr Phe Trp Val Ser Ala Tyr
                    340                 345                 350

Leu Gln Gln Cys Asn Pro Ser Gly Ile Gln Ala Gly Thr Val Ser Pro
                355                 360                 365

Ser Thr Ala Thr Leu Thr Asp Phe Glu Pro Met Ala Asn Arg Ser Val
        370                 375                 380

Thr Ser Pro Trp Thr Tyr Ser Ala Asn Gly Tyr Tyr Glu Pro Ser Ile
        385                 390                 395                 400

Gly Glu Phe Gln Val Phe Ser Pro Val Val Thr Gly Ala Trp Asn Pro
                        405                 410                 415

Gly Asn Ile Gly Ile Arg Val Leu Pro Val Pro Val Thr Ala Ser Gly
                    420                 425                 430

Asp Arg Tyr Thr Leu Leu Cys Tyr Ser Leu Gln Cys Thr Asn Ser Ser
                435                 440                 445

Ile Phe Asn Pro Ala Asn Ser Gly Thr Met Ile Val Gly Pro Val Leu
                    450                 455                 460

Tyr Ser Cys Pro Ala Ala Ser Val
        465                 470

<210> SEQ ID NO 13
<211> LENGTH: 468
<212> TYPE: PRT
<213> ORGANISM: Fowl adenovirus C

<400> SEQUENCE: 13

Ser Glu Asn Gly Lys Pro Glu Thr Glu Ala Gly Pro Ser Pro Ala Pro
        1               5                   10                  15

Ile Lys Arg Ala Lys Arg Met Val Arg Ala Ser Gln Leu Asp Leu Val
                        20                  25                  30

Tyr Pro Phe Asp Tyr Val Ala Asp Pro Val Gly Gly Leu Asn Pro Pro
                    35                  40                  45

Phe Leu Gly Gly Ser Gly Pro Leu Val Asp Gln Gly Gly Gln Leu Thr
                50                  55                  60

Leu Asn Val Thr Asp Pro Ile Ile Lys Asn Arg Ser Val Asp Leu
        65                  70                  75                  80

Ala His Asp Pro Ser Leu Asp Val Asn Ala Gln Gly Gln Leu Ala Val
                        85                  90                  95

Ala Val Asp Pro Glu Gly Ala Leu Asp Ile Thr Pro Asp Gly Leu Asp
                    100                 105                 110

Val Lys Val Asp Gly Val Thr Val Met Val Asn Asp Asp Trp Glu Leu
                115                 120                 125
```

```
Ala Val Lys Val Asp Pro Ser Gly Gly Leu Asp Ser Thr Ala Gly Gly
    130                 135                 140

Leu Gly Val Ser Val Asp Asp Thr Leu Val Asp Gln Gly Glu Leu
145                 150                 155                 160

Gly Val His Leu Asn Gln Gln Gly Pro Ile Thr Ala Asp Ser Ser Gly
                165                 170                 175

Ile Asp Leu Glu Ile Asn Pro Asn Met Phe Thr Val Asn Thr Ser Thr
            180                 185                 190

Gly Ser Gly Val Leu Glu Leu Asn Leu Lys Ala Gln Gly Gly Ile Gln
        195                 200                 205

Ala Asp Ser Ser Gly Val Gly Val Ser Val Asp Glu Ser Leu Glu Ile
    210                 215                 220

Val Asn Thr Leu Glu Val Lys Pro Asp Pro Ser Gly Pro Leu Thr
225                 230                 235                 240

Val Ser Ala Asn Gly Leu Gly Leu Lys Tyr Asp Thr Asn Thr Leu Ala
                245                 250                 255

Val Thr Ala Gly Ala Leu Thr Val Gly Gly Gly Ser Val Ser Thr
            260                 265                 270

Pro Ile Ala Thr Phe Val Ser Gly Ser Pro Ser Leu Asn Thr Tyr Asn
        275                 280                 285

Ala Thr Thr Val Asn Ser Ser Ala Asn Ala Phe Ser Cys Ala Tyr Tyr
    290                 295                 300

Leu Gln Gln Trp Asn Ile Gln Gly Leu Leu Val Thr Ser Leu Tyr Leu
305                 310                 315                 320

Lys Leu Asp Ser Ala Thr Met Gly Asn Arg Pro Gly Asp Leu Asn Ser
                325                 330                 335

Ala Asn Ala Lys Trp Phe Thr Phe Trp Val Ser Ala Tyr Leu Gln Gln
            340                 345                 350

Cys Asn Pro Ser Gly Ile Gln Ala Gly Thr Val Ser Pro Ser Thr Ala
        355                 360                 365

Thr Leu Thr Asp Phe Glu Pro Met Ala Asn Arg Ser Val Thr Ser Pro
    370                 375                 380

Trp Thr Tyr Ser Ala Asn Gly Tyr Tyr Glu Pro Ser Ile Gly Glu Phe
385                 390                 395                 400

Gln Val Phe Ser Pro Val Val Thr Gly Ala Trp Asn Pro Gly Asn Ile
                405                 410                 415

Gly Ile Arg Val Leu Pro Val Pro Val Thr Ala Ser Gly Asp Arg Tyr
            420                 425                 430

Thr Leu Leu Cys Tyr Ser Leu Gln Cys Thr Asn Ser Ser Ile Phe Asn
        435                 440                 445

Pro Ala Asn Ser Gly Thr Met Ile Val Gly Pro Val Leu Tyr Ser Cys
    450                 455                 460

Pro Ala Ala Ser
465

<210> SEQ ID NO 14
<211> LENGTH: 479
<212> TYPE: PRT
<213> ORGANISM: Fowl adenovirus C

<400> SEQUENCE: 14

Met Leu Arg Ala Pro Lys Arg Arg His Ser Glu Asn Gly Lys Pro Glu
1               5                   10                  15

Thr Glu Ala Gly Pro Ser Pro Ala Pro Ile Lys Arg Ala Lys Arg Val
            20                  25                  30
```

-continued

```
Val Arg Ala Ser Gln Leu Asp Leu Val Tyr Pro Phe Asp Tyr Val Ala
            35                  40                  45

Asp Pro Val Gly Gly Leu Asn Pro Pro Phe Leu Gly Gly Ser Gly Pro
        50                  55                  60

Leu Val Asp Gln Gly Gly Gln Leu Thr Leu Asn Val Thr Asp Pro Ile
65                  70                  75                  80

Ile Ile Lys Asn Arg Ser Val Asp Leu Ala His Asp Pro Ser Leu Asp
                85                  90                  95

Val Asn Ala Gln Gly Gln Leu Ala Val Ala Val Asp Pro Glu Gly Ala
            100                 105                 110

Leu Asp Ile Thr Pro Asp Gly Leu Asp Val Lys Val Asp Gly Val Thr
        115                 120                 125

Val Met Val Asn Asp Asp Trp Glu Leu Ala Val Lys Val Asp Pro Ser
    130                 135                 140

Gly Gly Leu Asp Ser Thr Ala Gly Gly Leu Gly Val Ser Val Asp Asp
145                 150                 155                 160

Thr Leu Leu Val Asp Gln Gly Glu Leu Gly Val His Leu Asn Gln Gln
                165                 170                 175

Gly Pro Ile Thr Ala Asp Ser Ser Gly Ile Asp Leu Glu Ile Asn Pro
            180                 185                 190

Asn Met Phe Thr Val Asn Thr Ser Thr Gly Ser Gly Val Leu Glu Leu
        195                 200                 205

Asn Leu Lys Ala Gln Gly Gly Ile Gln Ala Asp Ser Ser Gly Val Gly
    210                 215                 220

Val Ser Val Asp Glu Ser Leu Gln Ile Val Asn Asn Thr Leu Glu Val
225                 230                 235                 240

Lys Pro Asp Pro Ser Gly Pro Leu Thr Val Ser Ala Asn Gly Leu Gly
                245                 250                 255

Leu Lys Tyr Asp Thr Asn Thr Leu Ala Val Thr Ala Gly Ala Leu Thr
            260                 265                 270

Val Val Gly Gly Gly Ser Val Ser Thr Pro Ile Ala Thr Phe Val Ser
        275                 280                 285

Gly Ser Pro Ser Leu Asn Thr Tyr Asn Ala Thr Val Asn Ser Ser
    290                 295                 300

Ala Asn Ala Phe Ser Cys Ala Tyr Tyr Leu Gln Gln Trp Asn Ile Gln
305                 310                 315                 320

Gly Leu Leu Val Thr Ser Leu Tyr Leu Lys Leu Asp Ser Ala Thr Met
                325                 330                 335

Gly Asn Arg Pro Gly Asp Leu Asn Ser Ala Asn Ala Lys Trp Phe Thr
            340                 345                 350

Phe Trp Val Ser Ala Tyr Leu Gln Gln Cys Asn Pro Ser Gly Ile Gln
        355                 360                 365

Ala Gly Thr Val Ser Pro Ser Thr Ala Thr Leu Thr Asp Phe Glu Pro
    370                 375                 380

Met Ala Asn Arg Ser Val Thr Ser Pro Trp Thr Tyr Ser Ala Asn Gly
385                 390                 395                 400

Tyr Tyr Glu Pro Ser Ile Gly Glu Phe Gln Val Phe Ser Pro Val Val
                405                 410                 415

Thr Gly Ala Trp Asn Pro Gly Asn Ile Gly Ile Arg Val Leu Pro Val
            420                 425                 430

Pro Val Ser Ala Ser Gly Glu Arg Tyr Thr Leu Leu Cys Tyr Ser Leu
        435                 440                 445
```

```
Gln Cys Thr Asn Ala Ser Ile Phe Asn Pro Asn Asn Ser Gly Thr Met
450                 455                 460

Ile Val Gly Pro Val Leu Tyr Ser Cys Pro Ala Gly Ser Leu Pro
465                 470                 475

<210> SEQ ID NO 15
<211> LENGTH: 449
<212> TYPE: PRT
<213> ORGANISM: Fowl adenovirus C

<400> SEQUENCE: 15

Arg His Ser Glu Asn Gly Lys Pro Glu Thr Glu Ala Gly Pro Ser Pro
1               5                   10                  15

Ala Pro Ile Lys Arg Ala Lys Arg Met Val Arg Ala Ser Gln Leu Asp
                20                  25                  30

Leu Val Tyr Pro Phe Asp Tyr Val Ala Asp Pro Val Gly Gly Leu Asn
            35                  40                  45

Pro Pro Phe Leu Gly Gly Ser Gly Pro Leu Val Asp Gln Gly Gly Gln
50                  55                  60

Leu Thr Leu Asn Val Thr Asp Pro Ile Ile Ile Lys Asn Arg Ser Val
65                  70                  75                  80

Asp Leu Ala His Asp Pro Ser Leu Asp Val Asn Ala Gln Gly Gln Leu
                85                  90                  95

Ala Val Ala Val Asp Pro Glu Gly Ala Leu Asp Ile Thr Pro Asp Gly
            100                 105                 110

Leu Asp Val Lys Val Asp Gly Val Thr Val Met Val Asn Asp Asp Trp
        115                 120                 125

Glu Leu Ala Val Lys Val Asp Pro Ser Gly Gly Leu Asp Ser Thr Ala
130                 135                 140

Gly Gly Leu Gly Val Ser Val Asp Asp Thr Leu Leu Val Asp Gln Gly
145                 150                 155                 160

Glu Leu Gly Val His Leu Asn Gln Gln Gly Pro Ile Thr Ala Asp Ser
                165                 170                 175

Ser Gly Ile Asp Leu Glu Ile Asn Pro Asn Met Phe Thr Val Asn Thr
            180                 185                 190

Ser Thr Gly Ser Gly Val Leu Glu Leu Asn Leu Lys Ala Gln Gly Gly
        195                 200                 205

Ile Gln Ala Asp Ser Ser Gly Val Gly Val Ser Val Asp Glu Ser Leu
210                 215                 220

Gln Ile Val Asn Asn Thr Leu Glu Val Lys Pro Asp Pro Ser Gly Pro
225                 230                 235                 240

Leu Thr Val Val Gly Gly Ser Val Ser Thr Pro Ile Ala Thr Phe
                245                 250                 255

Val Ser Gly Ser Pro Ser Leu Asn Thr Tyr Asn Ala Thr Val Asn
            260                 265                 270

Ser Ser Ala Asn Ala Phe Ser Cys Ala Tyr Tyr Leu Gln Gln Trp Asn
        275                 280                 285

Ile Gln Gly Leu Leu Val Thr Ser Leu Tyr Leu Lys Leu Asp Ser Ala
290                 295                 300

Thr Met Gly Asn Arg Pro Gly Asp Leu Asn Ser Ala Asn Ala Lys Trp
305                 310                 315                 320

Phe Thr Phe Trp Val Ser Ala Tyr Leu Gln Gln Cys Asn Pro Ser Gly
                325                 330                 335

Ile Gln Ala Gly Thr Val Ser Pro Ser Thr Ala Thr Leu Thr Asp Phe
            340                 345                 350
```

```
Glu Pro Met Ala Asn Arg Ser Val Thr Ser Pro Trp Thr Tyr Ser Ala
            355                 360                 365

Asn Gly Tyr Tyr Glu Pro Ser Ile Gly Glu Phe Gln Val Phe Ser Pro
        370                 375                 380

Val Val Thr Gly Ala Trp Asn Pro Gly Asn Ile Gly Ile Arg Val Leu
385                 390                 395                 400

Pro Val Pro Val Ser Ala Ser Gly Glu Arg Tyr Thr Leu Leu Cys Tyr
                405                 410                 415

Ser Leu Gln Cys Thr Asn Ala Ser Ile Phe Asn Pro Asn Asn Ser Gly
            420                 425                 430

Thr Met Ile Val Gly Pro Val Leu Tyr Ser Cys Pro Ala Ala Ser Leu
            435                 440                 445

Pro

<210> SEQ ID NO 16
<211> LENGTH: 448
<212> TYPE: PRT
<213> ORGANISM: Fowl adenovirus C

<400> SEQUENCE: 16

Pro Glu Thr Glu Ala Gly Pro Ser Pro Ala Pro Ile Lys Arg Ala Lys
1               5                   10                  15

Arg Met Val Arg Ala Ser Gln Leu Asp Leu Val Tyr Pro Phe Asp Tyr
            20                  25                  30

Val Ala Asp Pro Val Gly Gly Leu Asn Pro Pro Phe Leu Gly Gly Ser
        35                  40                  45

Gly Pro Leu Val Asp Gln Gly Gln Leu Thr Leu Asn Val Thr Asp
    50                  55                  60

Pro Ile Ile Ile Lys Asn Arg Ser Val Asp Leu Ala His Asp Pro Ser
65                  70                  75                  80

Leu Asp Val Asn Ala Gln Gly Gln Leu Ala Val Ala Val Asp Pro Glu
                85                  90                  95

Gly Ala Leu Asp Ile Thr Pro Asp Gly Leu Asp Val Lys Val Asp Gly
            100                 105                 110

Val Thr Val Met Val Asn Asp Asp Trp Glu Leu Ala Val Lys Val Asp
        115                 120                 125

Pro Ser Gly Gly Leu Asp Ser Thr Ala Gly Gly Leu Gly Val Ser Val
    130                 135                 140

Asp Asp Thr Leu Leu Val Asp Gln Gly Glu Leu Gly Val His Leu Asn
145                 150                 155                 160

Gln Gln Gly Pro Ile Thr Ala Asp Ser Ser Gly Ile Asp Leu Glu Ile
                165                 170                 175

Asn Pro Asn Met Phe Thr Val Asn Thr Ser Thr Gly Ser Gly Val Leu
            180                 185                 190

Glu Leu Asn Leu Lys Ala Gln Gly Gly Ile Gln Ala Asp Ser Ser Gly
        195                 200                 205

Val Gly Val Ser Val Asp Glu Ser Leu Gln Ile Val Asn Asn Thr Leu
    210                 215                 220

Glu Val Lys Pro Asp Pro Ser Gly Pro Leu Thr Val Ser Ala Asn Gly
225                 230                 235                 240

Leu Gly Leu Lys Tyr Asp Thr Asn Thr Leu Ala Val Thr Ala Gly Ala
                245                 250                 255

Leu Thr Val Val Gly Gly Gly Ser Val Ser Thr Pro Ile Ala Thr Phe
            260                 265                 270
```

Val Ser Gly Ser Pro Ser Leu Asn Thr Tyr Asn Ala Thr Val Asn
            275                 280                 285

Ser Ser Ala Asn Ala Phe Ser Cys Ala Tyr Tyr Leu Gln Gln Asn Ile
290                 295                 300

Gln Gly Leu Leu Val Thr Ser Leu Tyr Leu Lys Leu Asp Ser Ala Thr
305                 310                 315                 320

Met Gly Asn Arg Pro Gly Asp Leu Asn Ser Ala Asn Ala Lys Trp Phe
                325                 330                 335

Thr Phe Trp Val Ser Ala Tyr Leu Gln Gln Cys Asn Pro Ser Gly Ile
            340                 345                 350

Gln Ala Gly Thr Val Ser Pro Ser Thr Ala Thr Leu Thr Asp Phe Glu
            355                 360                 365

Pro Met Ala Asn Arg Ser Val Thr Ser Pro Trp Thr Tyr Ser Ala Asn
370                 375                 380

Gly Tyr Tyr Glu Pro Ser Ile Gly Glu Phe Gln Val Phe Ser Pro Val
385                 390                 395                 400

Val Thr Gly Ala Trp Asn Pro Gly Asn Ile Gly Ile Arg Val Leu Pro
                405                 410                 415

Val Pro Val Ser Ala Ser Gly Glu Arg Tyr Thr Leu Leu Cys Tyr Ser
            420                 425                 430

Leu Gln Cys Thr Asn Ala Ser Ile Phe Asn Pro Asn Asn Ser Gly Thr
            435                 440                 445

<210> SEQ ID NO 17
<211> LENGTH: 446
<212> TYPE: PRT
<213> ORGANISM: Fowl adenovirus C

<400> SEQUENCE: 17

Glu Ala Gly Pro Ser Pro Ala Pro Ile Lys Arg Ala Lys Arg Met Val
1               5                   10                  15

Arg Ala Ser Gln Leu Asp Leu Val Tyr Pro Phe Asp Tyr Val Ala Asp
            20                  25                  30

Pro Val Gly Gly Leu Asn Pro Pro Phe Leu Gly Gly Ser Gly Pro Leu
        35                  40                  45

Val Asp Gln Gly Gly Gln Leu Thr Leu Asn Val Thr Asp Pro Ile Ile
50                  55                  60

Ile Lys Asn Arg Ser Val Asp Leu Ala His Asp Pro Ser Leu Asp Val
65                  70                  75                  80

Asn Ala Gln Gly Gln Leu Ala Val Ala Val Asp Pro Glu Gly Ala Leu
                85                  90                  95

Asp Ile Thr Pro Asp Gly Leu Asp Val Lys Val Asp Gly Val Thr Val
            100                 105                 110

Met Val Asn Asp Asp Trp Glu Leu Ala Val Lys Val Asp Pro Ser Gly
        115                 120                 125

Gly Leu Asp Ser Thr Ala Gly Gly Leu Gly Val Ser Val Asp Asp Thr
130                 135                 140

Leu Leu Val Asp Gln Gly Glu Leu Gly Val His Leu Asn Gln Gln Gly
145                 150                 155                 160

Pro Ile Thr Ala Asp Ser Ser Gly Ile Asp Leu Glu Ile Asn Pro Asn
                165                 170                 175

Met Phe Thr Val Asn Thr Ser Thr Gly Ser Gly Val Leu Glu Leu Asn
            180                 185                 190

Leu Lys Ala Gln Gly Gly Ile Gln Ala Asp Ser Ser Gly Val Gly Val

```
            195                 200                 205
Ser Val Asp Glu Ser Leu Gln Ile Val Asn Asn Thr Leu Glu Val Lys
    210                 215                 220

Pro Asp Pro Ser Gly Pro Leu Thr Val Ser Ala Asn Gly Leu Gly Leu
225                 230                 235                 240

Lys Tyr Asp Thr Asn Thr Leu Ala Val Thr Ala Gly Ala Leu Thr Val
                245                 250                 255

Val Gly Gly Gly Ser Val Ser Thr Pro Ile Ala Thr Phe Val Ser Gly
            260                 265                 270

Ser Pro Ser Leu Asn Thr Tyr Asn Ala Thr Thr Val Asn Ser Ser Ala
        275                 280                 285

Asn Ala Phe Ser Cys Ala Tyr Tyr Leu Gln Gln Trp Asn Ile Gln Gly
    290                 295                 300

Leu Leu Val Thr Ser Leu Tyr Leu Lys Leu Asp Ser Ala Thr Met Gly
305                 310                 315                 320

Asn Arg Pro Gly Asp Leu Asn Ser Ala Asn Ala Lys Trp Phe Thr Phe
                325                 330                 335

Trp Val Ser Ala Tyr Leu Gln Gln Cys Asn Pro Ser Gly Ile Gln Ala
            340                 345                 350

Gly Thr Val Ser Pro Ser Thr Ala Thr Leu Thr Asp Phe Glu Pro Met
        355                 360                 365

Ala Asn Arg Ser Val Thr Ser Pro Trp Thr Tyr Ser Ala Asn Gly Tyr
    370                 375                 380

Tyr Glu Pro Ser Ile Gly Glu Phe Gln Val Phe Ser Pro Val Val Thr
385                 390                 395                 400

Gly Ala Trp Asn Pro Gly Asn Ile Gly Ile Arg Val Leu Pro Val Pro
                405                 410                 415

Val Ser Ala Ser Gly Glu Arg Tyr Thr Leu Leu Cys Tyr Ser Leu Gln
            420                 425                 430

Cys Thr Asn Ala Ser Ile Phe Asn Pro Asn Asn Ser Gly Thr
        435                 440                 445

<210> SEQ ID NO 18
<211> LENGTH: 479
<212> TYPE: PRT
<213> ORGANISM: Fowl adenovirus C

<400> SEQUENCE: 18

Met Leu Arg Ala Pro Lys Arg Arg His Ser Glu Asn Gly Gln Pro Glu
1               5                   10                  15

Ser Glu Ala Gly Pro Ser Pro Ala Pro Ile Lys Arg Ala Lys Arg Met
            20                  25                  30

Val Arg Ala Ser Gln Leu Asp Leu Val Tyr Pro Phe Asp Tyr Val Ala
        35                  40                  45

Asp Pro Val Gly Gly Leu Asn Pro Pro Phe Leu Gly Ser Gly Pro
50                  55                  60

Leu Val Asp Gln Gly Gly Gln Leu Thr Leu Asn Val Thr Asp Pro Ile
65                  70                  75                  80

Ile Ile Lys Asn Arg Ser Val Asp Leu Ala His Asp Pro Ser Leu Asp
                85                  90                  95

Val Asn Ala Gln Gly Gln Leu Ala Val Ala Val Asp Pro Glu Gly Ala
            100                 105                 110

Leu Asp Ile Thr Pro Asp Gly Leu Asp Val Lys Val Asp Gly Val Thr
        115                 120                 125
```

```
Val Met Val Asn Asp Asp Trp Glu Leu Ala Val Lys Val Asp Pro Ser
    130                 135                 140

Gly Gly Leu Asp Ser Thr Ala Gly Gly Leu Gly Val Ser Val Asp Asp
145                 150                 155                 160

Thr Leu Leu Val Asp Gln Gly Glu Leu Gly Val His Leu Asn Gln Gln
                165                 170                 175

Gly Pro Ile Thr Ala Asp Ser Ser Gly Ile Asp Leu Glu Ile Asn Pro
            180                 185                 190

Asn Met Phe Thr Val Asn Thr Ser Thr Gly Ser Gly Val Leu Glu Leu
        195                 200                 205

Asn Leu Lys Ala Gln Gly Gly Ile Gln Ala Gly Ser Ser Gly Val Gly
    210                 215                 220

Val Ser Val Asp Glu Ser Leu Glu Ile Val Asn Asn Thr Leu Glu Val
225                 230                 235                 240

Lys Pro Asp Pro Ser Gly Pro Leu Thr Val Ser Ala Asn Gly Leu Gly
                245                 250                 255

Leu Lys Tyr Asp Asn Asn Thr Leu Ala Val Thr Ala Gly Ala Leu Thr
                260                 265                 270

Val Val Gly Gly Gly Ser Ile Ser Thr Pro Ile Ala Thr Phe Val Ser
            275                 280                 285

Gly Ser Ala Ser Leu Asn Ala Tyr Asn Ala Arg Met Val Asn Ser Ser
        290                 295                 300

Ala His Ala Phe Ser Cys Ala Tyr Tyr Leu Gln Gln Trp Asn Ile Gln
305                 310                 315                 320

Gly Leu Leu Phe Thr Ser Leu Tyr Leu Lys Leu Asp Ser Ala Thr Met
                325                 330                 335

Gly Asn Arg Pro Gly Asp Asn Asn Ser Val Asn Ala Lys Trp Phe Thr
                340                 345                 350

Phe Trp Val Ser Ala Tyr Leu Gln Gln Cys Asn Pro Ser Gly Ile Gln
            355                 360                 365

Ala Gly Thr Val Ser Pro Ser Thr Ala Thr Leu Ala Asp Phe Glu Pro
    370                 375                 380

Met Ala Asn Arg Ser Val Ser Ser Pro Trp Thr Tyr Ser Ala Asn Gly
385                 390                 395                 400

Tyr Tyr Gln Pro Pro Ser Gly Glu Phe Gln Leu Phe Thr Pro Val Val
                405                 410                 415

Thr Gly Ala Trp Thr Pro Gly Asn Ile Gly Ile Arg Val Leu Pro Val
                420                 425                 430

Pro Val Ser Ala Ser Gly Asp Arg Tyr Thr Leu Leu Cys Tyr Ser Leu
    435                 440                 445

Gln Cys Thr Asn Ala Ser Ile Phe Asn Pro Asn Asn Ser Gly Thr Met
450                 455                 460

Ile Val Gly Pro Val Leu Tyr Ser Cys Pro Ala Gly Ser Leu Pro
465                 470                 475

<210> SEQ ID NO 19
<211> LENGTH: 479
<212> TYPE: PRT
<213> ORGANISM: Fowl adenovirus C

<400> SEQUENCE: 19

Met Leu Arg Ala Pro Lys Arg Arg His Ser Glu Asn Gly Lys Pro Glu
1               5                   10                  15

Thr Glu Ala Gly Pro Ser Pro Ala Pro Ile Lys Arg Ala Lys Arg Met
            20                  25                  30
```

```
Val Arg Ala Ser Gln Leu Asp Leu Val Tyr Pro Phe Asp Tyr Val Ala
        35                  40                  45

Asp Pro Val Gly Gly Leu Asn Pro Pro Phe Leu Gly Gly Ser Gly Pro
 50                  55                  60

Leu Val Asp Gln Gly Gly Gln Leu Thr Leu Asn Val Thr Asp Pro Ile
 65                  70                  75                  80

Ile Ile Lys Asn Arg Ser Val Asp Leu Ala Arg Asp Pro Ser Leu Asp
                 85                  90                  95

Val Asn Ala Gln Gly Gln Leu Ala Val Ala Val Asp Pro Glu Gly Ala
                100                 105                 110

Leu Ala Ile Thr Pro Asp Gly Leu Asp Val Lys Val Asp Gly Val Thr
            115                 120                 125

Val Met Val Asn Asp Asp Trp Glu Leu Ala Val Lys Val Asp Pro Ala
        130                 135                 140

Gly Gly Leu Asp Ser Thr Ala Gly Gly Leu Gly Val Ser Val Asp Asp
145                 150                 155                 160

Thr Leu Leu Val Asp Gln Gly Glu Leu Gly Val His Leu Asn Gln Gln
                165                 170                 175

Gly Pro Ile Thr Ala Asp Ser Ser Gly Ile Asp Leu Glu Ile Asn Pro
            180                 185                 190

Asn Met Phe Thr Val Asn Thr Ser Thr Gly Ser Gly Val Leu Glu Leu
        195                 200                 205

Asn Leu Lys Ala Gln Gly Gly Ile Gln Ala Gly Ser Ser Gly Val Gly
210                 215                 220

Val Ser Val Asp Glu Ser Leu Glu Ile Val Asn Asn Thr Leu Glu Val
225                 230                 235                 240

Lys Pro Asp Pro Ser Gly Pro Leu Thr Val Ser Ala Asn Gly Leu Gly
                245                 250                 255

Leu Lys Tyr Asp Asn Asn Thr Leu Ala Val Thr Ala Gly Ala Leu Thr
            260                 265                 270

Val Val Gly Gly Gly Ser Val Ser Thr Pro Ile Ala Thr Phe Val Ser
        275                 280                 285

Gly Ser Pro Ser Leu Asp Ala Tyr Asn Ala Thr Val Asn Ser Ser
290                 295                 300

Ala His Pro Phe Ser Cys Ala Tyr Tyr Leu Gln Gln Trp Asn Val Gln
305                 310                 315                 320

Gly Leu Leu Phe Thr Ser Leu Tyr Leu Lys Leu Asp Ser Thr Thr Met
                325                 330                 335

Gly Thr Arg Pro Gly Asp Trp Asn Ser Val Asn Ala Lys Trp Phe Thr
            340                 345                 350

Phe Trp Val Ser Ala Tyr Leu Gln Gln Cys Asn Pro Ser Gly Ile Gln
        355                 360                 365

Ala Gly Thr Leu Ser Pro Ser Thr Ala Thr Leu Ala Asp Phe Glu Pro
370                 375                 380

Met Ala Asn Arg Ser Val Ser Ser Pro Trp Thr Tyr Ser Ala Asn Ala
385                 390                 395                 400

Tyr Tyr Glu Pro Ser Ser Gly Glu Phe Gln Thr Phe Thr Pro Val Val
                405                 410                 415

Thr Gly Ala Trp Asn Pro Gly Asn Ile Gly Ile Arg Val Leu Pro Val
            420                 425                 430

Ser Val Ser Ala Ser Gly Asp Arg Tyr Thr Leu Leu Cys Tyr Ser Leu
        435                 440                 445
```

Gln Cys Thr Asn Ala Ser Ile Phe Asn Pro Ala Asn Ser Gly Thr Met
            450                 455                 460

Ile Val Gly Pro Val Leu Tyr Ser Cys Pro Ala Gly Ser Leu Pro
465                 470                 475

<210> SEQ ID NO 20
<211> LENGTH: 479
<212> TYPE: PRT
<213> ORGANISM: Fowl adenovirus C

<400> SEQUENCE: 20

Met Leu Arg Ala Pro Lys Arg Arg His Ser Glu Asn Gly Lys Pro Glu
1               5                   10                  15

Thr Glu Ala Gly Pro Ser Pro Ala Pro Ile Lys Arg Ala Lys Arg Met
            20                  25                  30

Val Arg Ala Ser Gln Leu Asp Leu Val Tyr Pro Phe Asp Tyr Val Ala
        35                  40                  45

Asp Pro Val Gly Gly Leu Asn Pro Pro Phe Leu Gly Gly Ser Gly Pro
    50                  55                  60

Leu Val Asp Gln Gly Gly Gln Leu Thr Leu Asn Val Thr Asp Pro Ile
65                  70                  75                  80

Ile Ile Lys Asn Arg Ser Val Asp Leu Ala Arg Asp Pro Ser Leu Asp
                85                  90                  95

Val Asn Ala Gln Gly Gln Leu Ala Val Ala Val Asp Pro Glu Gly Ala
            100                 105                 110

Leu Ala Ile Thr Pro Asp Gly Leu Asp Val Lys Val Asp Gly Val Thr
        115                 120                 125

Val Met Val Asn Asp Asp Trp Glu Leu Ala Val Lys Val Asp Pro Ala
130                 135                 140

Gly Gly Leu Asp Ser Thr Ala Gly Gly Leu Gly Val Ser Val Asp Asp
145                 150                 155                 160

Thr Leu Leu Val Asp Gln Gly Glu Leu Gly Val His Leu Asn Gln Gln
                165                 170                 175

Gly Pro Ile Thr Ala Asp Ser Ser Gly Ile Asp Leu Glu Ile Asn Pro
            180                 185                 190

Asn Met Phe Thr Val Asn Thr Ser Thr Gly Ser Gly Val Leu Glu Leu
        195                 200                 205

Asn Leu Lys Ala Gln Gly Gly Ile Gln Ala Gly Ser Ser Gly Val Gly
    210                 215                 220

Val Ser Val Asp Glu Ser Leu Glu Ile Val Asn Asn Thr Leu Glu Val
225                 230                 235                 240

Lys Pro Asp Pro Ser Gly Pro Leu Thr Val Ser Ala Asn Gly Leu Gly
                245                 250                 255

Leu Lys Tyr Asp Asn Asn Thr Leu Ala Val Thr Ala Gly Ala Leu Thr
            260                 265                 270

Val Val Gly Gly Gly Ser Val Ser Thr Pro Ile Ala Thr Phe Val Ser
        275                 280                 285

Gly Ser Pro Ser Leu Asp Ala Tyr Asn Ala Thr Thr Val Asn Ser Ser
    290                 295                 300

Ala His Pro Phe Ser Cys Ala Tyr Tyr Leu Gln Gln Trp Asn Val Gln
305                 310                 315                 320

Gly Leu Leu Phe Thr Ser Leu Tyr Leu Lys Leu Asp Ser Thr Thr Met
                325                 330                 335

Gly Thr Arg Pro Gly Asp Trp Asn Ser Val Asn Ala Lys Trp Phe Thr
            340                 345                 350

```
Phe Trp Val Ser Ala Tyr Leu Gln Gln Cys Asn Pro Ser Gly Ile Gln
            355                 360                 365

Ala Gly Thr Leu Ser Pro Ser Thr Ala Thr Leu Ala Asp Phe Glu Pro
        370                 375                 380

Met Ala Asn Arg Ser Val Ser Ser Pro Trp Thr Tyr Ser Ala Asn Ala
385                 390                 395                 400

Tyr Tyr Glu Pro Ser Ser Gly Glu Phe Gln Thr Phe Thr Pro Val Val
                405                 410                 415

Thr Gly Ala Trp Asn Pro Gly Asn Ile Gly Ile Arg Val Leu Pro Val
            420                 425                 430

Ser Val Ser Ala Ser Gly Asp Arg Tyr Thr Leu Leu Cys Tyr Ser Leu
        435                 440                 445

Gln Cys Thr Asn Ala Ser Ile Phe Asn Pro Ala Asn Ser Gly Thr Met
    450                 455                 460

Ile Val Gly Pro Val Leu Tyr Ser Cys Pro Ala Gly Ser Leu Pro
465                 470                 475

<210> SEQ ID NO 21
<211> LENGTH: 442
<212> TYPE: PRT
<213> ORGANISM: Fowl adenovirus C

<400> SEQUENCE: 21

Ser Pro Ala Pro Ile Lys Arg Pro Lys Arg Met Val Arg Ala Ser Gln
1               5                   10                  15

Leu Asp Leu Val Tyr Pro Phe Asp Tyr Val Ala Asp Pro Val Gly Gly
            20                  25                  30

Leu Asn Pro Pro Phe Leu Gly Gly Ser Gly Pro Leu Val Asp Gln Gly
        35                  40                  45

Gly Gln Leu Thr Leu Asn Val Thr Asp Pro Ile Ile Ile Lys Asn Arg
    50                  55                  60

Ser Val Asp Leu Ala His Asp Pro Ser Leu Asp Val Asn Ala Gln Gly
65                  70                  75                  80

Gln Leu Ala Val Ala Val Asp Pro Glu Gly Ala Leu Ala Ile Thr Pro
                85                  90                  95

Asp Gly Leu Asp Val Lys Val Asp Gly Val Thr Val Met Val Asn Asp
            100                 105                 110

Asp Trp Glu Leu Ala Val Lys Val Asp Pro Ala Gly Gly Leu Asp Ser
        115                 120                 125

Thr Ala Gly Gly Leu Gly Val Ser Val Asp Asp Thr Leu Leu Val Asp
    130                 135                 140

Gln Gly Glu Leu Gly Val His Leu Asn Gln Gln Gly Pro Ile Thr Ala
145                 150                 155                 160

Asp Ser Ser Gly Ile Asp Leu Glu Ile Asn Pro Asn Met Phe Thr Val
                165                 170                 175

Asn Thr Ser Thr Gly Ser Gly Val Leu Glu Leu Asn Leu Lys Ala Gln
            180                 185                 190

Gly Gly Ile Gln Ala Gly Ser Ser Gly Val Gly Val Ser Val Asp Glu
        195                 200                 205

Ser Leu Glu Ile Val Asn Asn Thr Leu Glu Val Lys Pro Asp Pro Thr
    210                 215                 220

Gly Pro Leu Thr Val Ser Ala Asn Gly Leu Gly Leu Lys Tyr Asp Asn
225                 230                 235                 240

Asn Thr Leu Ala Val Thr Ala Gly Ala Leu Thr Val Val Gly Gly Gly
```

```
                        245                 250                 255
Ser Val Ser Thr Pro Ile Ala Thr Phe Val Ser Gly Ser Pro Ser Leu
                    260                 265                 270

Asp Ala Tyr Asn Ala Arg Met Val Asn Ser Ser Ala His Pro Phe Ser
                275                 280                 285

Cys Ala Tyr Tyr Leu Gln Gln Trp Asn Val Gln Gly Leu Leu Phe Thr
            290                 295                 300

Ser Leu Tyr Leu Lys Leu Asp Ser Thr Thr Met Gly Asn Arg Pro Gly
305                 310                 315                 320

Asp Trp Asn Ser Val Asn Ala Lys Trp Phe Thr Phe Trp Val Ser Ala
                325                 330                 335

Tyr Leu Gln Gln Cys Asn Pro Ser Gly Ile Gln Ala Gly Thr Leu Ser
                340                 345                 350

Pro Ser Thr Ala Thr Leu Ala Asp Phe Glu Pro Met Ala Asn Arg Ser
                355                 360                 365

Val Ser Ser Pro Trp Thr Tyr Ser Ala Asn Ala Tyr Tyr Glu Pro Ser
            370                 375                 380

Ser Gly Glu Phe Gln Thr Phe Thr Pro Val Val Thr Gly Ala Trp Asn
385                 390                 395                 400

Pro Gly Asn Ile Gly Ile Arg Val Leu Pro Val Ser Val Ser Ala Ser
                405                 410                 415

Gly Glu Arg Tyr Thr Leu Leu Cys Tyr Ser Leu Gln Cys Thr Asn Ala
                420                 425                 430

Ser Ile Phe Asn Pro Ala Asn Ser Gly Thr
                435                 440

<210> SEQ ID NO 22
<211> LENGTH: 476
<212> TYPE: PRT
<213> ORGANISM: Fowl adenovirus C

<400> SEQUENCE: 22

Arg Ala Pro Lys Arg Arg His Ser Glu Asn Gly Gln Pro Glu Ser Glu
1               5                   10                  15

Ala Gly Pro Ser Pro Ala Pro Ile Lys Arg Ala Lys Arg Met Val Arg
                20                  25                  30

Ala Ser Gln Leu Asp Leu Val Tyr Pro Phe Asp Tyr Val Ala Asp Pro
            35                  40                  45

Val Gly Gly Leu Asn Pro Pro Phe Leu Gly Gly Ser Gly Pro Leu Val
        50                  55                  60

Asp Gln Gly Gly Gln Leu Thr Leu Asn Val Thr Asp Pro Ile Ile Ile
65                  70                  75                  80

Lys Asn Arg Ser Val Asp Leu Ala His Asp Pro Ser Leu Asp Val Asn
                85                  90                  95

Ala Gln Gly Gln Leu Ala Val Ala Val Asp Pro Glu Gly Ala Leu Asp
            100                 105                 110

Ile Thr Pro Asp Gly Leu Asp Val Lys Val Asp Gly Val Thr Val Met
        115                 120                 125

Val Asn Asp Asp Trp Glu Leu Ala Val Lys Val Asp Pro Ser Gly Gly
    130                 135                 140

Leu Asp Ser Thr Ala Gly Gly Leu Gly Val Ser Val Asp Asp Thr Leu
145                 150                 155                 160

Leu Val Asp Gln Gly Glu Leu Gly Val His Leu Asn Gln Gln Gly Pro
                165                 170                 175
```

```
Ile Thr Ala Asp Ser Ser Gly Ile Asp Leu Glu Ile Asn Pro Asn Met
            180                 185                 190

Phe Thr Val Asn Thr Ser Thr Gly Ser Gly Val Leu Glu Leu Asn Leu
        195                 200                 205

Lys Ala Gln Gly Gly Ile Gln Ala Gly Ser Ser Gly Val Gly Val Ser
    210                 215                 220

Val Asp Glu Ser Leu Glu Ile Val Asn Asn Thr Leu Glu Val Lys Pro
225                 230                 235                 240

Asp Pro Ser Gly Pro Leu Thr Val Ser Ala Asn Gly Leu Gly Leu Lys
                245                 250                 255

Tyr Asp Ser Asn Thr Leu Ala Val Thr Ala Gly Ala Leu Thr Val Val
            260                 265                 270

Gly Gly Gly Ser Val Ser Thr Pro Ile Ala Thr Phe Val Ser Gly Ser
        275                 280                 285

Pro Ser Leu Asn Thr Tyr Asn Ala Thr Ile Val Asn Ser Ser Ser His
    290                 295                 300

Pro Phe Ser Cys Ala Tyr Tyr Leu Gln Gln Trp Asn Val Gln Gly Leu
305                 310                 315                 320

Leu Phe Thr Ser Leu Tyr Val Lys Leu Asp Ser Thr Thr Met Gly Thr
                325                 330                 335

Arg Pro Gly Asp Asn Ser Ser Ala Asn Ala Lys Trp Phe Thr Phe Trp
            340                 345                 350

Val Ser Ala Tyr Leu Gln Gln Cys Asn Pro Ser Gly Ile Gln Ala Gly
        355                 360                 365

Thr Val Ser Pro Ser Thr Ala Ala Leu Ala Asp Phe Glu Pro Met Ala
    370                 375                 380

Asn Arg Ser Val Ser Ser Pro Trp Thr Tyr Ser Ala Asn Ala Tyr Tyr
385                 390                 395                 400

Gln Pro Ser Ser Gly Glu Phe Gln Val Phe Thr Pro Val Val Thr Gly
                405                 410                 415

Ala Trp Asn Pro Gly Asn Ile Gly Ile Arg Val Leu Pro Val Pro Val
            420                 425                 430

Thr Ala Ser Gly Asp Arg Tyr Thr Leu Leu Cys Tyr Ser Leu Gln Cys
        435                 440                 445

Thr Asn Ser Ser Ile Phe Asn Pro Ala Asn Ser Gly Thr Met Ile Val
    450                 455                 460

Gly Pro Val Leu Tyr Ser Cys Pro Ala Ala Ser Val
465                 470                 475

<210> SEQ ID NO 23
<211> LENGTH: 479
<212> TYPE: PRT
<213> ORGANISM: Fowl adenovirus C

<400> SEQUENCE: 23

Met Leu Arg Ala Pro Lys Arg Arg His Ser Glu Asn Gly Gln Pro Glu
1               5                   10                  15

Ser Glu Ala Gly Pro Ser Pro Ala Pro Ile Lys Arg Ala Lys Arg Met
            20                  25                  30

Val Arg Ala Ser Gln Leu Asp Leu Val Tyr Pro Phe Asp Tyr Val Ala
        35                  40                  45

Asp Pro Val Gly Gly Leu Asn Pro Pro Phe Leu Gly Gly Ser Gly Pro
    50                  55                  60

Leu Val Asp Gln Gly Gly Gln Leu Thr Leu Asn Val Thr Asp Pro Ile
65                  70                  75                  80
```

Ile Ile Lys Asn Arg Ser Val Asp Leu Ala His Asp Pro Ser Leu Asp
            85                  90                  95

Val Asn Ala Gln Gly Gln Leu Ala Val Ala Val Asp Pro Glu Gly Ala
        100                 105                 110

Leu Asp Ile Thr Pro Asp Gly Leu Asp Val Lys Val Asp Gly Val Thr
        115                 120                 125

Val Met Val Asn Asp Asp Trp Glu Leu Ala Val Lys Val Asp Pro Ser
    130                 135                 140

Gly Gly Leu Asp Ser Thr Ala Gly Gly Leu Gly Val Ser Val Asp Asp
145                 150                 155                 160

Thr Leu Leu Val Asp Gln Gly Glu Leu Gly Val His Leu Asn Gln Gln
                165                 170                 175

Gly Pro Ile Thr Ala Asp Ser Ser Gly Ile Asp Leu Glu Ile Asn Pro
            180                 185                 190

Asn Met Phe Thr Val Asn Thr Ser Thr Gly Ser Gly Val Leu Glu Leu
        195                 200                 205

Asn Leu Lys Ala Gln Gly Gly Ile Gln Ala Gly Ser Ser Gly Val Gly
    210                 215                 220

Val Ser Val Asp Glu Ser Leu Glu Ile Val Asn Asn Thr Leu Glu Val
225                 230                 235                 240

Lys Pro Asp Pro Ser Gly Pro Leu Thr Val Ser Ala Asn Gly Leu Gly
                245                 250                 255

Leu Lys Tyr Asp Ser Asn Thr Leu Ala Val Thr Ala Gly Ala Leu Thr
            260                 265                 270

Val Val Gly Gly Gly Ser Val Ser Thr Pro Ile Ala Thr Phe Val Ser
        275                 280                 285

Gly Ser Pro Ser Leu Asn Thr Tyr Asn Ala Thr Ile Val Asn Ser Ser
    290                 295                 300

Ser His Pro Phe Ser Cys Ala Tyr Tyr Leu Gln Gln Trp Asn Val Gln
305                 310                 315                 320

Gly Leu Leu Phe Thr Ser Leu Tyr Val Lys Leu Asp Ser Thr Thr Met
                325                 330                 335

Gly Thr Arg Pro Gly Asp Asn Ser Ser Ala Asn Ala Lys Trp Phe Thr
            340                 345                 350

Phe Trp Val Ser Ala Tyr Leu Gln Gln Cys Asn Pro Ser Gly Ile Gln
        355                 360                 365

Ala Gly Thr Val Ser Pro Ser Thr Ala Ala Leu Ala Asp Phe Glu Pro
    370                 375                 380

Met Ala Asn Arg Ser Val Ser Ser Pro Trp Thr Tyr Ser Ala Asn Ala
385                 390                 395                 400

Tyr Tyr Gln Pro Ser Ser Gly Glu Phe Gln Val Phe Thr Pro Val Val
                405                 410                 415

Thr Gly Ala Trp Asn Pro Gly Asn Ile Gly Ile Arg Val Leu Pro Val
            420                 425                 430

Pro Val Thr Ala Ser Gly Asp Arg Tyr Thr Leu Leu Cys Tyr Ser Leu
        435                 440                 445

Gln Cys Thr Asn Ser Ser Ile Phe Asn Pro Ala Asn Ser Gly Thr Met
    450                 455                 460

Ile Val Gly Pro Val Leu Tyr Ser Cys Pro Ala Ala Ser Val Pro
465                 470                 475

<210> SEQ ID NO 24
<211> LENGTH: 474

<212> TYPE: PRT
<213> ORGANISM: Fowl adenovirus C

<400> SEQUENCE: 24

```
Met Leu Arg Ala Pro Lys Arg Arg His Ser Glu Thr Glu Ala Gly Pro
1               5                   10                  15

Ser Pro Ala Pro Ile Lys Arg Pro Lys Arg Met Val Arg Ala Ser Gln
            20                  25                  30

Leu Asp Leu Val Tyr Pro Phe Asp Tyr Val Ala Asp Pro Val Gly Gly
        35                  40                  45

Leu Asn Pro Pro Phe Leu Gly Gly Ser Gly Pro Leu Val Asp Gln Gly
    50                  55                  60

Gly Gln Leu Thr Leu Asn Val Thr Asp Pro Ile Ile Lys Asn Arg
65                  70                  75                  80

Ser Val Asp Leu Ala His Asp Pro Ser Leu Asp Val Asn Ala Gln Gly
                85                  90                  95

Gln Leu Ala Val Ala Val Asp Pro Glu Gly Ala Leu Asp Ile Thr Pro
            100                 105                 110

Asp Gly Leu Asp Val Lys Val Asp Gly Val Thr Val Met Val Asn Asp
        115                 120                 125

Asp Trp Glu Leu Ala Val Lys Val Asp Pro Ser Gly Gly Leu Asp Ser
    130                 135                 140

Thr Ala Gly Gly Leu Gly Val Ser Val Asp Asp Thr Leu Leu Val Asp
145                 150                 155                 160

Gln Gly Glu Leu Gly Val His Leu Asn Gln Gln Gly Pro Ile Thr Ala
                165                 170                 175

Asp Ser Ser Gly Ile Asp Leu Glu Ile Asn Pro Asn Met Phe Thr Val
            180                 185                 190

Asn Thr Ser Thr Gly Ser Gly Val Leu Glu Leu Asn Leu Lys Ala Gln
        195                 200                 205

Gly Gly Ile Gln Ala Gly Ser Ser Gly Val Gly Val Ser Val Asp Glu
    210                 215                 220

Ser Leu Glu Ile Val Asn Asn Thr Leu Glu Val Lys Pro Asp Pro Ser
225                 230                 235                 240

Gly Pro Leu Thr Val Ser Ala Asn Gly Leu Gly Leu Lys Tyr Asp Ser
                245                 250                 255

Asn Thr Leu Ala Val Thr Ala Gly Ala Leu Thr Val Val Gly Gly Gly
            260                 265                 270

Ser Val Ser Thr Pro Ile Ala Thr Phe Val Ser Gly Ser Pro Ser Leu
        275                 280                 285

Asn Thr Tyr Asn Ala Thr Ile Val Asn Ser Ser His Pro Phe Ser
    290                 295                 300

Cys Ala Tyr Tyr Leu Gln Gln Trp Asn Val Gln Gly Leu Leu Phe Thr
305                 310                 315                 320

Ser Leu Tyr Val Lys Leu Asp Ser Thr Thr Met Gly Thr Arg Pro Gly
                325                 330                 335

Asp Asn Ser Ser Ala Asn Ala Lys Trp Phe Thr Phe Trp Val Ser Ala
            340                 345                 350

Tyr Leu Gln Gln Cys Asn Pro Ser Gly Ile Gln Ala Gly Thr Val Ser
        355                 360                 365

Pro Ser Thr Ala Ala Leu Ala Asp Phe Glu Pro Met Ala Asn Arg Ser
    370                 375                 380

Val Ser Ser Pro Trp Thr Tyr Ser Ala Asn Ala Tyr Tyr Gln Pro Pro
385                 390                 395                 400
```

```
Ser Gly Glu Phe Gln Val Phe Thr Pro Val Thr Gly Ala Trp Asn
                405                 410                 415

Pro Gly Asn Ile Gly Ile Arg Val Leu Pro Val Pro Val Thr Ala Ser
            420                 425                 430

Gly Asp Arg Tyr Thr Leu Leu Cys Tyr Ser Leu Gln Cys Thr Asn Ser
            435                 440                 445

Ser Ile Phe Asn Pro Ala Asn Ser Gly Thr Met Ile Val Gly Pro Val
450                 455                 460

Leu Tyr Ser Cys Pro Ala Ala Ser Val Pro
465                 470

<210> SEQ ID NO 25
<211> LENGTH: 479
<212> TYPE: PRT
<213> ORGANISM: Fowl adenovirus C

<400> SEQUENCE: 25

Met Leu Arg Ala Pro Lys Arg Arg His Ser Glu Asn Gly Gln Pro Glu
1               5                   10                  15

Ser Glu Ala Gly Pro Ser Pro Ala Pro Ile Lys Arg Ala Lys Arg Met
            20                  25                  30

Val Arg Ala Ala Gln Leu Asp Leu Val Tyr Pro Phe Asp Tyr Val Ala
        35                  40                  45

Asp Pro Val Gly Gly Leu Asn Pro Pro Phe Leu Gly Gly Ser Gly Pro
    50                  55                  60

Leu Val Asp Gln Gly Gly Gln Leu Thr Leu Asn Val Thr Asp Pro Ile
65                  70                  75                  80

Ile Ile Lys Asn Arg Ser Val Asp Leu Ala His Asp Pro Ser Leu Asp
                85                  90                  95

Val Asn Ala Gln Gly Gln Leu Ala Val Ala Val Asp Pro Glu Gly Ala
            100                 105                 110

Leu Asp Ile Thr Pro Asp Gly Leu Asp Val Lys Val Asp Gly Val Thr
        115                 120                 125

Val Met Val Asn Asp Asp Trp Glu Leu Ala Val Lys Val Asp Pro Ser
130                 135                 140

Gly Gly Leu Asp Ser Thr Ala Gly Gly Leu Gly Val Ser Val Asp Asp
145                 150                 155                 160

Thr Leu Leu Val Asp Gln Gly Glu Leu Gly Val His Leu Asn Gln Gln
                165                 170                 175

Gly Pro Ile Thr Ala Asp Ser Ser Gly Ile Asp Leu Glu Ile Asn Pro
            180                 185                 190

Asn Met Phe Thr Val Asn Thr Ser Thr Gly Ser Gly Val Leu Glu Leu
        195                 200                 205

Asn Leu Lys Ala Gln Gly Gly Ile Gln Ala Gly Ser Ser Gly Val Gly
    210                 215                 220

Val Ser Val Asp Glu Ser Leu Glu Ile Val Asn Asn Thr Leu Glu Val
225                 230                 235                 240

Lys Pro Asp Pro Ser Gly Pro Leu Thr Val Ser Ala Asn Gly Leu Gly
                245                 250                 255

Leu Lys Tyr Asp Ser Asn Thr Leu Ala Val Thr Ala Gly Ala Leu Thr
            260                 265                 270

Val Val Gly Gly Gly Ser Val Ser Thr Pro Ile Ala Thr Phe Val Ser
        275                 280                 285

Gly Ser Pro Ser Leu Asn Thr Tyr Asn Ala Thr Ile Val Asn Ser Ser
```

```
            290                 295                 300
Ala His Pro Phe Ser Cys Ala Tyr Tyr Leu Gln Gln Trp Asn Val Gln
305                 310                 315                 320

Gly Leu Leu Phe Thr Ser Leu Tyr Val Lys Leu Asp Ser Thr Thr Met
                325                 330                 335

Gly Thr Arg Pro Gly Asp Asn Ser Ser Ala Asn Ala Lys Trp Phe Thr
                340                 345                 350

Phe Trp Val Ser Ala Tyr Leu Gln Gln Cys Asn Pro Ser Gly Ile Gln
            355                 360                 365

Ala Gly Thr Val Ser Pro Ser Thr Ala Ala Leu Ala Asp Phe Glu Pro
        370                 375                 380

Met Ala Asn Arg Ser Val Ser Ser Pro Trp Thr Tyr Ser Ala Asn Ala
385                 390                 395                 400

Tyr Tyr Gln Pro Ser Ser Gly Glu Phe Gln Val Phe Thr Pro Val Val
                405                 410                 415

Thr Gly Ala Trp Asn Pro Gly Asn Ile Gly Val Arg Val Leu Pro Val
                420                 425                 430

Pro Val Ser Ala Ser Gly Asp Arg Tyr Thr Leu Leu Cys Tyr Ser Leu
            435                 440                 445

Gln Cys Thr Asn Ala Ser Ile Phe Asn Pro Ala Asn Ser Gly Thr Met
        450                 455                 460

Thr Val Gly Pro Val Leu Tyr Thr Cys Pro Ala Ala Ser Val Pro
465                 470                 475

<210> SEQ ID NO 26
<211> LENGTH: 467
<212> TYPE: PRT
<213> ORGANISM: Fowl adenovirus C

<400> SEQUENCE: 26

Arg Arg His Ser Glu Thr Glu Ala Gly Pro Tyr Pro Ala Pro Ile Lys
1               5                   10                  15

Arg Pro Lys Arg Met Val Arg Ala Ser Gln Leu Asp Leu Val Tyr Pro
            20                  25                  30

Phe Asp Tyr Val Ala Asp Pro Val Gly Gly Leu Asn Pro Pro Phe Leu
        35                  40                  45

Gly Gly Ser Gly Pro Leu Val Asp Gln Gly Gly Gln Leu Thr Leu Asn
    50                  55                  60

Val Thr Asp Pro Ile Ile Ile Lys Asn Arg Ser Val Asp Leu Ala His
65                  70                  75                  80

Asp Pro Ser Leu Asp Val Asn Ala Gln Gly Gln Leu Ala Val Ala Val
                85                  90                  95

Asp Pro Glu Gly Ala Leu Ala Ile Thr Pro Asp Gly Leu Asp Val Lys
            100                 105                 110

Val Asp Gly Val Thr Val Met Val Asn Asp Asp Trp Glu Leu Ala Val
        115                 120                 125

Lys Val Asp Pro Ala Gly Gly Leu Asp Ser Thr Ala Gly Gly Leu Gly
    130                 135                 140

Val Ser Val Asp Asp Thr Leu Leu Val Asp Gln Gly Glu Leu Gly Val
145                 150                 155                 160

His Leu Asn Gln Gln Gly Pro Ile Thr Ala Asp Ser Ser Gly Ile Asp
                165                 170                 175

Leu Glu Ile Asn Pro Asn Met Phe Thr Val Asn Thr Ser Thr Gly Ser
            180                 185                 190
```

```
Gly Val Leu Glu Leu Asn Leu Lys Ala Gln Gly Gly Ile Gln Ala Arg
            195                 200                 205

Ser Ser Gly Val Gly Val Ser Val Asp Glu Ser Leu Gln Ile Val Asp
210                 215                 220

Asn Thr Leu Glu Val Lys Pro Asp Pro Ser Gly Pro Leu Thr Val Ser
225                 230                 235                 240

Ala Asn Gly Leu Gly Leu Lys Tyr Asp Asn Asn Thr Leu Ala Val Thr
            245                 250                 255

Ala Gly Ala Leu Thr Val Val Gly Gly Ser Val Ser Thr Pro Ile
            260                 265                 270

Ala Thr Phe Val Ser Gly Ser Pro Ser Leu Asn Thr Tyr Asn Ala Thr
            275                 280                 285

Thr Val Asn Ser Ser Ala His Ala Phe Ser Cys Ala Tyr Tyr Leu Gln
            290                 295                 300

Gln Trp Asn Ile Gln Gly Leu Leu Phe Thr Ser Leu Tyr Leu Lys Leu
305                 310                 315                 320

Asp Ser Thr Thr Met Gly Thr Arg Pro Gly Asp Asn Ser Ser Val Asn
                325                 330                 335

Ala Lys Trp Phe Thr Phe Trp Val Ser Ala Tyr Leu Gln Gln Cys Asn
                340                 345                 350

Pro Ser Gly Ile Gln Ala Gly Thr Val Ser Pro Ser Thr Ala Thr Leu
            355                 360                 365

Thr Asp Phe Glu Pro Met Ala Asn Arg Ser Val Ser Ser Ser Trp Thr
            370                 375                 380

Tyr Ser Ala Asn Ala Tyr Tyr Gln Pro Ser Ser Gly Glu Phe Gln Val
385                 390                 395                 400

Phe Thr Pro Val Val Thr Gly Ala Trp Asn Pro Gly Asn Ile Gly Val
                405                 410                 415

Arg Val Leu Pro Val Pro Val Ser Ala Ser Gly Asp Arg Tyr Thr Leu
                420                 425                 430

Leu Cys Tyr Ser Leu Gln Cys Thr Asn Ala Ser Ile Phe Asn Pro Ala
            435                 440                 445

Asn Ser Gly Thr Met Ile Val Gly Pro Val Leu Tyr Ser Cys Pro Ala
450                 455                 460

Ala Ser Val
465

<210> SEQ ID NO 27
<211> LENGTH: 479
<212> TYPE: PRT
<213> ORGANISM: Fowl adenovirus C

<400> SEQUENCE: 27

Met Leu Arg Ala Pro Lys Arg Arg His Ser Glu Asn Arg His Ser Glu
1               5                   10                  15

Thr Glu Ala Gly Pro Tyr Pro Ala Pro Ile Lys Arg Pro Lys Arg Met
                20                  25                  30

Val Arg Ala Ser Gln Leu Asp Leu Val Tyr Pro Phe Asp Tyr Val Ala
            35                  40                  45

Asp Pro Val Gly Gly Leu Asn Pro Pro Phe Leu Gly Gly Ser Gly Pro
        50                  55                  60

Leu Val Asp Gln Gly Gly Gln Leu Thr Leu Asn Val Thr Asp Pro Ile
65                  70                  75                  80

Ile Ile Lys Asn Arg Ser Val Asp Leu Ala His Asp Pro Ser Leu Asp
                85                  90                  95
```

Val Asn Ala Gln Gly Gln Leu Ala Val Ala Val Asp Pro Glu Gly Ala
            100                 105                 110

Leu Ala Ile Thr Pro Asp Gly Leu Asp Val Lys Val Asp Gly Val Thr
            115                 120                 125

Val Met Val Asn Asp Asp Trp Glu Leu Ala Val Lys Val Asp Pro Ala
130                 135                 140

Gly Gly Leu Asp Ser Thr Ala Gly Leu Gly Val Ser Val Asp Asp
145                 150                 155                 160

Thr Leu Leu Val Asp Gln Gly Glu Leu Gly Val His Leu Asn Gln Gln
                165                 170                 175

Gly Pro Ile Thr Ala Asp Ser Ser Gly Ile Asp Leu Glu Ile Asn Pro
            180                 185                 190

Asn Met Phe Thr Val Asn Thr Ser Thr Gly Ser Gly Val Leu Glu Leu
            195                 200                 205

Asn Leu Lys Ala Gln Gly Gly Ile Gln Ala Asp Ser Ser Gly Val Gly
            210                 215                 220

Val Ser Val Asp Glu Ser Leu Gln Ile Val Asn Asn Thr Leu Glu Val
225                 230                 235                 240

Lys Pro Asp Pro Ser Gly Pro Leu Thr Val Ser Ala Asn Gly Leu Gly
                245                 250                 255

Leu Lys Tyr Asp Asn Asn Thr Leu Ala Val Thr Ala Gly Ala Leu Thr
            260                 265                 270

Val Val Gly Gly Gly Ser Val Ser Thr Pro Ile Ala Thr Phe Val Ser
            275                 280                 285

Gly Ser Pro Ser Leu Asn Thr Tyr Asn Ala Thr Thr Val Asn Ser Ser
            290                 295                 300

Ala His Ala Phe Ser Cys Ala Tyr Tyr Leu Gln Gln Trp Asn Ile Gln
305                 310                 315                 320

Gly Leu Leu Phe Thr Ser Leu Tyr Leu Lys Leu Asp Ser Thr Thr Met
                325                 330                 335

Gly Thr Arg Pro Gly Asp Asn Ser Ser Val Asn Ala Lys Trp Phe Thr
            340                 345                 350

Phe Trp Val Ser Ala Tyr Leu Gln Gln Cys Asn Pro Ser Gly Ile Gln
            355                 360                 365

Ala Gly Thr Val Ser Pro Ser Thr Ala Thr Leu Thr Asp Phe Glu Pro
            370                 375                 380

Met Ala Asn Arg Ser Val Ser Ser Ser Trp Thr Tyr Ser Ala Asn Ala
385                 390                 395                 400

Tyr Tyr Gln Pro Ser Ser Gly Glu Phe Gln Val Phe Thr Pro Val Val
                405                 410                 415

Thr Gly Ala Trp Asn Pro Gly Asn Ile Gly Val Arg Val Leu Pro Val
            420                 425                 430

Pro Val Ser Ala Ser Gly Asp Arg Tyr Thr Leu Leu Cys Tyr Ser Leu
            435                 440                 445

Gln Cys Thr Asn Ala Ser Ile Phe Asn Pro Ala Asn Ser Gly Thr Met
            450                 455                 460

Ile Val Gly Pro Val Leu Tyr Ser Cys Pro Ala Ala Ser Val Pro
465                 470                 475

<210> SEQ ID NO 28
<211> LENGTH: 464
<212> TYPE: PRT
<213> ORGANISM: Fowl adenovirus C

<400> SEQUENCE: 28

```
Glu Thr Glu Ala Gly Pro Tyr Pro Ala Pro Ile Lys Arg Pro Lys Arg
1               5                   10                  15

Met Val Arg Ala Ser Gln Leu Asp Leu Val Tyr Pro Phe Asp Tyr Val
            20                  25                  30

Ala Asp Pro Val Gly Gly Leu Asn Pro Pro Phe Leu Gly Gly Ser Gly
        35                  40                  45

Pro Leu Val Asp Gln Gly Gln Leu Thr Leu Asn Val Thr Asp Pro
    50                  55                  60

Ile Ile Ile Lys Asn Arg Ser Val Asp Leu Ala His Asp Pro Ser Leu
65                  70                  75                  80

Asp Val Asn Ala Gln Gly Gln Leu Ala Val Ala Val Asp Pro Glu Gly
                85                  90                  95

Ala Leu Ala Ile Thr Pro Asp Gly Leu Asp Val Lys Val Asp Gly Val
            100                 105                 110

Thr Val Met Val Asn Asp Asp Trp Glu Leu Ala Val Lys Val Asp Pro
        115                 120                 125

Ala Gly Gly Leu Asp Ser Thr Ala Gly Gly Leu Gly Val Ser Val Asp
    130                 135                 140

Asp Thr Leu Leu Val Asp Gln Gly Glu Leu Gly Val His Leu Asn Gln
145                 150                 155                 160

Gln Gly Pro Ile Thr Ala Asp Ser Ser Gly Ile Asp Leu Glu Ile Asn
                165                 170                 175

Pro Asn Met Phe Thr Val Asn Thr Ser Thr Gly Ser Gly Val Leu Glu
            180                 185                 190

Leu Asn Leu Lys Ala Gln Gly Gly Ile Gln Ala Asp Ser Ser Gly Val
        195                 200                 205

Gly Val Ser Val Asp Glu Ser Leu Gln Ile Val Asn Asn Thr Leu Glu
    210                 215                 220

Val Lys Pro Asp Pro Ser Gly Pro Leu Thr Val Ser Ala Asn Gly Leu
225                 230                 235                 240

Gly Leu Lys Tyr Asp Asn Asn Thr Leu Ala Val Thr Ala Gly Ala Leu
                245                 250                 255

Thr Val Val Gly Gly Ser Val Ser Thr Pro Ile Ala Thr Phe Val
            260                 265                 270

Ser Gly Ser Pro Ser Leu Asn Thr Tyr Asn Ala Thr Thr Val Asn Ser
        275                 280                 285

Ser Ala His Ala Phe Ser Cys Ala Tyr Leu Gln Gln Trp Asn Ile
    290                 295                 300

Gln Gly Leu Leu Phe Thr Ser Leu Tyr Leu Lys Leu Asp Ser Thr Thr
305                 310                 315                 320

Met Gly Thr Arg Pro Gly Asp Asn Ser Ser Val Asn Ala Lys Trp Phe
                325                 330                 335

Thr Phe Trp Val Ser Ala Tyr Leu Gln Gln Cys Asn Pro Ser Gly Ile
            340                 345                 350

Gln Ala Gly Thr Val Ser Pro Ser Thr Ala Thr Leu Thr Asp Phe Glu
        355                 360                 365

Pro Met Ala Asn Arg Ser Val Ser Ser Trp Thr Tyr Ser Ala Asn
    370                 375                 380

Ala Tyr Tyr Gln Pro Ser Ser Gly Glu Phe Gln Val Phe Thr Pro Val
385                 390                 395                 400

Val Thr Gly Ala Trp Asn Pro Gly Asn Ile Gly Val Arg Val Leu Pro
                405                 410                 415
```

```
Val Pro Val Ser Ala Ser Gly Asp Arg Tyr Thr Leu Cys Tyr Ser
        420                 425                 430

Leu Gln Cys Thr Asn Ala Ser Ile Phe Asn Pro Ala Asn Ser Gly Thr
            435                 440                 445

Met Ile Val Gly Pro Val Leu Tyr Ser Cys Pro Ala Ala Ser Val Pro
    450                 455                 460

<210> SEQ ID NO 29
<211> LENGTH: 410
<212> TYPE: PRT
<213> ORGANISM: Fowl adenovirus C

<400> SEQUENCE: 29

Met Ala Asp Gln Lys Arg Lys Leu Ala Asp Pro Asp Ala Glu Ala Pro
1               5                   10                  15

Thr Gly Lys Met Ala Arg Ala Gly Pro Gly Glu Leu Asp Leu Val Tyr
            20                  25                  30

Pro Phe Trp Tyr Gln Val Ala Ala Pro Thr Glu Ile Thr Pro Pro Phe
        35                  40                  45

Leu Asp Pro Asn Gly Pro Leu Tyr Ser Thr Asp Gly Leu Leu Asn Val
    50                  55                  60

Arg Leu Thr Ala Pro Leu Val Ile Ile Arg Gln Ser Asn Gly Asn Ala
65                  70                  75                  80

Ile Gly Val Lys Thr Asp Gly Ser Ile Thr Val Asn Ala Asp Gly Ala
                85                  90                  95

Leu Gln Ile Gly Ile Ser Thr Ala Gly Pro Leu Thr Thr Thr Ala Asn
            100                 105                 110

Gly Ile Asp Leu Asn Ile Asp Pro Lys Thr Leu Val Val Asp Gly Ser
        115                 120                 125

Ser Gly Lys Asn Val Leu Gly Val Leu Lys Gly Gln Gly Ala Leu
    130                 135                 140

Gln Ser Ser Ala Gln Gly Ile Gly Val Ala Val Asp Glu Ser Leu Gln
145                 150                 155                 160

Ile Val Asp Asn Thr Leu Glu Val Lys Val Asp Ala Ala Gly Pro Leu
                165                 170                 175

Ala Val Thr Ala Ala Gly Val Gly Leu Gln Tyr Asp Asn Thr Gln Phe
            180                 185                 190

Lys Val Thr Asn Gly Thr Leu Gln Leu Tyr Gln Ala Pro Thr Ser Ser
        195                 200                 205

Val Ala Ala Phe Thr Ser Gly Thr Ile Gly Leu Ser Ser Pro Thr Gly
    210                 215                 220

Asn Phe Val Ser Ser Ser Asn Asn Pro Phe Asn Gly Ser Tyr Phe Leu
225                 230                 235                 240

Gln Gln Ile Asn Thr Met Gly Met Leu Thr Thr Ser Leu Tyr Val Lys
                245                 250                 255

Val Asp Thr Thr Thr Met Gly Thr Arg Pro Thr Gly Ala Val Asn Glu
            260                 265                 270

Asn Ala Arg Tyr Phe Thr Val Trp Val Ser Ser Phe Leu Thr Gln Cys
        275                 280                 285

Asn Pro Ser Asn Ile Gly Gln Gly Thr Leu Glu Pro Ser Asn Ile Ser
    290                 295                 300

Met Thr Ser Phe Glu Pro Ala Arg Asn Pro Ile Ser Pro Val Phe
305                 310                 315                 320

Asn Met Asn Gln Asn Ile Pro Tyr Tyr Ala Ser Arg Phe Gly Val Leu
```

```
                    325                 330                 335
Glu Ser Tyr Arg Pro Ile Phe Thr Gly Ser Leu Asn Thr Gly Ser Ile
                340                 345                 350

Asp Val Arg Met Gln Val Thr Pro Val Leu Ala Thr Asn Asn Thr Thr
            355                 360                 365

Tyr Asn Leu Ile Ala Phe Thr Phe Gln Cys Ala Ser Ala Gly Leu Phe
        370                 375                 380

Asn Pro Thr Val Asn Gly Thr Val Ala Ile Gly Pro Val Val His Thr
385                 390                 395                 400

Cys Pro Ala Ala Arg Ala Pro Val Thr Val
                405                 410

<210> SEQ ID NO 30
<211> LENGTH: 445
<212> TYPE: PRT
<213> ORGANISM: Fowl adenovirus C

<400> SEQUENCE: 30

Met Glu Arg Lys Arg Thr Ser Ala Ser Gly Phe Gly Ala Ala Ala Pro
1               5                   10                  15

Lys Arg Pro Arg Ala Thr Ser Ala Gln Val Asp Leu Ile Tyr Pro Phe
            20                  25                  30

Trp Tyr Gln Ala Asp Ala Pro Ser Val Asn Pro Pro Phe Leu Asp Pro
        35                  40                  45

Ser Gly Pro Leu Phe Asp Lys Asp Gly Lys Leu Ser Ile Arg Leu Gln
    50                  55                  60

Ala Pro Val Ala Glu Val Asn Lys Ser Val Gly Leu Leu Tyr Asp Gly
65                  70                  75                  80

Thr Met Gly Val Asn Asn Ala Gly Gln Leu Gly Met Arg Ile Asn Thr
                85                  90                  95

Thr Glu Gly Leu Glu Ala Thr Gly Thr Gly Leu Ala Ile Lys Thr Asp
            100                 105                 110

Leu Glu Ser Ile Gly Phe Asp Pro Thr Gly Asn Leu Gln Val Thr Leu
        115                 120                 125

Asp Pro Glu Gly Pro Ile Val Ala Ser Ala Asp Gly Leu Gln Leu Gln
    130                 135                 140

Leu Asp Gly Ala Thr Leu Glu Val Ala Asp Trp Glu Leu Gly Val Lys
145                 150                 155                 160

Leu Asp Pro Asn Glu Pro Ile Asp Ala Gly Ser Ala Gly Leu Lys Leu
                165                 170                 175

Asn Ile Asp Glu Thr Leu Leu Val Asp Ala Thr Gly Ser Gln Arg Ser
            180                 185                 190

Pro Leu Pro Asn Pro Lys Arg Pro Arg Thr His Arg Asn Gly Thr His
        195                 200                 205

Ser Gly Arg Leu Gln Arg Arg Pro Val Glu Ile Arg His His Thr Leu
    210                 215                 220

Tyr Arg His Arg Arg Ala Glu Ser Arg Arg Thr Pro Ala Asn Leu
225                 230                 235                 240

Gly Tyr Thr Ser Ile Ser Tyr Val Ser Gly Ser Thr Ser Leu Asn Ser
                245                 250                 255

Asn Thr Ala Glu Ile Val Asn Ser Ser Asn Asn Ser Phe Lys Cys Ser
            260                 265                 270

Tyr Tyr Val Lys Gln Val Asn Cys Met Gly Met Leu Phe Thr Ser Leu
        275                 280                 285
```

```
Tyr Ile Lys Leu Asp Ser Ala Thr Met Gly Thr Arg Pro Thr Gly Asn
        290                 295                 300

Thr Asn Val Asn Ala Lys Trp Phe Asn Phe Ile Val Ser Ser Tyr Leu
305                 310                 315                 320

Thr Asp Phe Asn Pro Ser Gln Met Asp Thr Gly Thr Leu Asn Pro Ala
                325                 330                 335

Val Ser Asn Gly Met Thr Tyr Met Glu Pro Ala Pro Asn Arg Thr Leu
                340                 345                 350

Pro Ser Asn Trp Asp Ala Asp Thr Asn Thr Tyr Tyr Glu Pro Ser Ser
                355                 360                 365

Gly Val Ser Gln Ser Leu Thr Ala Val Leu Thr Gly Ser Trp Ala Pro
370                 375                 380

Gly Asn Ile Thr Val Val Ala Met Pro Val Ile Ala Gln Lys Asn Gln
385                 390                 395                 400

Glu Arg Tyr Thr Val Leu Cys Phe Ser Phe Arg Cys Thr Asn Gly Gly
                405                 410                 415

Leu Phe Asn Pro Ser Val Gln Gly Thr Ala Thr Ile Gly Pro Val Asn
                420                 425                 430

Tyr Ile Cys Glu Ala Ser Gln Ser Pro Asn Val Val Pro
                435                 440                 445

<210> SEQ ID NO 31
<211> LENGTH: 571
<212> TYPE: PRT
<213> ORGANISM: Fowl adenovirus C

<400> SEQUENCE: 31

Met Ala Lys Ser Thr Pro Phe Ala Phe Ser Met Gly Gln His Ser Ser
1               5                   10                  15

Arg Lys Arg Pro Ala Asp Ser Glu Asn Thr Gln Asn Ala Ser Lys Val
                20                  25                  30

Ala Lys Thr Gln Thr Ser Ala Thr Arg Ala Gly Val Asp Gly Asn Asp
            35                  40                  45

Asp Leu Asn Leu Val Tyr Pro Phe Trp Leu Gln Asn Ser Thr Ser Gly
50                  55                  60

Gly Gly Gly Gly Ser Gly Gly Asn Pro Ser Leu Asn Pro Pro Phe
65                  70                  75                  80

Ile Asp Pro Asn Gly Pro Leu Tyr Val Gln Asn Ser Leu Leu Tyr Val
                85                  90                  95

Lys Thr Thr Ala Pro Ile Glu Val Asn Lys Ser Leu Ala Leu Ala
                100                 105                 110

Tyr Asp Ser Ser Leu Ala Val Asp Ala Gln Asn Gln Leu Gln Val Lys
            115                 120                 125

Val Asp Thr Glu Gly Pro Ile Arg Ile Ser Pro Asp Gly Leu Asp Ile
130                 135                 140

Ala Val Asp Pro Ser Thr Leu Glu Val Asp Asp Glu Trp Glu Leu Ala
145                 150                 155                 160

Val Lys Leu Asp Pro Asn Gly Pro Leu Thr Ala Ser Ser Ala Gly Ile
                165                 170                 175

Asn Ile Asn Val Asp Asp Thr Leu Leu Ile Glu Asp Asp Ala Asn
            180                 185                 190

Gln Ala Lys Glu Leu Gly Val His Leu Asn Pro Asn Gly Pro Ile Thr
            195                 200                 205

Ala Asp Arg Asp Gly Leu Asp Leu Glu Ile Asp Ser Gln Thr Met Val
210                 215                 220
```

Val Lys Asp Ser Gly Thr Ser Gly Gly Val Leu Gly Val Leu Leu Lys
225                 230                 235                 240

Pro Ser Gly Gly Leu Gln Ser Ser Ile Gln Gly Ile Gly Val Ala Val
            245                 250                 255

Ala Asp Thr Leu Thr Ile Thr Ser Asn Thr Val Glu Val Lys Thr Asp
            260                 265                 270

Pro Asn Gly Ser Ile Ser Tyr Ser Ala Asn Gly Ile Ala Val Lys Pro
            275                 280                 285

Asp Pro Ser Gly Pro Leu Thr Ser Ser Gly Thr Gly Leu Ser Val Val
290                 295                 300

Thr Ala Ala Glu Gly Ser Ile Gln Ser Ser Asn Ala Gly Leu Ala Val
305                 310                 315                 320

Lys Thr Asp Pro Ser Gly Pro Ile Thr Ser Gly Ser Asn Gly Leu Asn
                325                 330                 335

Leu Ser Tyr Asn Ala Ser Asp Phe Thr Val Ser Gln Gly Val Leu Asn
                340                 345                 350

Ile Ile Arg Asn Pro Ser Thr Leu Pro Asp Ala Tyr Leu Glu Ser Gly
                355                 360                 365

Thr Asn Tyr Leu Asn Asn Phe Thr Ala Gln Ala Glu Asn Ser Ser Val
370                 375                 380

Phe Lys Phe Asn Cys Ala Tyr Phe Leu Gln Ser Trp Tyr Ser Asn Gly
385                 390                 395                 400

Leu Val Thr Ser Ser Leu Tyr Leu Lys Ile Asp Arg Ala Gln Phe Ser
                405                 410                 415

Asn Met Pro Thr Gly Gln Ser Ala Glu Asn Ala Arg Tyr Phe Thr Phe
                420                 425                 430

Trp Val Pro Thr Tyr Glu Ser Leu Asn Leu Ser Arg Val Ser Thr Pro
                435                 440                 445

Thr Ile Thr Pro Asn Thr Val Gln Trp Gly Ala Phe Ser Pro Ala Gln
450                 455                 460

Asn Cys Ser Gly Asn Pro Ala Phe Gln Tyr Asn Leu Thr Gln Pro Pro
465                 470                 475                 480

Ser Ile Tyr Phe Glu Pro Lys Ser Gly Ser Val Gln Thr Phe Gln Pro
                485                 490                 495

Val Leu Thr Gly Ala Trp Asn Thr Asp Thr Tyr Asn Pro Gly Thr Val
                500                 505                 510

Gln Val Cys Ile Leu Pro Gln Thr Val Val Gly Gly Gln Ser Thr Phe
                515                 520                 525

Val Asn Met Thr Cys Tyr Asn Phe Arg Cys Gln Asn Pro Gly Ile Phe
530                 535                 540

Lys Val Ala Ala Ser Asn Gly Thr Phe Thr Ile Gly Pro Ile Phe Tyr
545                 550                 555                 560

Ser Cys Pro Thr Asn Glu Leu Thr Arg Pro Thr
                565                 570

<210> SEQ ID NO 32
<211> LENGTH: 523
<212> TYPE: PRT
<213> ORGANISM: Fowl adenovirus C

<400> SEQUENCE: 32

Met Ala Thr Ser Thr Pro His Ala Phe Ser Phe Gly Gln Ile Gly Ser
1               5                   10                  15

Arg Lys Arg Pro Ala Gly Gly Asp Gly Glu Arg Asp Ala Ser Lys Val
            20                  25                  30

```
Pro Lys Met Gln Thr Pro Ala Pro Ser Ala Thr Ala Asn Gly Asn Asp
        35                  40                  45

Glu Leu Asp Leu Val Tyr Pro Phe Trp Leu Gln Asn Gly Ser Thr Gly
        50                  55                  60

Gly Gly Gly Gly Gly Gly Ser Gly Gly Asn Pro Ser Leu Asn Pro
65                  70                  75                  80

Pro Phe Leu Asp Pro Asn Gly Pro Leu Ala Val Gln Asn Asn Leu Leu
                85                  90                  95

Lys Val Asn Thr Ala Ala Pro Ile Thr Val Ala Asn Lys Ala Leu Thr
                100                 105                 110

Leu Ala Tyr Glu Pro Asp Ser Leu Glu Leu Thr Asn Gln Gln Gln Leu
                115                 120                 125

Ala Val Lys Ile Asp Pro Glu Gly Pro Leu Lys Ala Thr Thr Glu Gly
                130                 135                 140

Ile Gln Leu Ser Val Asp Pro Thr Thr Leu Glu Val Asp Asp Val Asp
145                 150                 155                 160

Trp Glu Leu Thr Val Lys Leu Asp Pro Asp Gly Pro Leu Asp Ser Ser
                165                 170                 175

Ala Thr Gly Ile Thr Val Arg Val Asp Glu Thr Leu Leu Ile Glu Asp
                180                 185                 190

Val Gly Ser Gly Gln Gly Lys Glu Leu Gly Val Asn Leu Asn Pro Thr
                195                 200                 205

Gly Pro Ile Thr Ala Asp Asp Gln Gly Leu Asp Leu Glu Ile Asp Asn
                210                 215                 220

Gln Thr Leu Lys Val Asn Ser Val Thr Gly Gly Gly Val Leu Ala Val
225                 230                 235                 240

Gln Leu Lys Ser Gln Gly Gly Leu Thr Ala Gln Thr Asp Gly Ile Gln
                245                 250                 255

Val Asn Thr Gln Asn Ser Ile Thr Val Thr Asn Gly Ala Leu Asp Val
                260                 265                 270

Lys Val Ala Ala Asn Gly Pro Leu Glu Ser Thr Asp Thr Gly Leu Thr
                275                 280                 285

Leu Asn Tyr Asp Pro Gly Asp Phe Thr Val Asn Ala Gly Thr Leu Ser
                290                 295                 300

Ile Ile Arg Asp Pro Ala Leu Val Ala Asn Ala Tyr Leu Thr Ser Gly
305                 310                 315                 320

Ala Ser Thr Leu Gln Gln Phe Thr Ala Lys Ser Glu Asn Ser Ser Gln
                325                 330                 335

Phe Ser Phe Pro Cys Ala Tyr Tyr Leu Gln Gln Trp Leu Ser Asp Gly
                340                 345                 350

Leu Val Leu Ser Ser Leu Tyr Leu Lys Leu Asp Arg Ala Gln Phe Thr
                355                 360                 365

Asn Met Pro Thr Gly Ala Asn Tyr Gln Asn Ala Arg Tyr Phe Thr Phe
                370                 375                 380

Trp Val Gly Ala Gly Thr Ser Phe Asn Leu Ser Leu Thr Glu Pro
385                 390                 395                 400

Thr Ile Thr Pro Asn Thr Thr Gln Trp Asn Ala Phe Ala Pro Ala Leu
                405                 410                 415

Asp Tyr Ser Gly Ala Pro Pro Phe Ile Tyr Asp Ala Ser Ser Val Val
                420                 425                 430

Thr Ile Tyr Phe Glu Pro Thr Ser Gly Arg Leu Glu Ser Tyr Leu Pro
                435                 440                 445
```

```
Val Leu Thr Asp Asn Trp Ser Gln Thr Tyr Asn Pro Gly Thr Val Thr
    450                 455                 460

Leu Cys Val Lys Thr Val Arg Val Gln Leu Arg Ser Gln Gly Thr Phe
465                 470                 475                 480

Ser Thr Leu Val Cys Tyr Asn Phe Arg Cys Gln Asn Thr Gly Ile Phe
                485                 490                 495

Asn Ser Asn Ala Thr Ala Gly Thr Met Thr Leu Gly Pro Ile Phe Phe
            500                 505                 510

Ser Cys Pro Ala Leu Ser Thr Ala Asn Ala Pro
            515                 520

<210> SEQ ID NO 33
<211> LENGTH: 554
<212> TYPE: PRT
<213> ORGANISM: Fowl adenovirus C

<400> SEQUENCE: 33

Met Ala Gln Pro Ser Gly Leu Leu Gly Lys Arg Lys Arg Pro Glu
1               5                   10                  15

Ala Pro Leu Asp Asp Ser Ala Gly Val Ser Glu Gln Pro Leu Thr Ala
                20                  25                  30

Ser Lys Met Pro Lys Thr His Thr Tyr Ser Ser Pro Ile Gly Phe Tyr
            35                  40                  45

Gly Pro Thr Thr Gly Gln Leu Asp Leu Val Tyr Pro Phe Trp Phe Gln
    50                  55                  60

Asn Ser Ser Gly Gly Gly Gly Thr Val Ile Pro Pro Val Asn Pro
65                  70                  75                  80

Pro Leu Leu Asp Pro Ala Gly Pro Leu Tyr Val Gln Asn Asn Met Leu
                85                  90                  95

Arg Met Arg Thr Gly Ala Pro Ile Val Val Ser Asn Gly Ala Leu Gly
            100                 105                 110

Leu Ser Tyr Asp Thr Ser Leu Gly Leu Ser Asp Gln Asn Gln Leu Gln
        115                 120                 125

Val Asn Leu Glu Pro Asn Gly Pro Leu Lys Ala Thr Asp Asp Gly Ile
    130                 135                 140

Glu Leu Thr Val Asp Pro Leu Thr Leu Glu Val Thr Asp Trp Glu Leu
145                 150                 155                 160

Gly Val Lys Ile Asp Pro Ala Gly Pro Leu Asp Ala Ser Thr Asp Gly
                165                 170                 175

Leu Thr Leu Arg Thr Asp Asp Thr Leu Ser Leu Gly Gln Asp Pro Thr
            180                 185                 190

Thr His Glu Tyr Glu Leu Gly Leu Lys Leu Asp Pro Ser Gly Pro Leu
        195                 200                 205

Glu Ala Ser Ala Asp Gly Leu Asn Leu Arg Leu Asp Thr Leu Leu
    210                 215                 220

Val Glu Gln Asp Thr Thr Thr Gln Glu Tyr Glu Leu Gly Val His Leu
225                 230                 235                 240

Asn Pro Asn Gly Pro Val Thr Ala Asp Glu Asn Gly Ile Asp Leu Glu
                245                 250                 255

Ile Asn Thr Asp Thr Leu Thr Val Thr Ala Gly Ala Ala Gly Gly Gly
            260                 265                 270

Glu Leu Ser Val Leu Leu Asn Pro Gln Gly Ala Ile His Ala Thr Ala
        275                 280                 285

Ser Thr Gly Ile Gly Val Ala Val Gly Pro Gly Leu Gln Ile Thr Ser
    290                 295                 300
```

```
Asn Thr Val Ser Val Lys Pro Asp Pro Ala Gly Pro Leu Thr Ala Ser
305                 310                 315                 320

Pro Thr Gly Val Thr Leu Asn Tyr Asp Asn Ser Asp Phe Thr Ile Thr
                325                 330                 335

Asp Gly Lys Leu Thr Leu Tyr Lys Thr Pro Ala Val Thr Ser Asp Ala
            340                 345                 350

Tyr Leu Thr Ser Gly Asn Ser Ala Met Thr Thr Tyr Thr Ala Phe Phe
        355                 360                 365

Gly Asn Ser Ser Asn Tyr Arg Phe Lys Cys Ser Tyr Phe Leu Gln Gln
    370                 375                 380

Trp Leu Arg Asp Arg Leu Val Ile Thr Ser Leu Tyr Ile Lys Leu Asp
385                 390                 395                 400

Arg Ser Gln Leu Glu Asn Leu Ser Ser Asp Ala Ser Ala Gln Asn Ala
            405                 410                 415

Arg Tyr Phe Thr Phe Trp Val Ser Ser Asn Ala Leu Met Asn Leu Ser
            420                 425                 430

Gly Ile Asp Glu Pro Val Val Thr Pro Ser Thr Val Thr Trp Ser Lys
            435                 440                 445

Phe Leu Pro Asp Val Asn Tyr Thr Asn Pro Pro Thr Phe Asn Phe Asn
    450                 455                 460

Thr Ser Leu Tyr Phe Glu Pro Pro Ser Gly Glu Ile Leu Thr Phe Asn
465                 470                 475                 480

Pro Val Thr Thr Gly Asp Trp Ser Thr Thr Tyr Ser Pro Gly Thr Val
                485                 490                 495

Ser Val Cys Val Leu Pro Val Asn Val Arg Ala Ser Ser Gly Thr Gly
            500                 505                 510

Thr Leu Gln Thr Leu Leu Cys Phe Asn Phe Arg Cys Ala Asn Thr Gly
        515                 520                 525

Leu Phe Lys Thr Ala Ala Thr Thr Gly Thr Phe Tyr Val Gly Pro Ile
    530                 535                 540

Val Tyr Ser Cys Pro Gly Asn Pro Leu Ile
545                 550
```

FOWL ADENOVIRUS VACCINE

CROSS-REFERENCE TO RELATED APPLICATIONS

This application is a national phase application under 35 U.S.C. § 371 of International Application No. PCT/EP2014/067654 filed 19 Aug. 2014, which claims priority to European Patent Application No. 13180849.5 filed 19 Aug. 2013. The entire contents of each of the above-referenced disclosures is specifically incorporated by reference herein without disclaimer.

The invention relates to methods and compositions (formulations) for the prevention of hepatitis-hydropericardium syndrome (HHS).

HHS is an infectious disease of chickens, characterized by high mortality and severe economic losses, mainly in broiler flocks. After first reports of the disease in 1987 from Pakistan, outbreaks have been documented mainly in Asian countries, Central and South America. Initial assumptions pointed towards the involvement of an unknown agent in addition to an adenovirus which was later revised by reproducing the disease in specific pathogen-free birds following oral infection with virulent fowl adenovirus (FAdV) species C strains.

Fowl adenoviruses are members of the family Adenoviridae and genus Aviadenovirus. Five species (FAdV-A to FAdV-E) and 12 serotypes (FAdV-1 to 8a and 8b to 11), identified by cross-neutralization test, have so far been recognized.

Adenoviruses are non-enveloped particles with a double-stranded DNA genome and a diameter of 70-90 nm.

The major structural proteins of an adenovirus are hexons and pentons, constituting an icosahedral capsid of 252 subunits (capsomers), with hexons forming the facets and pentons capping the vertices of the icosahedron. The penton base anchors the antenna-like fiber protein, whose distal head domain, termed knob, harbors the receptor-binding site and is thus essential for initiating virus attachment to the host cell.

The FAdV capsid is characterized by a morphological peculiarity of two fiber proteins associated with each penton base, whereas mammalian adenoviruses feature only one fiber protein per vertex. Although the existence of dual fibers is common to all FAdVs, two fibers distinct in sequence and length, each encoded by a separate gene, are a specific feature of FAdV-1 (FAdV-A) (Hess et al., J. Mol. Biol. 252 (1995), 379-385). Based on the novel finding of two separate fiber-encoding genes in an FAdV-C isolate, it was recently demonstrated that this reflects, among all FAdV species with equally long fiber proteins, a feature exclusively attributed to members of FAdV-C (Marek et al., Vet. Microbiol. 156 (2012), 411-417).

Characterization of the knob as receptor-binding domain has established the fiber molecule as a critical factor associated with infection properties of adenoviruses, such as alterations in tissue tropism and virulence. However, many questions are still open in regard to the individual functionality of the dual fibers present in FAdVs, particularly in the context of interaction with host cell receptors.

As major surface-exposed capsid structures, fiber and hexon are key mediators of antigenicity in adenoviruses and carriers of a panoply of epitopes of subgroup- and type-specificity. It has also been shown that hexon- and fiber-specific antibodies account for most of the neutralizing activity in mammalian humoral response against adenovirus. Recently, in vitro trials demonstrated different degrees of neutralizing capacity of antibodies raised against recombinant hexon and fiber proteins of the egg-drop syndrome virus (EDSV (DAdV-A=DAdV-1)).

Owing to their antigenic properties, adenovirus capsid structures have been proposed as potential candidates for the design of epitope-based vaccines.

Strategies to combat HHS have concentrated on the prevention of infection and on the provision of attenuated fowl adenovirus vaccines (WO 03/039593) or inactivated vaccines from infected liver homogenates (Anjum et al. 1990) or grown up virus on primary cells (Alvarado et al. 2007). Due to the ubiquitous occurrence of FAdVs, however, applying such conventional vaccines and verification of effectiveness of the vaccination is of limited use due to the lack of discrimination between vaccination and infection. A subunit vaccine against HHS based on the penton base (expressed in E. coli) was recently suggested (Shah et al., (Vaccine 30 (2012); 7153-7156)); however it is usually difficult to detect antibodies as an indicator of successful immunization because of the omnipresence of other fowl adenoviruses.

US 2011/165224 A1 discloses isolated FAdV strains of specific serotypes for inducing protective immunity. These compositions contain whole (live or killed) viruses, no subunit vaccines or isolated FAdV proteins. Griffin et al. (J. Gen. Virol. 92 (2011); 1260-1272) disclose coding potential and transcript analysis of FAdV-4. It is speculated that FAdV-4 fiber 2 (short fiber) which is "predicted to be protein-coding" (but not shown to be expressed) might bind a receptor and determine the tissue tropism of FAdV-4, "perhaps leading to the unique clinical features associated with infection of virulent FadV-4". The authors correctly point out that both, avian FAdV-1 and the human enteric serotypes HAdV-40 and HAdV-41 (=HADV-F), contain two fiber genes. However, there are significant differences: Whereas in FAdV-1, as in all fowl AdVs, always two fibers per penton base are assembled together, there is only one fiber in the HAdV-Fs. Moreover, different quantities of both fibers are assembled into the HAdV-F virion although expression is the same on mRNA level (Song et al., Virology 432 (2012), 336-342). This shows that both fibers have different functions in the assembled virion (this has been verified in receptor studies). Moreover, Tan et al. (J. Gen. Virol. 82 (2001), 1465-1472) have shown that fiber 2 is involved in virus assembly and in the interaction with an unknown cellular receptor. Since FAdV-1 comprises—in contrast to all other FAdVs—two fibers of completely different lengths, such results cannot be transferred to other serotypes.

Marek et al. (Vet. Microbiol. 156 (2012); 411-417) discloses the fact that two fiber genes of nearly equal length are present in FAdV-C whereas other serotypes have only one fiber gene. Although it is mentioned that "fibers of FAdV play an important role in infectivity and pathogenicity of FAdV" (demonstrated in 1996!), this statement was identified by Marek et al. as "purely speculative" as far as FAdV-C is concerned. Furthermore, the likelihood that fiber proteins are involved in infectivity and pathogenicity does not automatically implicate the successful application of recombinant proteins as a vaccine.

Fingerut et al. (Vaccine 21 (2003); 2761-2766) disclose a subunit vaccine against the adenovirus egg-drop syndrome using part of its fiber protein.

It is an object of the present invention to provide a safe and specific vaccine for efficient prevention of HHS in birds, especially in poultry. The vaccine should be easy and cost-effective to produce and be suitable for administration on an industrial basis. Successful immunization with the vaccine should be easily detectable and confirmable.

Therefore, the present invention discloses a vaccine comprising a fiber 2 protein of Fowl Adenovirus C (FAdV-C) or an immunogenic fragment thereof for use in preventing hepatitis-hydropericardium syndrome (HHS) in birds, preferably in poultry, especially in broilers.

The present invention provides the teaching that the fiber-2 protein of FAdV-C is an effective subunit vaccine that protects birds, especially chicken, completely from HHS. This finding was remarkable because fiber-1 protein of FAdV-C as well as hexon-derived subunit vaccines (hexon loop 1) did not show a protective effect. It is evident that the present vaccines with isolated subunits, i.e. isolated single proteins or protein fragments, essentially differ from vaccines that are based on live, attenuated or killed (whole) viruses. Accordingly, the present invention provides a completely novel and—in view of the teachings present in the present field for fiber and hexon-derived proteins in FAdVs—surprisingly effective strategy for vaccinating birds to manage prevention of HHS, IBH and GE.

For the present invention, any fiber-2 protein of FAdV-C can be used. In the examples of the present invention, fiber-2 protein from reference strain KR5 was used as reference (UniProt entry H8WQW9); however, also other fiber-2 protein sequences of FAdV-C can be used, e.g. from reference strains ON1 (GU188428=NC_015323) or CFA20 (AF160185) or any other FAdV-C field isolates, e.g. isolates IV37, K99-97, K388-95, K88-95, K31, Peru53, Peru54, c344, K1013, AG234, C2B, 09-584, 09-8846, 09-2602, 922-1, Da60, K1013QT and INTO (as disclosed by Marek et al., Vet. Microbiol. 156 (2012), 411-417); corresponding to UniProt entries H8WG65, H8WG69, H8WG72, H8WG77, H8WG70, H8WG73, H8WG66, H8WG76, H8WG60, H8WG61, H8WG62, H8WG75, H8WG67, H8WG78, H8WG63, H8WG68, H8WG64, H8WG74, H8WG71, H8WQZ7, H8WQZ2, H8WQW9, Q0GH78, O55281, and F2VJI5.

The term “fiber-2 protein” is accepted in the present field of technology. All fiber proteins, especially the sub-group of fiber-2 proteins are unified by a characteristic amino acid sequence resulting in a characteristic structure with specific and conserved amino acid motifs.

Instead of using the whole fiber-2 protein of FAdV-C, only immunogenic fragments of fiber-2 protein can be used as vaccines according to the present invention. Immunogenic fragments can be any polypeptide from a fiber-2 protein of a naturally occurring FAdV-C isolate with a minimum length of 7 amino acid residues, preferably with a minimum length of 8 amino acid residues, especially with a minimum length of 9 amino acid residues. These minimum lengths provide sufficient MHC binding. Suitable motifs can be verified experimentally or via computer prediction (see e.g. Wallny et al., PNAS 103(2006), 1434-1439; Huo et al., PLoS ONE 7 (2012): e39344. doi:10.1371). Preferred lengths of the immunogenic fragments are therefore 7 to 100 amino acids, preferably 8 to 50 amino acids, more preferred 8 to 20 amino acids, especially 8 to 16 amino acids. For example, the immunogenic fragments according to the present invention may contain octapeptides or nonapeptides based on the peptide-binding motifs of chicken MHC class I molecules belonging to the B4, B12, B15, and B19 haplotypes (Wallny et al., 2006; Huo et al., 2012). The motifs were as follows: B4: x-(D or E)-x-x-(D or E)-x-x-E; B12: x-x-x-x(V or I)-x-x-V and x-x-x-x-(V or I)-x-x-x(V); B15: (K or R)-R-x-x-x-x-x-Y and (K or)-R-x-x-x-xx-x-Y; B19: x-R-x-x-x-x-x-(Y, P, L, F) and x-R-x-x-x-x-x-x-(Y, P, L, F).

The fiber-2 protein has a tail domain (amino acid 1 to 65), a shaft domain (amino acid 66 to 276) and a head domain (amino acid 277 to 479; all amino acid sequence numbers in this general specification are based on the fiber-2 protein of the KR5 reference strain (UniProt H8WQW9; Marek et al., 2012)). Preferred immunogenic fragments of the present invention contain the following motifs (based on amino acid numbering according to fiber-2 of KR5): 400 to 450, preferably 410 to 440, more preferred 420-440; 70 to 95, preferably 75 to 93, especially 75 to 90; 20 to 70, preferably 25 to 65, especially 45 to 65 and 25 to 47; 200 to 225, 265 to 290, 350 to 385, 460 to 480, 165 to 190, 320 to 350 and 290 to 320.

Examples of immunogenic fragments are fragments comprising one or more of the following amino acid sequences of fiber-2 protein (again according to the amino acid sequence of fiber-2 of KR5 and corresponding to the alignment in FIG. 5):

| | | | |
|---|---|---|---|
| Most preferred: | 424 to 438 | 253 to 267 | 26 to 40 |
| 23 to 37 | 421 to 435 | 425 to 439 | 403 to 417 |
| 24 to 38 | 422 to 436 | 254 to 268 | 404 to 418 |
| 22 to 36 | 423 to 437 | 78 to 92 | 405 to 419 |
| 25 to 39 | 424 to 438 | 424 to 438 | 406 to 420 |
| 21 to 35 | 425 to 439 | 424 to 438 | 407 to 421 |
| 424 to 438 | 426 to 440 | 79 to 93 | 408 to 422 |
| 254 to 268 | 427 to 441 | 77 to 91 | 409 to 423 |
| 423 to 437 | 423 to 437 | 423 to 437 | 69 to 83 |
| 255 to 269 | | | |
| 20 to 34 | | | |
| 325 to 339 | | | |
| 355 to 369 | | | |
| 425 to 439 | | | |
| 423 to 437 | | | |
| 45 to 59 | | | |
| 46 to 60 | | | |
| 47 to 61 | | | |
| 48 to 62 | | | |
| 49 to 63 | | | |
| 50 to 64 | | | |
| 51 to 65 | | | |
| 326 to 340 | | | |
| 255 to 269 | | | |
| 326 to 340 | | | |

| | | | |
|---|---|---|---|
| Highly preferred: | 207 to 221 | 426 to 440 | 308 to 322 |
| | 208 to 222 | 324 to 338 | 283 to 297 |
| 424 to 438 | 209 to 223 | 167 to 181 | 71 to 85 |
| 26 to 40 | 210 to 224 | 168 to 182 | 425 to 439 |
| 27 to 41 | 267 to 281 | 169 to 183 | 426 to 440 |
| 28 to 42 | 268 to 282 | 170 to 184 | 77 to 91 |
| 29 to 43 | 269 to 283 | 171 to 185 | 422 to 436 |
| 30 to 44 | 270 to 284 | 172 to 186 | 68 to 82 |
| 31 to 45 | 271 to 285 | 173 to 187 | 426 to 440 |
| 32 to 46 | 272 to 286 | 356 to 370 | 282 to 296 |
| 75 to 89 | 273 to 287 | 70 to 84 | 426 to 440 |
| 76 to 90 | 353 to 367 | 353 to 367 | 356 to 370 |
| 77 to 91 | 354 to 368 | 192 to 206 | 281 to 295 |
| 78 to 92 | 355 to 369 | 54 to 68 | 284 to 298 |
| 79 to 93 | 356 to 370 | 55 to 69 | 78 to 92 |
| 80 to 94 | 357 to 371 | 322 to 336 | 310 to 324 |
| 81 to 95 | 358 to 372 | 323 to 337 | 311 to 325 |
| 354 to 368 | 359 to 373 | 324 to 338 | 53 to 67 |
| 283 to 297 | 69 to 83 | 325 to 339 | 183 to 197 |
| 425 to 439 | 76 to 90 | 326 to 340 | 313 to 327 |
| 422 to 436 | 425 to 439 | 422 to 436 | 314 to 328 |
| 325 to 339 | 327 to 341 | 422 to 436 | 315 to 329 |
| 282 to 296 | 68 to 82 | 327 to 341 | 316 to 330 |
| 422 to 436 | 252 to 266 | 56 to 70 | 317 to 331 |

| | | | |
|---|---|---|---|
| 253 to 267 | 309 to 323 | 294 to 308 | 318 to 332 |
| 423 to 437 | 442 to 456 | 295 to 309 | 319 to 333 |
| 322 to 336 | 256 to 270 | 296 to 310 | 52 to 66 |
| 323 to 337 | 426 to 440 | 297 to 311 | 252 to 266 |
| 324 to 338 | 68 to 82 | 298 to 312 | 183 to 197 |
| 325 to 339 | 69 to 83 | 299 to 313 | 297 to 311 |
| 326 to 340 | 70 to 84 | 300 to 314 | 422 to 436 |
| 327 to 341 | 71 to 85 | 355 to 369 | 328 to 342 |
| 328 to 342 | 72 to 86 | 325 to 339 | 59 to 73 |
| 70 to 84 | 73 to 87 | 191 to 205 | 60 to 74 |
| 425 to 439 | 74 to 88 | 355 to 369 | 61 to 75 |
| 423 to 437 | 464 to 478 | 71 to 85 | 62 to 76 |
| 424 to 438 | 465 to 479 | 441 to 455 | 63 to 77 |
| 204 to 218 | 310 to 324 | 421 to 435 | 64 to 78 |
| 205 to 219 | 80 to 94 | 256 to 270 | 65 to 79 |
| 206 to 220 | 443 to 457 | 79 to 93 | 463 to 477 |
| 184 to 198 | 188 to 202 | | |
| 254 to 268 | 76 to 90 | | |
| 309 to 323 | 194 to 208 | | |
| 207 to 221 | 77 to 91 | | |
| 43 to 57 | 326 to 340 | | |
| 324 to 338 | 193 to 207 | | |
| 52 to 66 | 79 to 93 | | |
| 53 to 67 | 282 to 296 | | |
| 54 to 68 | 69 to 83 | | |
| 55 to 69 | 184 to 198 | | |
| 56 to 70 | 298 to 312 | | |
| 57 to 71 | 23 to 37 | | |
| 58 to 72 | 70 to 84 | | |
| 185 to 199 | 379 to 393 | | |
| 323 to 337 | 283 to 297 | | |
| 444 to 458 | 296 to 310 | | |
| 324 to 338 | 283 to 297 | | |
| 356 to 370 | | | |
| 78 to 92 | | | |
| 206 to 220 | | | |
| 364 to 378 | | | |
| 376 to 390 | | | |
| 377 to 391 | | | |
| 378 to 392 | | | |
| 379 to 393 | | | |
| 380 to 394 | | | |
| 381 to 395 | | | |
| 382 to 396 | | | |
| 71 to 85 | | | |
| 192 to 206 | | | |
| 378 to 392 | | | |
| 421 to 435 | | | |
| 192 to 206 | | | |
| 297 to 311 | | | |
| 182 to 196 | | | |
| 183 to 197 | | | |
| 184 to 198 | | | |
| 185 to 199 | | | |
| 186 to 200 | | | |
| 187 to 201 | | | |

| | | | |
|---|---|---|---|
| Preferred: | 283 to 297 | 127 to 141 | 355 to 369 |
| 424 to 438 | 284 to 298 | 186 to 200 | 425 to 439 |
| 354 to 368 | 285 to 299 | 465 to 479 | 421 to 435 |
| 27 to 41 | 286 to 300 | 310 to 324 | 206 to 220 |
| 426 to 440 | 284 to 298 | 257 to 271 | 283 to 297 |
| 255 to 269 | 440 to 454 | 421 to 435 | 80 to 94 |
| 282 to 296 | 261 to 275 | 323 to 337 | 308 to 322 |
| 357 to 371 | 310 to 324 | 208 to 222 | 312 to 326 |
| 193 to 207 | 251 to 265 | 378 to 392 | 91 to 105 |
| 261 to 275 | 363 to 377 | 72 to 86 | 92 to 106 |
| 307 to 321 | 207 to 221 | 93 to 107 | 93 to 107 |
| 352 to 366 | 24 to 38 | 207 to 221 | 94 to 108 |
| 354 to 368 | 319 to 333 | 320 to 334 | 95 to 109 |
| 75 to 89 | 282 to 296 | 86 to 100 | 96 to 110 |
| 261 to 275 | 182 to 196 | 458 to 472 | 97 to 111 |
| 295 to 309 | 260 to 274 | 459 to 473 | 69 to 83 |
| 44 to 58 | 22 to 36 | 460 to 474 | 424 to 438 |
| 207 to 221 | 293 to 307 | 461 to 475 | 169 to 183 |
| 169 to 183 | 428 to 442 | 462 to 476 | 165 to 179 |

| | | | |
|---|---|---|---|
| 253 to 267 | 429 to 443 | 281 to 295 | 166 to 180 |
| 311 to 325 | 296 to 310 | 280 to 294 | 101 to 115 |
| 292 to 306 | 168 to 182 | 281 to 295 | 102 to 116 |
| 185 to 199 | 260 to 274 | 77 to 91 | 103 to 117 |
| 464 to 478 | 318 to 332 | 205 to 219 | 104 to 118 |
| 465 to 479 | 78 to 92 | 308 to 322 | 105 to 119 |
| 283 to 297 | 309 to 323 | 193 to 207 | 106 to 120 |
| 423 to 437 | 79 to 93 | 204 to 218 | 107 to 121 |
| 206 to 220 | 191 to 205 | 261 to 275 | 191 to 205 |
| 42 to 56 | 192 to 206 | 260 to 274 | 298 to 312 |
| 287 to 301 | 193 to 207 | 170 to 184 | 259 to 273 |
| 288 to 302 | 194 to 208 | 377 to 391 | 423 to 437 |
| 289 to 303 | 195 to 209 | 282 to 296 | 309 to 323 |
| 290 to 304 | 196 to 210 | 167 to 181 | 205 to 219 |
| 291 to 305 | 197 to 211 | 190 to 204 | 261 to 275 |
| 292 to 306 | 282 to 296 | 310 to 324 | 357 to 371 |
| 293 to 307 | 28 to 42 | 189 to 203 | 256 to 270 |
| 357 to 371 | 317 to 331 | 190 to 204 | 291 to 305 |
| 280 to 294 | 245 to 259 | 309 to 323 | 295 to 309 |
| 281 to 295 | 206 to 220 | 284 to 298 | 327 to 341 |
| 282 to 296 | 67 to 81 | 76 to 90 | 294 to 308 |
| 170 to 184 | 258 to 272 | 443 to 457 | 161 to 175 |
| 283 to 297 | 328 to 342 | 307 to 321 | 162 to 176 |
| 347 to 361 | 203 to 217 | 81 to 95 | 163 to 177 |
| 421 to 435 | 322 to 336 | 29 to 43 | 355 to 369 |
| 208 to 222 | 128 to 142 | 94 to 108 | 204 to 218 |
| 281 to 295 | 262 to 276 | 311 to 325 | 421 to 435 |
| 191 to 205 | 85 to 99 | 284 to 298 | 406 to 420 |
| 244 to 258 | 55 to 69 | 421 to 435 | 118 to 132 |
| 464 to 478 | 452 to 466 | 80 to 94 | 71 to 85 |
| 57 to 71 | 75 to 89 | 72 to 86 | 294 to 308 |
| 58 to 72 | 422 to 436 | 202 to 216 | 346 to 360 |
| 425 to 439 | 77 to 91 | 79 to 93 | 426 to 440 |
| 348 to 362 | 353 to 367 | 323 to 337 | 280 to 294 |
| 349 to 363 | 321 to 335 | 281 to 295 | 45 to 59 |
| 350 to 364 | 28 to 42 | 312 to 326 | 290 to 304 |
| 351 to 365 | 78 to 92 | 87 to 101 | 297 to 311 |
| 352 to 366 | 262 to 276 | 28 to 42 | 320 to 334 |
| 284 to 298 | 453 to 467 | 281 to 295 | 119 to 133 |
| 379 to 393 | 123 to 137 | 285 to 299 | 20 to 34 |
| 311 to 325 | 124 to 138 | 465 to 479 | 21 to 35 |
| 327 to 341 | 125 to 139 | 356 to 370 | 22 to 36 |
| 260 to 274 | 126 to 140 | 194 to 208 | 23 to 37 |
| 182 to 196 | 127 to 141 | 309 to 323 | 24 to 38 |
| 445 to 459 | 128 to 142 | 306 to 320 | 25 to 39 |
| 262 to 276 | 129 to 143 | 252 to 266 | 404 to 418 |
| 422 to 436 | 265 to 279 | 306 to 320 | 442 to 456 |
| 55 to 69 | 266 to 280 | 443 to 457 | 289 to 303 |
| 450 to 464 | 320 to 334 | 405 to 419 | 281 to 295 |
| 451 to 465 | 321 to 335 | 54 to 68 | 170 to 184 |
| 452 to 466 | 366 to 380 | 41 to 55 | 258 to 272 |
| 453 to 467 | 367 to 381 | 204 to 218 | 259 to 273 |
| 454 to 468 | 368 to 382 | 24 to 38 | 260 to 274 |
| 455 to 469 | 369 to 383 | 380 to 394 | 261 to 275 |
| 456 to 470 | 370 to 384 | 251 to 265 | 262 to 276 |
| 310 to 324 | 371 to 385 | 208 to 222 | 263 to 277 |
| 70 to 84 | 372 to 386 | 348 to 362 | 264 to 278 |
| 208 to 222 | 284 to 298 | 157 to 171 | 442 to 456 |
| 353 to 367 | 322 to 336 | 158 to 172 | 443 to 457 |
| 205 to 219 | 246 to 260 | 159 to 173 | 444 to 458 |
| 328 to 342 | 260 to 274 | 160 to 174 | 445 to 459 |
| 446 to 460 | 262 to 276 | 308 to 322 | 117 to 131 |
| 447 to 461 | 376 to 390 | 444 to 458 | 70 to 84 |
| 448 to 462 | 21 to 35 | 254 to 268 | 346 to 360 |
| 347 to 361 | 311 to 325 | 195 to 209 | 310 to 324 |
| 186 to 200 | 170 to 184 | 126 to 140 | 25 to 39 |
| 68 to 82 | 294 to 308 | 189 to 203 | 29 to 43. |
| 403 to 417 | 54 to 68 | 93 to 107 | 465 to 479 |
| 213 to 227 | 29 to 43 | 295 to 309 | 292 to 306 |
| 25 to 39 | 298 to 312 | 192 to 206 | 345 to 359 |
| 27 to 41 | 364 to 378 | 194 to 208 | 164 to 178 |
| 259 to 273 | 290 to 304 | 227 to 241 | 137 to 151 |
| 27 to 41 | 259 to 273 | 71 to 85 | 263 to 277 |
| 169 to 183 | 205 to 219 | 70 to 84 | 209 to 223 |
| 407 to 421 | 92 to 106 | 23 to 37 | 305 to 319 |
| 321 to 335 | 280 to 294 | 316 to 330 | 171 to 185 |
| 365 to 379 | 28 to 42 | 1 to 15 | 136 to 150 |
| 442 to 456 | 33 to 47 | 206 to 220 | 280 to 294 |
| 299 to 313 | 34 to 48 | 293 to 307 | 66 to 80 |

| | | | |
|---|---|---|---|
| 227 to 241 | 35 to 49 | 56 to 70 | 67 to 81 |
| 308 to 322 | 36 to 50 | 1 to 15 | 181 to 195 |
| 309 to 323 | 37 to 51 | 243 to 257 | 358 to 372 |
| 310 to 324 | 38 to 52 | 369 to 383 | 284 to 298 |
| 311 to 325 | 205 to 219 | 325 to 339 | 295 to 309 |
| 312 to 326 | 80 to 94 | 225 to 239 | 325 to 339 |
| 377 to 391 | 39 to 53 | 226 to 240 | 129 to 143 |
| 72 to 86 | 40 to 54 | 227 to 241 | 94 to 108 |
| 29 to 43 | 245 to 259 | 228 to 242 | 307 to 321 |
| 348 to 362 | 262 to 276 | 229 to 243 | 291 to 305 |
| 307 to 321 | 426 to 440 | 230 to 244 | 251 to 265 |
| 345 to 359 | 69 to 83 | 231 to 245 | 252 to 266 |
| 346 to 360 | 280 to 294 | 76 to 90 | 253 to 267 |
| 347 to 361 | 312 to 326 | 349 to 363 | 254 to 268 |
| 361 to 375 | 464 to 478 | 378 to 392 | 255 to 269 |
| 362 to 376 | 319 to 333 | 451 to 465 | 256 to 270 |
| 363 to 377 | 354 to 368 | 296 to 310 | 257 to 271 |
| 364 to 378 | 187 to 201 | 69 to 83 | 288 to 302 |
| 365 to 379 | 322 to 336 | 356 to 370 | 285 to 299 |
| 169 to 183 | 325 to 339 | 228 to 242 | 254 to 268 |
| 311 to 325 | 308 to 322 | 76 to 90 | 228 to 242 |
| 168 to 182 | 67 to 81 | 71 to 85 | 257 to 271 |
| 319 to 333 | | | |
| 440 to 454 | | | |

Figure 5A:
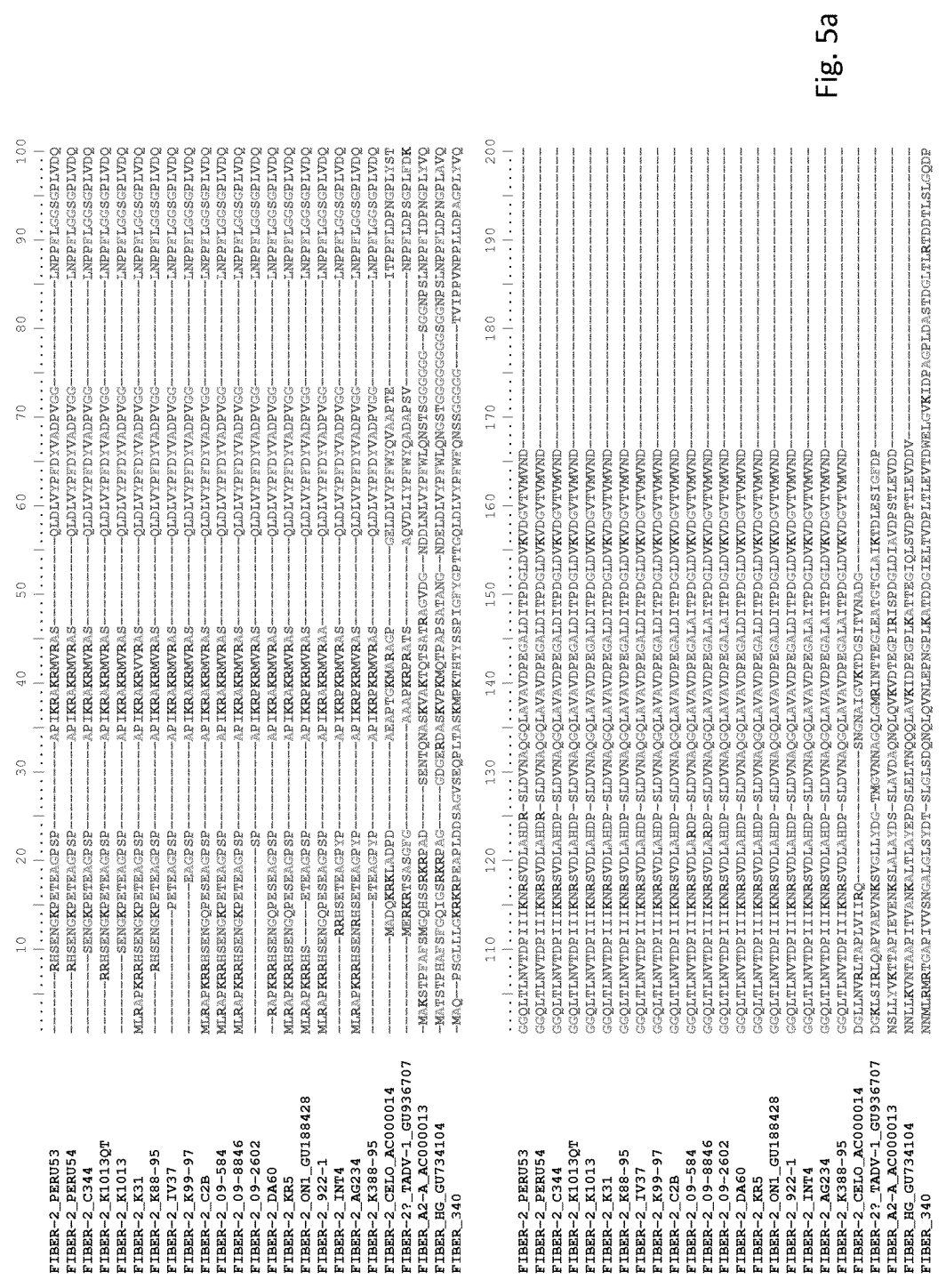
Figure 5B:
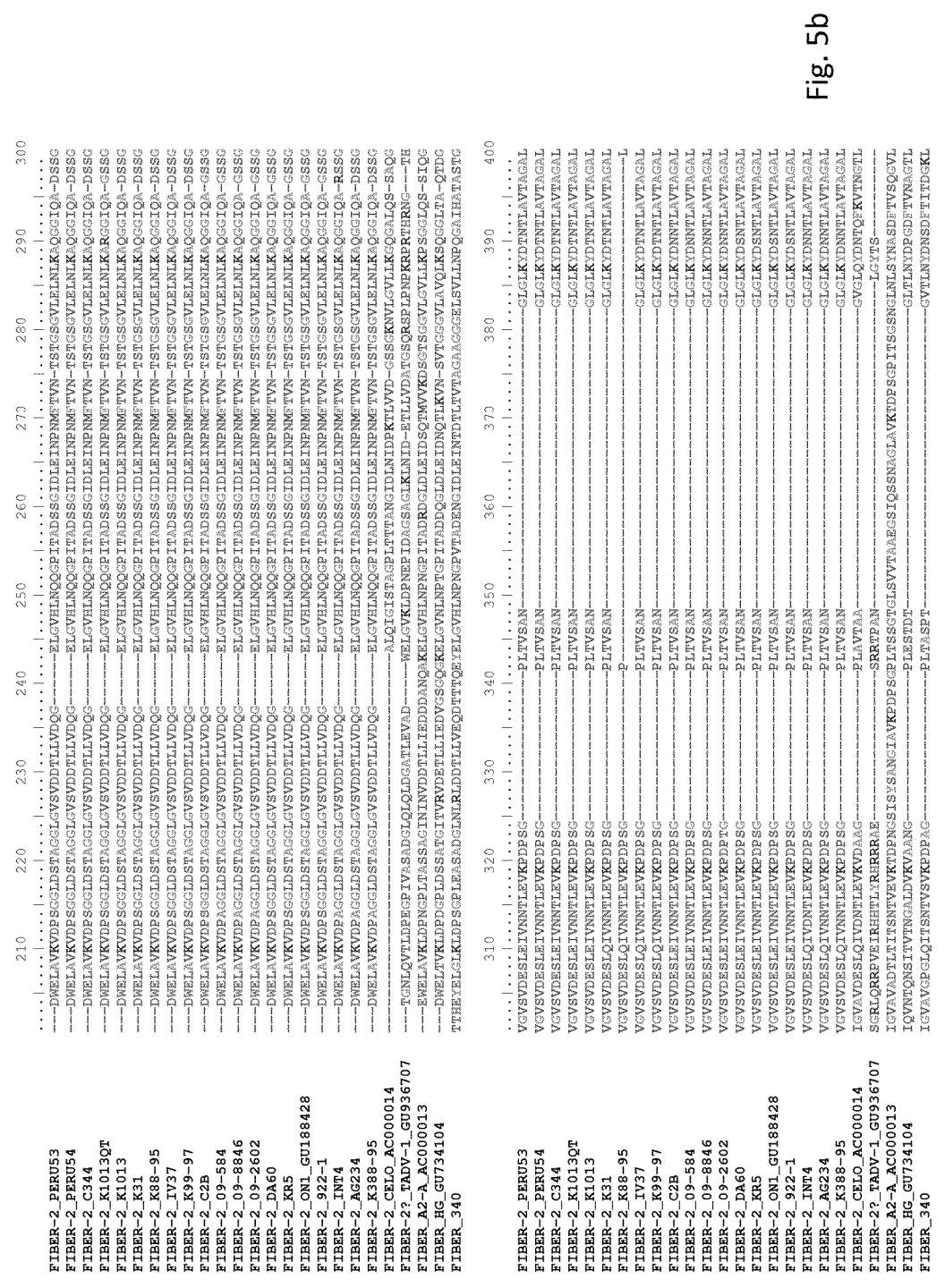
Figure 5C:
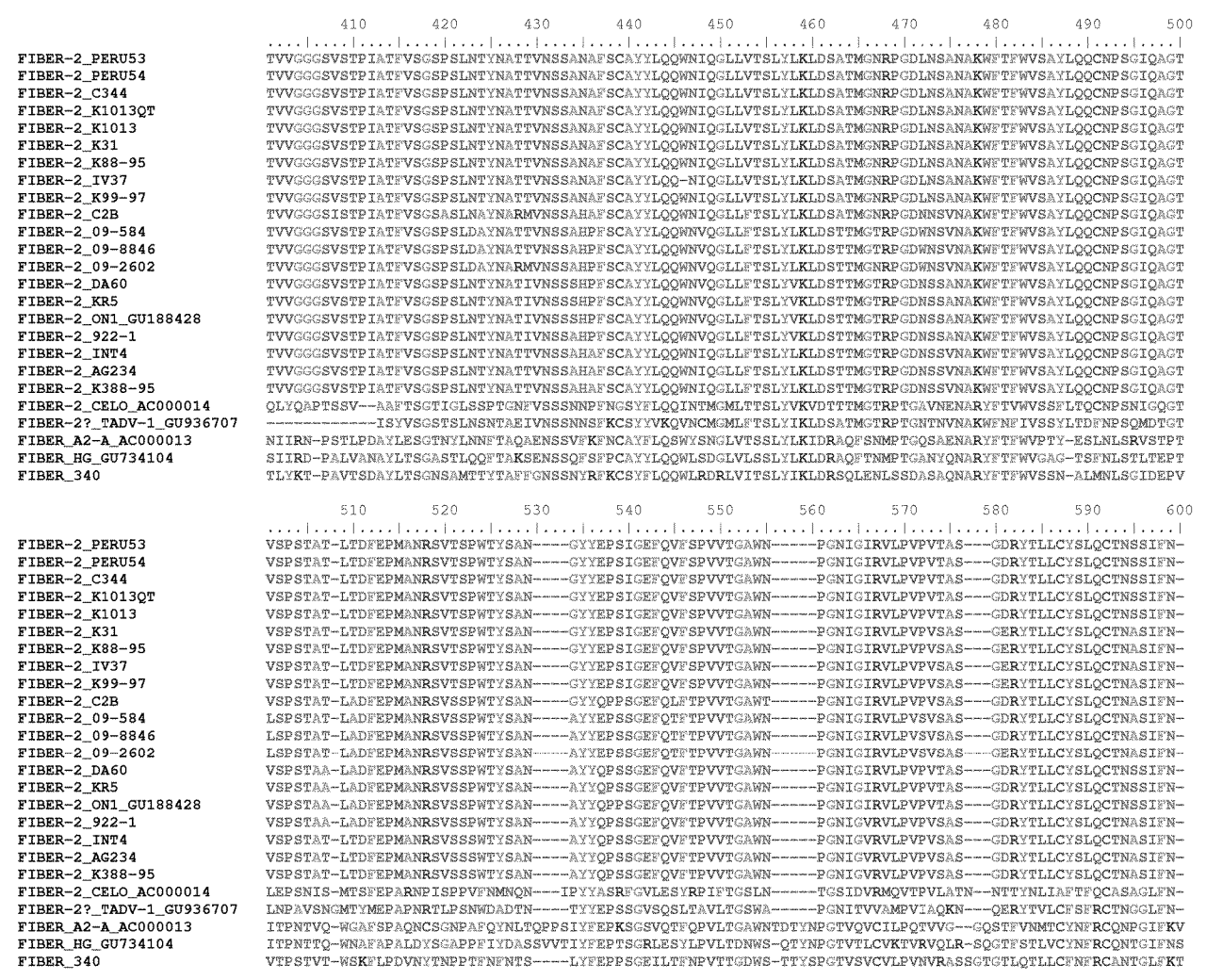

The vaccine according to the present invention preferably contains a fiber-2 protein of FAdV-C, selected from the sequences UniProt entries H8WG65, H8WG69, H8WG72, H8WG77, H8WG70, H8WG73, H8WG66, H8WG76, H8WG60, H8WG61, H8WG62, H8WG75, H8WG67, H8WG78, H8WG63, H8WG68, H8WG64, H8WG74, H8WG71, H8WQZ7, H8WQZ2, H8WQW9, Q0GH78, O55281, and F2VJI5, as well as the protein sequences provided in FIG. 5 and Table 3, especially H8WQW9, or immunogenic fragments thereof; or immunogenic sequences with at least 80, preferably at least 90, especially at least 95% amino acid identity, or immunogenic fragments thereof (based on alignment with the Clustal Omega program; identity is calculated by the ratio of identical amino acids divided by the total number of amino acids (of the shorter sequence, if sequences are not of the same length), times 100 (for %)). For example, amino acid residues on position (based on the KR5 sequence H8WQW9) 29, 31, 36, 91, 93, 114, 115, 213, 219, 232, 235, 279, 291, 294, 295, 299, 300, 302 to 307, 319, 324, 329, 343, 338, 343 to 346, 372, 378, 380, 391, 393, 400, 403, 405, 406, 411, 413, 421, 427, 433, 435, 439, 453, 459, 476, or 478 can be changed (as evidenced by the isolates of UniProt sequences H8WG65, H8WG69, H8WG72, H8WG77, H8WG70, H8WG73, H8WG66, H8WG76, H8WG60, H8WG61, H8WG62, H8WG75, H8WG67, H8WG78, H8WG63, H8WG68, H8WG64, H8WG74, H8WG71, H8WQZ7, H8WQZ2, H8WQW9, Q0GH78, O55281, and F2VJI5); or deletion of sequences, such as at the N-terminus (e.g. up to position 21), 123 to 139, 250 to 272, 364, or at the C-terminus, e.g. positions 464 to 479 (as also evidenced by the above UniProt sequences; alignments made by the UniProt alignment software (Clustal Omega program)). Further naturally occurring amino acid variations, deletions and insertions are exemplified in FIG. 5 and derivable from the sequences in Table 3.

Preferably, the vaccine according to the present invention further comprises an adjuvant, preferably selected from the group consisting of Freund's complete adjuvant, Freund's incomplete adjuvant, aluminum hydroxide, *Bordetella pertussis*, saponin, muramyl dipeptide, ethylene vinyl acetate copolymer, oil, a vegetable oil or a mineral oil, in particular peanut oil or silicone oil, and combinations thereof.

Adjuvants are substances that enhance the immune response to immunogens. Adjuvants, can include aluminum hydroxide and aluminum phosphate, saponins e.g., Quil A, water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di(caprylate/caprate), glyceryl tri (caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycerol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic® products, especially L121. For example the adjuvant-containing vaccine is prepared in the following way: 50 to 90 v/v of aqueous phase comprising the immunogen are emulsified in 1 to 10% w/v of anhydromannitol oleate, 1 to 10% w/v of oleic acid ethoxylated with 11 EO (ethylene oxide) and 5 to 40% v/v of light liquid paraffin oil (European Pharmacopea type) with the aid of an emulsifying turbomixer. An alternative method for preparing the emulsion consists in emulsifying, by passages through a high-pressure homogenizer, a mixture of 1 to 10% w/v squalane, to 10% w/v Pluronic® L121, 0.05 to 1% w/v of an ester of oleic acid and of anhydrosorbitol ethoxylated with 20 EO, 50 to 95% v/v of the aqueous phase comprising the immunogen. It is also possible to formulate with synthetic polymers (e.g., homo- and copolymers of lactic and glycolic acid, which have been used to produce microspheres that encapsulate immunogens, e.g., biodegradable microspheres). A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with poly-alkenyl ethers of sugars or polyalcohols. These compounds are known by the term carbomer, e.g. acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, alkyls and other ethylenically unsaturated groups. The unsaturated radicals may themselves contain other substituents, such as methyl. The products sold under the name Carbopol® (BF Goodrich, Ohio, USA) are particularly appropriate. They are cross-linked with an allyl sucrose or with allyl pentaerythritol. Among then, there may be mentioned Carbopol® 974P, 934P and 971P. Among the copolymers of maleic anhydride and alkenyl derivative, the copolymers EMA® (Monsanto) which are copolymers of maleic anhydride and ethylene, linear or cross-linked, for example cross-linked with divinyl ether, are preferred. The dissolution of these polymers in water leads to an acid solution that will be neutralized, preferably to physiological pH, in order to give the adjuvant solution into which the immunogenic, immunological or vaccine composition itself will be incorporated. The carboxyl groups of the polymer are then partly in COO⁻ form.

Preferably, a solution of adjuvant according to the invention, is prepared in distilled water, preferably in the presence of sodium chloride, the solution obtained being at acidic pH.

This stock solution is diluted by adding it to the desired quantity (for obtaining the desired final concentration), or a substantial part thereof, of water charged with NaCl, preferably physiological saline (NaCl 9 g/l) all at once in several portions with concomitant or subsequent neutralization (pH 7.3 to 7.4), preferably with NaOH. This solution at physiological pH will be used as it is for mixing with the vaccine, which may be especially stored in freeze-dried, liquid or frozen form. From this disclosure and the knowledge in the art, the skilled artisan can select a suitable adjuvant, if desired, and the amount thereof to employ in an immunological, immunogenic or vaccine composition according to the invention, without undue experimentation.

Accordingly, the vaccine according to the present invention preferably comprises a pharmaceutically acceptable diluent and/or carrier, preferably selected from the group consisting of water-for-injection, physiological saline, tissue culture medium, propylene glycol, polyethylene glycol, vegetable oils, especially olive oil, and injectable organic esters such as ethyl oleate.

The Fiber 2 protein of FAdV-C can be produced by any suitable expression system. Preferably, production is effected in a eukaryotic expression system. Specifically preferred expression systems are a baculovirus expression system, an *E. coli* expression system, or a *Pichia pastoris* expression system. However, virtually any suitable expression system or vector can be used in the production of the vaccine provided by this invention. By way of illustration, said suitable expression or vector systems can be selected, according to the conditions and needs of each specific case, from plasmids, bacmids, yeast artificial chromosomes (YACs), bacteria artificial chromosomes (BACs), bacteriophage P1-based artificial chromosomes (PACs), cosmids, or viruses, which can further have a heterologous replication origin, for example, bacterial or of yeast, so that it may be amplified in bacteria or yeasts, as well as a marker usable for selecting the transfected cells different from the gene or genes of interest. These expression systems or vectors can be obtained by conventional methods known by persons skilled in the art.

The vaccines according to the present invention can be produced in industrial amounts; the individual vaccine dose given to the animals can be in the ranges also applied for other vaccines. Preferably, the fiber-2 protein of FAdV-C or an immunogenic fragment thereof is contained in the vaccine in an amount of 0.1 µg/ml to 10 mg/ml, preferably of 1 µg/ml to 1 mg/ml, especially of 10 to 100 µg/ml.

In a preferred form, the vaccine according to the present invention consists of fiber-2 protein of FAdV-C or an immunogenic fragment thereof, preferably in an amount of 0.1 µg to 10 mg, preferably of 1 µg to 1 mg, especially of 10 to 100 µg; and a pharmaceutically acceptable carrier and/or diluent and/or adjuvant.

The vaccine according to the present invention preferably comprises a pharmaceutically acceptable vehicle, especially if provided as commercially sold vaccine product. The suitable vehicles may be both aqueous and non-aqueous. Examples of non-aqueous solvents are propylene glycol, polyethylene glycol, vegetable oils such as olive oil, and injectable organic esters such as ethyl oleate.

With the present invention, an efficient method for preventing HHS in birds is provided. Accordingly, the present invention relates to another aspect to a method for preventing HHS in birds, preferably in poultry, especially in parent flocks, comprising administering to poultry, especially to the parent flock, a vaccine containing fiber-2 protein of FAdV-C or an immunogenic fragment thereof. The vaccine is administered to the birds in an effective amount at a suitable point in time. Typical ways of administration are intravenous, subcutaneous, intramuscular, oral, in ovo or intracloacal administration. Preferably, vaccination in chicken is effected in week 17 to 19, especially in week 18 of life.

A specific advantage of the present invention is that vaccination of the parent flock provides sufficient protection for the progeny, especially to broilers, to safeguard sufficient protection e.g. up to at least 30, preferably at least 40, especially at least 60 days, to the progeny of vaccinated animals. It is therefore advantageous that the present invention provides sufficient protection of the broilers by vaccination of the parent animals. Accordingly, protection of broilers is effected by immunization of the parental animal in poultry, especially in chicken.

According to another aspect, the present invention also provides a kit comprising a fiber-2 protein of FAdV-C or an immunogenic fragment thereof immobilised on a solid surface. Preferably, the kit is a serological kit for detection of anti-fiber-2 antibodies (within the meaning of the present invention) in samples, especially blood samples of animals. This kit is specifically suitable for the present invention to detect the successful vaccination by determining specific anti-fiber-2 antibodies in the vaccinated animals. In the course of establishing the present invention it was found that specific detection of anti-fiber-2 antibodies in the vaccinated animals is difficult or even impossible by commercially available FAdV-test kits, especially FAdV-ELISAs, or by usual serum neutralization tests (SNTs). It was observed that only detection with fiber-2-specific tests (e.g. Fib-2 ELISAs and the like) was possible. This was due to type specificity and the non-neutralizing capacity of the antibodies elicited by the vaccination according to the present invention. Nevertheless ((and even more remarkable)), sufficient protection is provided with the vaccine according to the present invention.

This shows that there was also a need to provide a specific test and test system to establish whether protection is given (by the determining the presence of specific antibodies against fibre-2 protein of FAdV-C). This could be provided by the kit according to the present invention that—in contrast to the commercially available FAdV-ELISAs and SNTs (that might produce false negative results)—successfully and reliably confirm successful vaccination. The kit of the present invention also provides a means for detecting infection with FAdV viruses, because fiber-2 protein of FAdV-C is very specific for the individual viruses. Moreover, the kit according to the present invention is also suitable for determining whether antibody protection is still present in progeny of vaccinated animals or whether an active immunization of the progeny is indicated.

Preferably, the kit according to the present invention further comprises means for detection of the binding of an antibody to the immobilised fiber-2 protein of FAdV-C or the immobilised immunogenic fragment thereof, preferably an antibody being specific for bird antibodies, especially an anti-chicken IgG antibody or an anti-turkey IgG antibody. Of course, any suitable detection (capturing) means for the binding event between fiber-2 protein protein and an antibody from the vaccinated bird is suitable for the present kit; however, (secondary) antibodies or suitable (secondary) antibody fragments that are able to bind to the anti-fiber-2 antibodies antibodies to be detected in a (blood) sample of the vaccinated bird are specifically preferred.

It is specifically preferable to provide a solid phase test kit with a labelled agent that detects the binding event to the immobilised fiber-2 protein. Accordingly, detection agent for the binding event, especially the anti-chicken IgG antibody or the anti-turkey IgG antibody, is a labelled agent, especially a labelled antibody. For example, the agent (antibody/antibody fragment) is labelled with a colourigenic, fluorescent, luminescent or radioactive label.

Suitable labels are therefore e.g. fluorescent compounds, isotopic compounds, chemiluminescent compounds, quantum dot labels, biotin, enzymes, electron-dense reagents, and haptens or proteins for which antisera or monoclonal antibodies are available. The various means of detection include but are not limited to spectroscopic, photochemical, radiochemical, biochemical, immunochemical, or chemical means.

The label may be of a chemical, peptide or nucleic acid molecule nature although it is not so limited. Other detectable labels include radioactive isotopes such as $^{32}$P, luminescent markers such as fluorochromes, optical or electron density markers, etc., or epitope tags such as the FLAG epitope or the HA epitope, biotin, avidin, and enzyme tags such as horseradish peroxidase, β-galactosidase, etc. The label may be bound to a peptide during or following its synthesis. There are many different labels and methods of labeling known to those of ordinary skill in the art. Examples of the types of labels that can be used in the present invention include enzymes, radioisotopes, fluorescent compounds, colloidal metals, chemiluminescent compounds, and bioluminescent compounds. Those of ordinary skill in the art will know of other suitable labels for the agents (antibodies/antibody fragments) described herein, or will be able to ascertain such, using routine experimentation. Furthermore, the coupling or conjugation of these labels to the peptides of the invention can be performed using standard techniques common to those of ordinary skill in the art.

The invention is further illustrated by the following examples and figures, yet without being restricted thereto.

FIG. 1. Survival rates of birds of group I (Fib-1 vaccinated), group II (Fib-2 vaccinated) and group III (Hex L1 vaccinated), together with groups IV (positive control) and V (negative control), after infection with virulent FAdV strain AG234.

Figure 2:
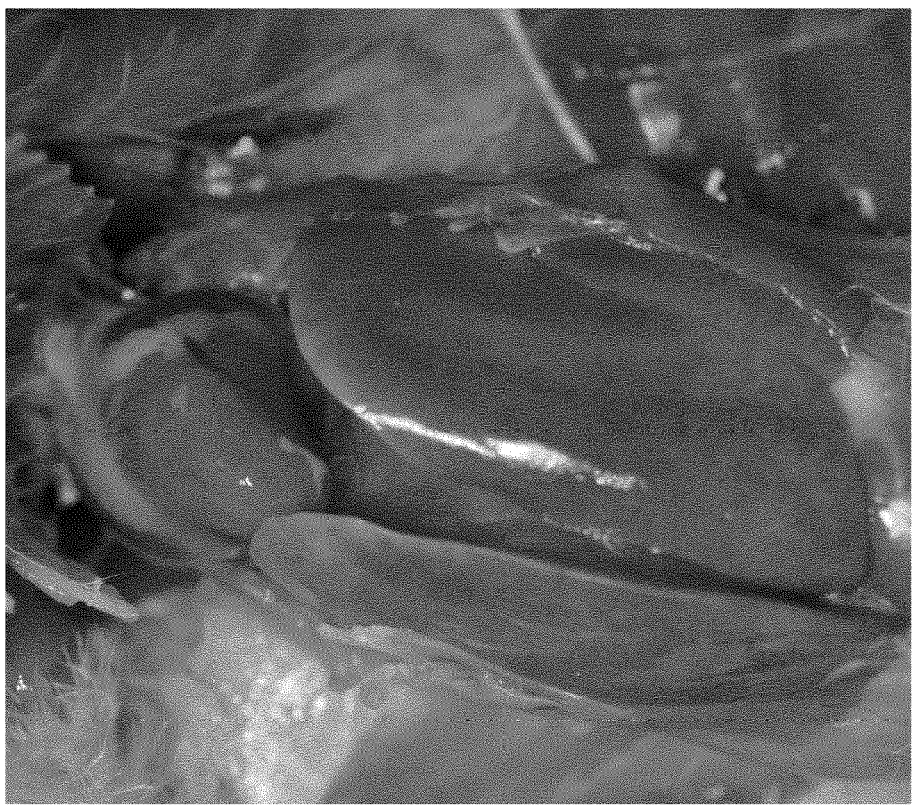

FIG. 2. Pathologic lesions as manifested by focal necroses in the liver and pericardial sac filled with straw-coloured fluid in a bird from the positive control group IV that died 3 days post challenge (d.p.c.).

Figure 3:
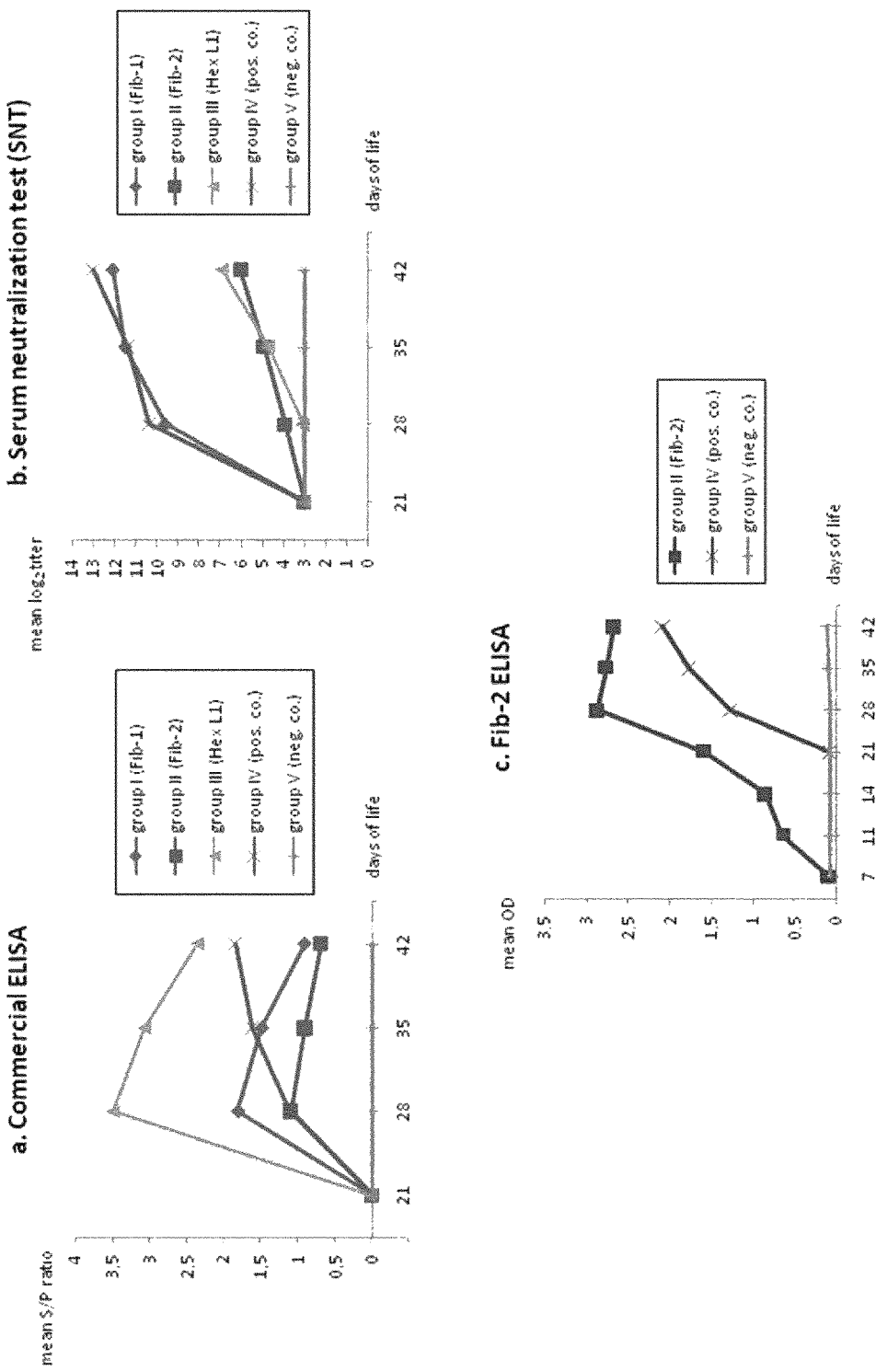

FIG. 3. Results of antibody investigation as detected by (a) commercial FAdV Group-1 ELISA (results indicated as Sample to Positive (S/P) ratio of the mean OD value of maximum ten tested sera from each group, starting measurements on day 21 (before challenge), (b) Serum neutralization test (SNT) (results indicated as log$_2$ transformed mean titers of maximum ten tested sera from each group, starting measurements on day 21; titres≤3 were considered negative), and (c) custom-made ELISA using recombinant Fib-2 protein (results indicated as mean OD values measured from sera of all Fib-2 vaccinated birds as well as positive and negative control birds, starting on day 7).

Figure 4:
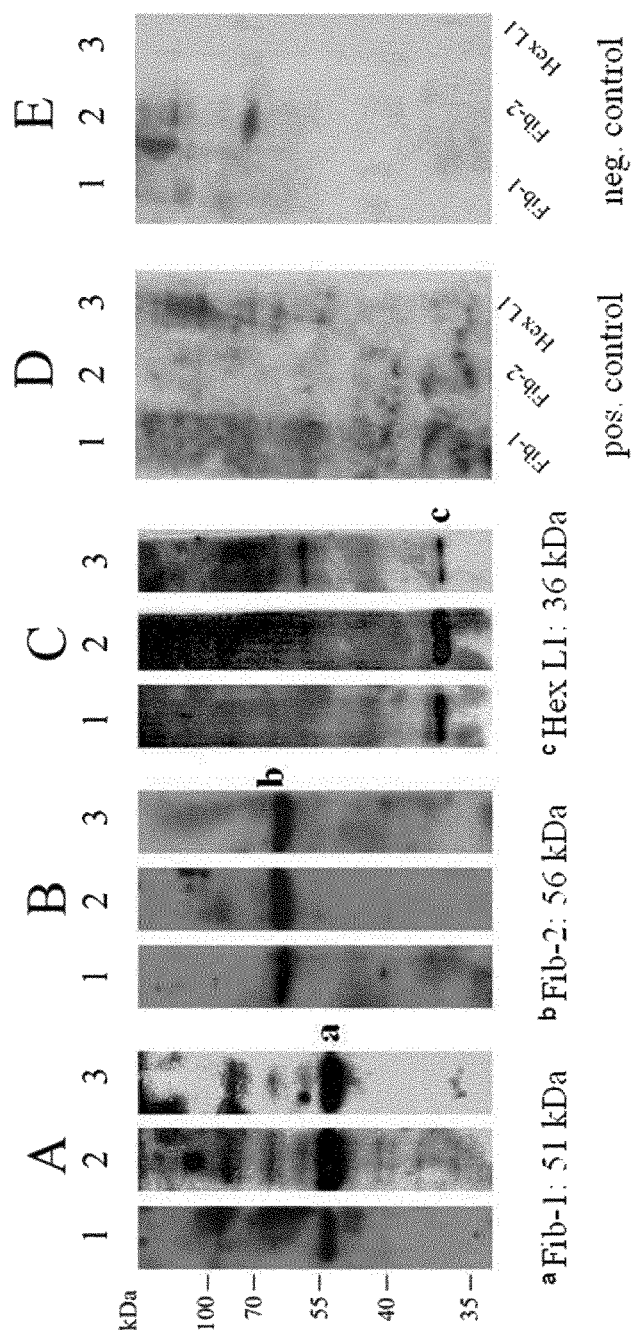

FIG. 4. Immunoblots of purified recombinant KR5 proteins incubated with chicken sera collected on 21st day of life (preabsorbed with insect cell powder, diluted 1:2000). A, lanes 1, 2 and 3 purified Fib-1 incubated with sera from Fib-1 vaccinated birds. B, lanes 1, 2 and 3 purified Fib-2 incubated with sera from Fib-2 vaccinated birds. C, lanes 1, 2 and 3 purified Hex L1 incubated with sera from Hex L1 vaccinated birds. D, lane 1 purified Hex L1, lane 2 purified Fib-1, lane 3 purified Fib-2, incubated with serum from a bird of the positive control group (vaccinated with purified, non-infected insect cell material). E, lane 1 purified Hex L1, lane 2 purified Fib-1, lane 3 purified Fib-2, incubated with serum from a bird of the negative control group (non-vaccinated). Proteins are detected by serum antibodies as bands migrated to estimated molecular weight sizes of 51 kDa (Fib-1), 56 kDa (Fib-2) and 36 kDa (Hex L1).

FIG. 5. Alignment of fiber proteins according to the present invention (Fib-2 of FAdV-C). Alignment is shown for (SEQ ID NO: 9) FIBER-2_PERU53, (SEQ ID NO: 10) FIBER-2_PERU54, (SEQ ID NO: 11) FIBER-2_C344, (SEQ ID NO: 12) FIBER-2_K1013QT, (SEQ ID NO: 13) FIBER-2_K1013, (SEQ ID NO: 14) FIBER-2_K31, (SEQ ID NO: 15) FIBER-2_K88-95, (SEQ ID NO: 16) FIBER-2_IV37, (SEQ ID NO: 17) FIBER-2_K99-97, (SEQ ID NO: 18) FIBER-2_C2B, (SEQ ID NO: 19) FIBER-2_09-584, (SEQ ID NO: 20) FIBER-2_09-8846, (SEQ ID NO: 21) FIBER-2_09-2602, (SEQ ID NO: 22) FIBER-2_DA60, (SEQ ID NO: 23) FIBER-2_KR5, (SEQ ID NO: 24) FIBER-2_ON1_GU188428, (SEQ ID NO: 25) FIBER-2_922-1, (SEQ ID NO: 26) FIBER-2_INT4, (SEQ ID NO: 27) FIBER-2_AG234, (SEQ ID NO: 28) FIBER-2_K388-95, (SEQ ID NO: 29) FIBER-2_CELO AC000014, (SEQ ID NO: 30) FIBER-2?_TADV-1_GU936707, (SEQ ID NO: 31) FIBER_A2-A_AC000013, (SEQ ID NO: 32) FIBER_HG_GU734104, and (SEQ ID NO: 33) FIBER_340.

EXAMPLES

In the examples of the present invention, fiber-1, fiber-2 and the loop-1 region of hexon of an FAdV-C reference strain (KR5), were recombinantly expressed in the baculovirus system. In a vaccination trial, the efficacy of these capsid components to induce protective immunity in chickens was assessed by challenging birds with virulent FAdV. Hence, this is the first study of its kind to employ both fiber proteins individually in an in vivo experiment with the aim to further elucidate the functional significance of the investigated FAdV capsid proteins in the infection process and to address their potential use as candidate subunit vaccines for the control of HHS.

1. Materials and Methods
1.1. Virus Propagation and DNA Extraction

FAdV-C (=FAdV-4) reference strain KR5 and the challenge virus AG234 were propagated on primary chicken-embryo liver (CEL) cells according to a protocol described by Schat and Sellers, A Laboratory Manual for the Isolation and Identification of Avian Pathogens, (2008), 195-203). Viral titer was determined according to the method of Reed and Muench (Am. J. Hyg. 27 (1938), 493-497) by endpoint titration. DNA extraction from cell culture supernatant was carried out with the DNeasy Blood & Tissue Kit (Qiagen, Hilden, Germany).

1.2. Cloning and Initial Protein Expression

Primers were designed on the basis of the complete genomic KR5 sequence (GenBank accession number HE608152) and contained 5'-terminal restriction sites for cloning into the pFastBac transfer vector (Invitrogen, Vienna, Austria) (Table 1). The entire encoding regions for fiber-1 and fiber-2 (nucleotides 30438 to 31739 and 31723 to 33162, respectively) and the hexon loop-1 region (nucleotides 20481 to 21366) were amplified from the FAdV-C reference strain KR5 using a proofreading DNA polymerase (Invitrogen, Vienna, Austria). Following intermediate cloning into the pCR4Blunt-TOPO vector (Invitrogen) and digestion with BamHI/StuI (Fib-1), StuI/XbaI (Fib-2) and NcoI/XhoI (Hex L1) fragments were ligated into the cleaved pFastBac vector at the respective restriction sites. After determining the correct insertion of each product into pFast-Bac by sequencing, the construct was transformed into competent *E. coli* DH10Bac cells (Invitrogen, Vienna, Austria). Recombinant baculovirus DNA was isolated from transformed colonies using the S.N.A.P. Miniprep Kit (Invitrogen, Vienna, Austria). The genes of interest were expressed in *Spodoptera frugiperda* Sf9 cells (Invitrogen, Vienna, Austria) as His-tag fusion proteins according to the manufacturer's protocol.

1.3. Identification of Recombinant Proteins

To verify expression of the recombinant proteins and to optimize the expression conditions, SDS-PAGE was performed on the soluble and membrane-bound fractions of the cell lysate, collected from infected Sf9 monolayer cultures at different time intervals (24, 48, 72, 96 h) post-infection. Recombinant proteins were identified by immunoblot using anti polyhistidine antibody (Sigma-Aldrich, Vienna, Austria). Non-infected Sf9 cells were processed in the same way to serve as negative control.

1.4. Expression and Purification of Recombinant Proteins

For expression, Sf9 suspension cultures (50 ml) were infected with amplified recombinant baculovirus at an MOI of 3. Cultures collected after 72 h inoculation in a shaking incubator were concentrated by centrifugation for 5 min at 3500 rpm. The resulting cell pellet was disrupted by resuspension in lysis buffer (containing 20 mM sodium phosphate, 0.5 M NaCl, 20-40 mM imidazole, 0.2 mg/ml lysozyme, 20 µg/ml DNAse, 1 mM $MgCl_2$, 1 mM PMSF and proteinase inhibitors) and sonication, with subsequent incubation on ice for 1 h. Clarified supernatants obtained by centrifugation of the crude cell lysates at 14000 rpm for 20 min at 4° C. were used for purification on affinity chromatography columns (His GraviTrap, GE Healthcare, Freiburg, Germany). Hexon L1 protein presented as insoluble material in the pellet fraction was solubilised with phosphate buffer containing 8 M urea. The 0.45 µm-filtered sample was loaded on columns equilibrated with phosphate buffer containing 8 M urea, and the protein was eluted after step-washing the columns with decreasing concentrations of urea. Samples from each purification fraction were subsequently analyzed for presence of the proteins of interest by SDS-PAGE and immunoblotting.

Prior to in vivo administration, the recombinant proteins were transferred into sterile PBS (Gibco/Invitrogen, Vienna, Austria) by buffer exchange in Slide-A-Lyzer 7K Dialysis Cassettes (Thermo Scientific, Vienna, Austria). Protein Hex L1 was additionally processed through Amicon Ultra-15 size exclusion spin columns (Millipore, Vienna, Austria) to remove eluted insect cell proteins and to concentrate the target protein. Protein concentrations were determined by Bradford assay (Thermo Scientific, Vienna, Austria).

1.5. Animal Experiment

A total of 112 SPF (specific pathogen-free) chickens (VALO, Lohmann Tierzucht GmbH, Cuxhaven, Germany) were divided into five groups that were housed separately in isolator units (Montair Andersen bv, HM 1500, Sevenum, Netherlands). At first day of life, a 500 µl injection was administered intramuscularly to each animal, containing 50 µg of the recombinant protein, with group I (n=26) receiving fiber-1 (Fib-1), group II (n=28) receiving fiber-2 (Fib-2) and group III (n=26) receiving hexon loop-1 (Hex L1), mixed 1:1 with GERBU Adjuvant LQ #3000 (GERBU Biotechnik GmbH, Heidelberg, Germany; a sterile aqueous suspension of lipid particles with excipients and emulsifiers).

Equally, birds of group IV (n=23) were injected with purified and dialysed material from non-infected insect cells to serve as a positive control. Birds of group V (n=9) were treated as a negative control and received an injection of 500 µl sterile PBS.

At day 21 of life, animals of groups I to IV were intramuscularly challenged with 200 µl of $10^7$ 50% tissue culture infective dose ($TCID_{50}$)/ml of the virulent FAdV-C virus AG234. Birds of the negative control group were administered the same amount of sterile PBS intramuscularly.

Upon challenge, the birds were monitored daily for clinical signs. Necropsy was performed on all animals that died or had to be euthanized in the course of the study. Samples taken at regular intervals included blood (collected on days 7, 11, 14, 21, 28, 35 and 42) for detection of antibodies and cloacal swabs (collected on days 21, 28 and 35) or tissue from the large intestine (taken on day 42) for detection of virus excretion at regular intervals.

All remaining birds were killed at the termination of the experiment on day 42 of life.

The trial and all of the included procedures on experimental birds were discussed and approved by the institutional ethics committee and licensed by the Austrian government (license number BMWF-68.205/0196-II/3b/2012).

1.6. Antibody Response

Commercial FAdV Enzyme-Linked Immunosorbent Assay (ELISA)

Commercially available FAdV Group 1 Antibody Test Kit was obtained from BioChek (Reeuwijk, Holland) to test antibody levels in sera of each group before (day 21) and after challenge (days 28, 35 and 42).

Serum Neutralization Test (SNT)

Test sera were inactivated at 56° C. for 30 min. CEL cells were prepared from 14-day-old chicken embryos and plated in 96-well plates (Sarstedt, Wiener Neudorf, Austria) with a density of $1\times10^6$ cells/ml. The assay was performed according to a constant virus diluted serum method using 100 $TCID_{50}$/100 µl KR5. The plates were inoculated at 37° C. in 5% $CO_2$ and investigated for CPE after 5 days.

Fib-2 ELISA

After predetermining optimal virus- and serum-dilutions by checker-board titrations, 96-well ELISA plates (Nunc Medisorb, Roskilde, Denmark) were coated with 100 µl recombinant affinity-purified Fib-2 protein per well, diluted in coating buffer (0.015 M $Na_2CO_3$, 0.035 M $NaHCO_3$, pH 8.4) to a final concentration of 0.05 µg/ml. After 24 h, plates were washed and 100 µl of the test sera, diluted 1:100 in blocking buffer (Starting Block T20 PBS, Thermo Scientific), were added to each well for 1 h. Following a washing step, 100 µl Goat-Anti-Chicken-IgG-HRP (Southern Biotechnology, Birmingham, USA) diluted 1:5000 in PBS-0.05% v/v Tween 20 (Calbiochem, Darmstadt, Germany) were added to each well and incubated for 1 h. After another washing step, 100 µl TMB (tetramethylbenzidine) substrate (Calbiochem, Darmstadt, Germany) were added to each well and the plates were incubated for 15 min in the dark. The reaction was stopped with 100 µl 0.5 M sulphuric acid/well and the optical density (OD) of each well was measured with an ELISA reader (Sunrise-Basic, Tecan, Grödig, Austria) at a wavelength of 450 nm.

On each plate, a positive and a negative control were included. All sera were tested in duplicate and the OD is indicated as the mean value of the duplicates. A tentative cut-off value was established as the arithmetic mean of all OD values plus three times the standard deviation determined from serum samples from the negative control group.

1.7. Western Blot Analysis

Purified recombinant Fib-1, Fib-2 and Hex L1 proteins were boiled for 5 min in sample buffer containing 4% SDS and 10% mercaptoethanol, separated by 12% SDS-PAGE and electrotransferred onto BioTrace PVDF Transfer Membrane (Pall, Vienna, Austria). After 3 h of blocking with 3% (w/v) skim milk, the membrane was cut into strips which were incubated separately in the test sera (preabsorbed with 1% Sf9 cell powder, diluted 1:2000) for 1 h. After several washes with PBS-0.05% Tween 20, the membrane strips were incubated for 1 h with rabbit anti-chicken IgG-HRP conjugate (Sigma-Aldrich, Vienna, Austria) diluted 1:2500, followed by several washes and incubation with Clarity Western ECL substrate (Bio-Rad Laboratories GmbH, Vienna, Austria). Visualization was performed on x-ray film (Super RX, Fuji, Japan) after exposure for 12 sec.

1.8. Real-Time (Rt) PCR from Cloacal Swabs and Intestine

Excretion of challenge virus was investigated from cloacal swabs taken on days 7 and 14 post challenge (p.c.) and tissue samples taken from the large intestine at termination of the study (day 21 p.c.) from five birds of each group, using an rt PCR assay based on the 52K gene, following DNA extraction with a commercial system (Qiagen, Hilden, Germany) (Günes et al., J. Virol. Meth. 183 (2012), 147-153).

2. Results

2.1. Expression of Proteins

Characteristic morphologic changes were exhibited by Sf9 cell cultures within 48-96 h after inoculation with recombinant baculovirus. Recombinant proteins were detected by SDS-PAGE and Western blot as bands migrated to estimated molecular weight sizes of 51 kDa (Fib-1), 56 kDa (Fib-2) and 35 kDa (Hex L1) with peak expression around 72 h after inoculation. Furthermore, expression analysis showed that large fractions of Fib-1 and Fib-2 were expressed as soluble proteins in the supernatant, whereas Hex L1 protein was preferentially found in the pellet.

2.2. Protection of Recombinant Proteins Against Virulent FAdV

Following challenge, clear-cut differences in severity of clinical signs and mortality rates were noticed between individual groups (FIG. 1). The difference in mortality between the groups was found to be highly significant by chi-square analysis ($\chi^2=46$; $p<0.01$) and significant differences were also indicated in the pairwise comparison of mortality between the Fib-2 vaccinated group and all other challenged groups (Bonferroni corrected chi-square test).

Onset of mortality was recorded on day 3 p.c., in coincidence with the overall peak of mortality. Dead birds were observed until day 5 p.c., and after that no more animals died. After infection with the virulent virus, birds of group IV (positive control) showed severe clinical depression as manifested by huddling together with ruffled feathers, and 18 out of 23 animals (78%) died. In contrast, birds in group II (Fib-2 vaccinated) displayed no apparent clinical symptoms and only one dead animal out of 28 on day 3 p.c. after the challenge was recorded. Birds of group I (Fib-1 vaccinated) partially showed clinical symptoms and 10 out of 26 animals died resulting in an overall mortality of 38%. In group III (Hex L1 vaccinated), severity of clinical affection was comparable to the positive control group, and 19 out of 26 animals (73%) died. Necropsy revealed severe lesions in heart and liver of all animals found dead or those which had to be euthanized during the experiment. Characteristic findings included straw-colored fluid in the pericardial sac and focal necrosis in the livers (FIG. 2).

Surviving animals of clinically affected groups experienced full recovery by 26 days of life. No more lesions were recorded in any of the surviving animals at termination of the experiment on day 42 of life. In group V (negative control), no clinical signs were observed at any time of the experiment and no pathological lesions were noticed at termination of the study.

2.3. Detection of Antibodies

Commercial FAdV ELISA and SNT

No antibodies were detected with the commercial ELISA and the SNT prior to challenge at day 21 in any of the groups (FIGS. 3a and 3b). Following challenge, birds of groups I-IV developed an increase in antibody levels detectable by both commercial ELISA and SNT. In the vaccinated groups, antibodies measured by commercial ELISA increased until 7 d.p.c. and after that gradually declined, whereas antibody levels in the positive control group display a continuous increase until termination of the experiment. Development of neutralizing antibodies p.c. continuously increased in groups I-IV with highest titres obtained in non-vaccinated birds No antibodies were detected in negative control animals at any of the tested time points during the experiment.

Fib-2 ELISA

To investigate a specific antibody response against Fib-2 prior to and after challenge a custom-made ELISA using recombinant purified protein was developed. Starting measurements in Fib-2 vaccinated birds on day 7, the ELISA first detected an increase in mean OD value above the determined cut-off on day 11 and peaked at 7 d.p.c. (FIG. 3b). Until termination of the experiment, mean Fib-2 antibody levels declined only slightly. Of note, the antibody response of the bird that did not survive challenge was only 0.21 and differed significantly from all other birds.

Birds of the positive control group were tested negative for Fib-2 antibodies on day 21. Survivors, however, developed a strong anti-Fib-2 response p.c., reaching the level of vaccinated birds by the end of the experiment.

Sera obtained from the negative control group before and after challenge were tested negative in the Fib-2 ELISA (FIG. 3c), similarly to sera from Fib-1 and Hex L1 vaccinated groups.

2.4. Western Blot

Immunoblots with sera from three birds of each group I-III obtained on day 21 after administration of recombinant proteins confirmed the presence of antibodies against Fib-1, Fib-2 and Hex L1, respectively (FIG. 4). No antibodies were detected in sera from one bird of the positive and negative control group when tested against each of the purified recombinant proteins in the immunoblot.

2.5. Virus Excretion

No virus excretion was detected in any of the samples taken from negative control animals (Table 2). Following challenge, viral excretion was noticed in all tested birds of groups I-IV, at 7 d.p.c with no evident difference in viral load between protein-vaccinated and positive control birds. Shedding was verified until termination of the experiment and the majority of birds were recorded positive for virus excretion in the faeces. The large intestine of half of the infected birds was positive at termination of the study, with positive birds in each of the groups I-IV.

3. Discussion

While human adenoviruses are well studied on a molecular basis for their use as vaccine and gene therapy vectors, current understanding of FAdV-host interaction and molecules involved is still limited. Interaction between capsomer and host cell has been established as the critical factor in formation of host immunity, rendering adenovirus capsid proteins interesting candidates for subunit vaccine development. In regard to the prevention of HHS, E. coli expressed penton base was recently proposed as a potential subunit antigen. In the present study, the efficacy of fiber subunit immunization derived from FAdV-C was investigated by utilizing for the first time the novel finding of two distinct fiber-encoding genes in FAdV-C. In addition, hexon loop-1, a surface-exposed structure with immunogenic potential, was investigated.

The choice of the baculovirus expression system was based on evidence for possible post-translational modifications of such adenovirus proteins.

Upon challenge with the virulent strain AG234, different degrees of protection were observed in chickens vaccinated with recombinant FAdV capsid proteins. Although Hex L1-specific antibodies were detected prior to challenge, this protein could not be proven as an effective subunit antigen in our study. In comparison, an immune response directed against Fib-2 is highly efficacious as it prevents any clinical signs of disease. This could indicate a key role of the Fib-2 protein in the initial steps of infection, possibly by mediating attachment to host cell receptors. Cellular attachment via binding of fiber to the ubiquitously present coxsackievirus-adenovirus receptor (CAR) is a well-known mechanism in human adenoviruses. However, knowledge about CAR-fiber interaction is primarily derived from in vitro studies and the role of CAR as primary receptor for adenovirus entry into the host cell is increasingly questioned. In this context, binding to primary receptors specific for avian—but not mammalian,—cells was suggested to be mediated by the short fiber of CELO. Previous phylogenetic data show a higher degree of relatedness of FAdV-C Fib-2 with the short fiber gene of CELO and the single fiber gene found in other FAdV species, as compared to Fib-1. Based on these informations, together with the actual finding of highly efficacious immune response directed against FAdV-C Fib-2, Fib-2 could serve as the primary ligand for induction of a host-cell dependent infection pathway.

Antibodies raised against Fib-2 following vaccination were detected with the exception of one bird, indicating a correlation with protection, in contrast to the commercial ELISA which failed to detect antibodies before challenge. Obviously, the type specificity of the fiber antigen results in a binding incompatibility of the induced antibodies within the commercial ELISA test system. The results obtained from SNT indicate that antibodies directed against Fib-2 do not possess neutralizing capacity, which is in agreement with previously reported observations of weak or lacking serum neutralization activity elicited by fiber if administered as an isolated virus component.

The challenge virus was detected in cloacal swabs of groups I-IV alike, demonstrating that vaccination does not prevent virus excretion and shedding, even in birds protected from clinical disease. This finding is supported by a previous study that reports excretion of challenge virus even in birds clinically fully protected by a live attenuated FAdV vaccine (Schonewille et al., Avian Dis. 54 (2010), 905-910).

In summary, identification of virulent strains of FAdV-C as causative agents of HHS together with the limitations faced by currently employed inactivated vaccines argue for the development of next-generation immunization strategies. The findings presented in the present invention shows high efficacy of recombinant Fib-2 protein for the development of an effective and safe subunit vaccine.

Tables

TABLE 1

Primers used.

| Primer name | Sequence (5'-3') | Position | Purpose |
|---|---|---|---|
| KR5-b Fib-1 f | 5'-GGATCCATGTCGG CCCTAATCG-3' | 30438-30453 [a] | Amplification of the fiber-1 gene of strain KR5 and cloning into the pFastBac vector |
| KR5-b Fib-1 r | 5'-AGGCCTTTAGGGG CTCGGAGC-3' | 31725-31739 [a] | Amplification of the fiber-1 gene of strain KR5 and cloning into the pFastBac vector |
| KR5-b Fib-2 f | 5'-AGGCCTATGCTCC GAGCCCCTA-3' | 31723-31738 [a] | Amplification of the fiber-2 gene of strain KR5 and cloning into the pFastBac vector |
| KR5-b Fib-2 r | 5'-TCTAGATTACGGG ACGGAGGCTG-3' | 33146-33162 [a] | Amplification of the fiber-2 gene of strain KR5 and cloning into the pFastBac vector |
| FAV f | 5'-AATTCCATGGACA AGTTCAGGCAGACGGT CGT-3' | 20481-20502 [a] | Amplification of the hexon loop-1 gene region of strain KR5 and cloning into the pFastBac vector |
| FAV r | 5'-TAACTCGAGCTAG TGATGCCGGGACATCA T-3' | 21347-21366 [a] | Amplification of the hexon loop-1 gene region of strain KR5 and cloning into the pFastBac vector |
| 52K-fw | 5'-ATGGCKCAGATGG CYAAGG-3' | 13075-13093 [b] | Amplification of the 52k gene in rt-PCR |
| 52K-rv | 5'-AGCGCCTGGGTCA AACCGA-3' | 13250-13232 [b] | Amplification of the 52k gene in rt-PCR |

[a] Position is indicated for the complete genomic KR5 sequence (HE608152).
[b] Position is indicated for the complete genomic CELO sequence (U46933).

TABLE 2

Detection of viral excretion in cloacal swab samples (taken on days 21, 28 and 35) and tissue from the large intestine (taken on day 42) by real-time PCR from five birds of each group. Results are shown as number of positive samples/number of samples tested.

| d[a] | group I (Fib-1) | group II (Fib-2) | group III (Hex L1) | group IV (positve control) | group V (negative control) |
|---|---|---|---|---|---|
| 21 | — | — | — | — | — |
| 28 | 5/5 | 5/5 | 5/5 | 5/5 | 0/5 |
| 35 | 3/5 | 4/5 | 4/5 | 4/5 | 0/5 |
| 42 | 1/5 | 3/5 | 5/5 | 1/5 | 0/5 |

[a] Day of life

TABLE 3

List of examples of fiber proteins useable according to the present invention:

Fowl adenovirus 4 isolate Punjab 1 fiber gene, complete cds
1,386 bp linear DNA
DQ864436.1 GI:112735223
Fowl adenovirus 4 isolate Punjab 2 fiber gene, complete cds
1,386 bp linear DNA
DQ864434.1 GI:112735219
Fowl adenovirus 4 short fiber gene, complete cds
1,482 bp linear DNA
AY340863.1 GI:33359662
Fowl adenovirus 10 short fiber protein gene, complete cds
1,496 bp linear DNA
AF007579.1 GI:2674070
Fowl adenovirus 4 isolate Kr-Yeoju short fiber gene, complete cds
1,425 bp linear DNA
HQ709232.1 GI:318040046
Fowl adenovirus 4 isolate Kr-Gunwi short fiber gene, complete cds
1,425 bp linear DNA
HQ709231.1 GI:318040044
Fowl adenovirus 4 isolate Kr-Andong short fiber gene, complete cds
1,425 bp linear DNA
HQ709230.1 GI:318040042
Fowl adenovirus 4 isolate Kr-Changnyeong short fiber gene, complete cds
1,425 bp linear DNA
HQ709229.1 GI:318040040
Fowl adenovirus partial sf gene for short fiber protein, isolate OTE
1,197 bp linear DNA
FN557186.1 GI:315455213
Fowl adenovirus partial sf gene for short fiber protein, isolate 08-5769
1,197 bp linear DNA
FN557185.1 GI:315455211
Fowl adenovirus partial sf gene for short fiber protein, isolate 08-3622
1,197 bp linear DNA
FN557184.1 GI:315455209
Fowl adenovirus 4 isolate Bareilly fiber protein gene, complete cds
1,437 bp linear DNA
FJ949088.1 GI:238683632
Fowl adenovirus C pVIII gene, U-exon gene, fiber-1 gene, fiber-2 gene and ORF22, isolate C2B
4,345 bp linear DNA
HE608154.1 GI:381214073
Fowl adenovirus C pVIII gene, U-exon gene, fiber-1 gene, fiber-2 gene and ORF22, isolate AG234
4,321 bp linear DNA
HE608153.1 GI:381214067
Fowl adenovirus C complete genome, isolate KR5
45,810 bp linear DNA
HE608152.1 GI:381214017
Fowl adenovirus C partial fiber-2 gene, isolate K388-95
1,395 bp linear DNA
FR872927.1 GI:381214013
Fowl adenovirus C partial fiber-2 gene, isolate 09/8846
1,440 bp linear DNA
FR872926.1 GI:381214011
Fowl adenovirus C partial fiber-2 gene, isolate 09/584
1,440 bp linear DNA
FR872925.1 GI:381214009
Fowl adenovirus C partial fiber-2 gene, isolate 09/2602
1,329 bp linear DNA
FR872924.1 GI:381213952
Fowl adenovirus C partial fiber-2 gene, isolate K99-97
1,340 bp linear DNA
FR872923.1 GI:381213950
Fowl adenovirus C partial fiber-2 gene, isolate Peru54
1,421 bp linear DNA
FR872922.1 GI:381213948
Fowl adenovirus C partial fiber-2 gene, isolate Peru53
1,416 bp linear DNA
FR872921.1 GI:381213946
Fowl adenovirus C partial fiber-1 gene, isolate K1013
1,184 bp linear DNA
FR872898.1 GI:381213900
Fowl adenovirus C partial fiber-1 gene, isolate 922/1
1,311 bp linear DNA
FR872897.1 GI:381213898
Fowl adenovirus C partial fiber-1 gene, isolate C2B
1,302 bp linear DNA
FR872896.1 GI:381213896
Fowl adenovirus C partial fiber-1 gene, isolate Da60
1,302 bp linear DNA
FR872895.1 GI:381213894
Fowl adenovirus C partial fiber-1 gene, isolate KR5
1,302 bp linear DNA
FR872894.1 GI:381213892
Fowl adenovirus C partial fiber-1 gene, isolate INT4 (QT-cell passaged AG234)
1,188 bp linear DNA
FR872893.1 GI:381213890
Fowl adenovirus C partial fiber-1 gene, isolate AG234
1,302 bp linear DNA
FR872892.1 GI:381213888
Fowl adenovirus C partial fiber-1 gene, isolate K31
1,181 bp linear DNA
FR872891.1 GI:381213886
Fowl adenovirus 4 isolate Kr-Yeoju short fiber gene, complete cds
1,425 bp linear DNA
HQ709232.1 GI:318040046
Fowl adenovirus 4 isolate Kr-Gunwi short fiber gene, complete cds
1,425 bp linear DNA
HQ709231.1 GI:318040044
Fowl adenovirus 4 isolate Kr-Andong short fiber gene, complete cds
1,425 bp linear DNA
HQ709230.1 GI:318040042
Fowl adenovirus 4 isolate Kr-Changnyeong short fiber gene, complete cds
1,425 bp linear DNA
HQ709229.1 GI:318040040
Fowl adenovirus partial sf gene for short fiber protein, isolate OTE
1,197 bp linear DNA
FN557186.1 GI:315455213
Fowl adenovirus partial sf gene for short fiber protein, isolate 08-5769
1,197 bp linear DNA
FN557185.1 GI:315455211
Fowl adenovirus partial sf gene for short fiber protein, isolate 08-3622
1,197 bp linear DNA
FN557184.1 GI:315455209
Fowl adenovirus 4 isolate Bareilly fiber protein gene, complete cds
1,437 bp linear DNA
FJ949088.1 GI:238683632
Fowl adenovirus 4 short fiber gene, complete cds
1,482 bp linear DNA
AY340863.1 GI:33359662
Fowl adenovirus 4 isolate Punjab 1 fiber gene, complete cds
1,386 bp linear DNA
DQ864436.1 GI:112735223
Fowl adenovirus 4 isolate Punjab 2 fiber gene, complete cds
1,386 bp linear DNA
DQ864434.1 GI:112735219
Fowl adenovirus 10 short fiber protein gene, complete cds
1,496 bp linear DNA
AF007579.1 GI:2674070

The nature of the sequence, the FAdV species/serotypes, the-length of the sequence, the GenBank accession number and the version is indicated for each of the sequences.

TABLE 4

List of species in the genus *Aviadenovirus*:

*Falcon adenovirus A*

| Falcon adenovirus | 1 | [AY683541] | (FaAdV-1) |

*Fowl adenovirus A*

| Fowl adenovirus | 1 | (CELO) [U46933 = AC_000014] | (FAdV-1) |

*Fowl adenovirus B*

| Fowl adenovirus | 5 | (340) [AF508952] | (FAdV-5) |

*Fowl adenovirus C*

| Fowl adenovirus | 4 | (ON1) [GU188428 = NC_015323] | (FAdV-4) |
| Fowl adenovirus | 10 | (CFA20) [AF160185] | (FAdV-10) |

*Fowl adenovirus D*

| Fowl adenovirus | 2 | (P7-A) [AF339915] | (FAdV-2) |
| Fowl adenovirus | 3 | (75) [AF508949] | (FAdV-3) |

TABLE 4-continued

List of species in the genus *Aviadenovirus*:

| Fowl adenovirus | 9 | (A2-A) [AF083975 = AC_000013] | (FAdV-9) |
| Fowl adenovirus | 11 | (380) [AF339925] | (FAdV-11) |

*Fowl adenovirus E*

| Fowl adenovirus | 6 | (CR119) [AF508954] | (FAdV-6) |
| Fowl adenovirus | 7 | (YR36) [AF508955] | (FAdV-7) |
| Fowl adenovirus | 8a | (CFA40) [AF155911] | (FAdV-8a) |
| Fowl adenovirus | 8b | (764) [AF508958] | (FAdV-8b) |

*Goose adenovirus*

| Goose adenovirus | 1 | (GoAdV-1) |

Species names are in italic script; names of types and isolates ( ) are in roman script.
Sequence accession numbers [ ] and assigned abbreviations ( ) are also listed.

The invention claimed is:

1. A vaccine for use in preventing hepatitis-hydropericardium syndrome (HHS) in birds comprising fiber-2 protein of Fowl Adenovirus C (FAdV-C), wherein the vaccine is further defined as a subunit vaccine comprising an immunoeffective amount of an adjuvant.

2. The vaccine of claim 1, wherein the adjuvant is Freund's complete adjuvant, Freund's incomplete adjuvant, aluminum hydroxide, *Bordetella pertussis*, saponin, muramyl dipeptide, ethylene vinyl acetate copolymer, oil, a vegetable oil or a mineral oil.

3. The vaccine of claim 2, wherein the adjuvant is peanut oil or silicone oil.

4. The vaccine of claim 1, wherein the fiber-2 protein of FAdV-C has a protein sequence of any one of SEQ ID NO: 9 through SEQ ID NO: 33.

5. The vaccine of claim 4, wherein the sequence of the fiber-2 protein of FAdV-C is the protein sequence of SEQ ID NO: 23.

6. The vaccine of claim 1, further comprising a pharmaceutically acceptable diluent and/or carrier.

7. The vaccine of claim 6, wherein the pharmaceutically acceptable diluent and/or carrier comprises a water-for-injection, physiological saline, tissue culture medium, propylene glycol, polyethylene glycol, vegetable oil, or an injectable organic ester.

8. The vaccine of claim 1, wherein the fiber-2 protein of FAdV-C is contained in an amount of 0.1 μg/ml to 10 mg/ml.

9. The vaccine of claim 8, wherein the fiber-2 protein of FAdV-C is contained in an amount of 1 μg/ml to 1 mg/ml.

10. The vaccine of claim 9, wherein the fiber-2 protein of FAdV-C is contained in an amount of 10 to 100 μg/ml.

11. The vaccine of claim 1, consisting of:
 fiber-2 protein of FAdV-C, in an amount of 0.1 μg to 10 mg; and
 a pharmaceutically acceptable carrier and/or diluent and/or adjuvant.

12. The vaccine of claim 11, wherein the fiber-2 protein of FAdV-C is in an amount of 1 μg to 1 mg.

13. The vaccine of claim 12, wherein the fiber-2 protein of FAdV-C is in an amount of 10 to 100 μg.

14. A method for preventing HHS in birds, comprising administering to the birds a vaccine of claim 1.

15. The method of claim 14, wherein the birds are in a parent flock.

16. The method of claim 14, wherein the birds are poultry.

17. The method of claim 16, wherein the poultry are broilers.

18. A kit comprising an isolated fiber-2 protein of FAdV-C immobilized on a solid surface or an immunogenic fragment of a fiber-2 protein of FAdV-C immobilized on a solid surface.

19. The kit of claim 18, further comprising a detection component that can detect the binding of an antibody to the immobilized fiber-2 protein of FAdV-C or the immobilized immunogenic fragment thereof.

\* \* \* \* \*

UNITED STATES PATENT AND TRADEMARK OFFICE
CERTIFICATE OF CORRECTION

PATENT NO. : 10,159,730 B2
APPLICATION NO. : 14/913152
DATED : December 25, 2018
INVENTOR(S) : Michael Hess et al.

It is certified that error appears in the above-identified patent and that said Letters Patent is hereby corrected as shown below:

On the Title Page

Item (71), Applicant:
Replace "VETERINARMEDIZINISCHE UNIVERSITAT WIEN" with
-- VETERINÄRMEDIZINISCHE UNIVERSITÄT WIEN --.

Signed and Sealed this
Fifth Day of March, 2019

Andrei Iancu
*Director of the United States Patent and Trademark Office*